US008383389B2

(12) United States Patent
Asano et al.

(10) Patent No.: US 8,383,389 B2
(45) Date of Patent: *Feb. 26, 2013

(54) HYDROXYNITRILE LYASE

(75) Inventors: Yasuhisa Asano, Toyama (JP); Takanori Akiyama, Yokohama (JP); Fujio Yu, Yokohama (JP); Eiji Sato, Yokohama (JP)

(73) Assignee: Mitsubishi Rayon Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/210,646

(22) Filed: Aug. 16, 2011

(65) Prior Publication Data

US 2012/0040417 A1 Feb. 16, 2012

Related U.S. Application Data

(63) Continuation of application No. 11/665,491, filed as application No. PCT/JP2005/019360 on Oct. 14, 2005, now Pat. No. 8,030,053.

(30) Foreign Application Priority Data

| Oct. 15, 2004 | (JP) | 2004-301718 |
| Dec. 8, 2004 | (JP) | 2004-355766 |
| Mar. 3, 2005 | (JP) | 2005-058857 |

(51) Int. Cl.
| *C12N 9/00* | (2006.01) |
| *C12N 9/88* | (2006.01) |
| *C12N 1/20* | (2006.01) |
| *C12N 15/00* | (2006.01) |

(52) U.S. Cl. ............. 435/232; 435/183; 435/252.3; 435/320.1; 536/23.2

(58) Field of Classification Search .............. None
See application file for complete search history.

(56) References Cited

U.S. PATENT DOCUMENTS

| 8,030,053 B2 * | 10/2011 | Asano et al. ............ 435/252.3 |
| 2003/0148440 A1 | 8/2003 | Effenberger et al. |

FOREIGN PATENT DOCUMENTS

| DE | 195 29 116 A1 | 3/1997 |
| EP | 0 969 095 | 1/2000 |
| EP | 1 033 405 A2 | 9/2000 |
| JP | 2000-125886 | 5/2000 |
| JP | 2005-245242 | 9/2005 |
| WO | WO 97/03204 A2 | 1/1997 |
| WO | WO 97/03204 A3 | 1/1997 |
| WO | 01 48178 | 7/2001 |
| WO | WO 03/016551 A2 | 2/2003 |
| WO | WO 2004/083424 A1 | 9/2004 |
| WO | 2005 095602 | 10/2005 |

OTHER PUBLICATIONS

U.S. Appl. No. 13/210,630, filed Aug. 16, 2011, Asano, et al.
Holger Bühler, et al., "Substrate Specificity of Mutants of the Hydroxynitrile Lyase from Manihot esculenta", ChemBioChem: A European Journal of Chemical Biology, vol. 4, No. 2-3, XP 002462622, ISSN: 1439-4227, Mar. 3, 2003, pp. 211-216.
R. Weis, et al., "Biocatalytic conversion of unnatural substrates by recombinant almond R-HNL isoenzyme 5", Journal of Molecular Catalysis B: Enzymatic, Elsevier, vol. 29, No. 1-6, XP 002382495, ISSN: 1381-1177, Jun. 21, 2004, pp. 211-218.
Extended European Search Report issued Sep. 20, 2010, European Patent Application No. 10171423.6.
Chica et al. Curr Opin Biotechnol, Aug. 2005;16(4):378-84.
Database Geneseq, "Manihot esculenta S-acetone-cyanohydrin lyase protein", Nov. 20, 2003, XP002600065.
Database UniProt, "SubName: Full=Alpha-hydroxynitrile lyase", Jun. 1, 1998, XP00260066.
Database Geneseq, "Hevea brasiliensis (S)-hydroxynitrilase", Jan. 9, 1998, XP002600067.
European Search Report issued Oct. 20, 2010, European Patent Application No. 10171421.0.
Set et al. Appl Biochem Biotechnol. Dec. 2007;143(3):212-23.
Office Action issued Apr. 19, 2011, in Japanese Application No. 2006-541007.
Gonghong Yan, et al., "A Single Residual Replacement Improves the Folding and Stability of Recombinant Cassava Hydroxynitrile Lyase in *E. coli*". Biotechnology Letters, vol. 25, No. 13, pp. 1041-1047, 2003.
PH.-Herve Hirel, et al. "Extent of N-Terminal Methionine Excision From *Escherichia coli* Proteins is Governed by the Side-Chain Length of the Penultimate Amino Acid", Proc. Natl. Acad.Sci. USA, Bol. 86, No. 21, pp. 8247-8251, 1989.
Alexander Varshavsky, "The N-End Rule:Functions, Mysteries, Uses", Proc. Natl. Acad.Sci. USA, vol. 93, No. 22, pp. 12142-12149, 1996.

* cited by examiner

*Primary Examiner* — Christian Fronda
(74) *Attorney, Agent, or Firm* — Oblon, Spivak, McClelland, Maier & Neustadt, L.L.P.

(57) ABSTRACT

An improved hydroxynitrile lyase characterized by having a mutation of substitution of at least one amino acid residue in the amino acid sequence of a wild-type hydroxynitrile lyase with another amino acid and by its hydroxynitrile lyase activity per transformant being higher than the hydroxynitrile lyase activity per transformant into which the wild-type hydroxynitrile lyase gene is introduced; and a method for producing a hydroxynitrile lyase, comprising expressing the improved hydroxynitrile lyase in a host and recovering the improved hydroxynitrile lyase from the resultant culture.

31 Claims, 11 Drawing Sheets

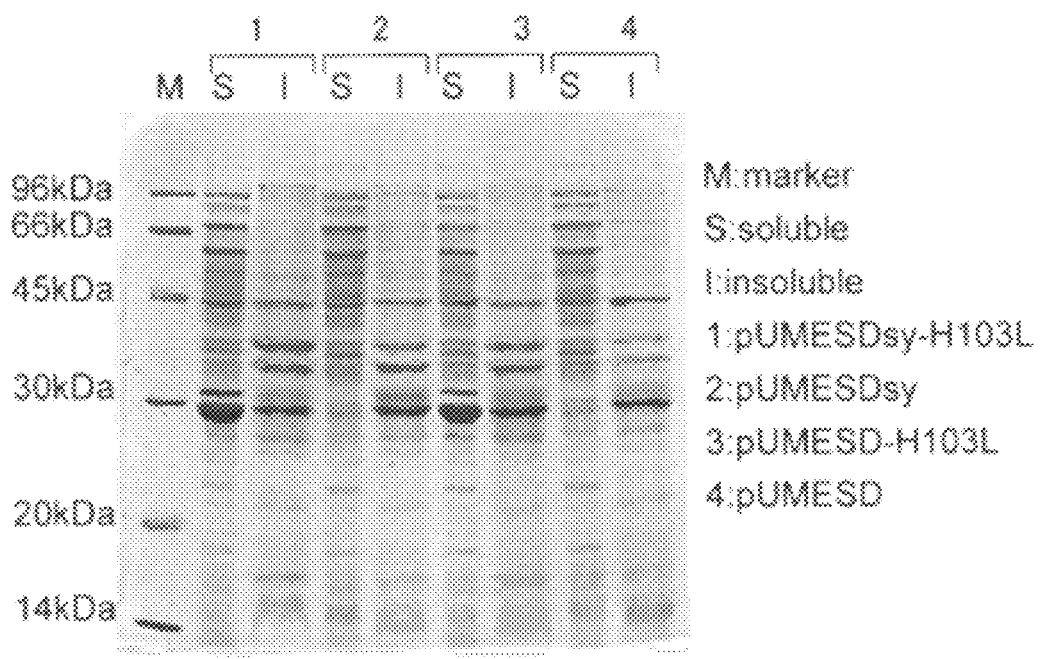

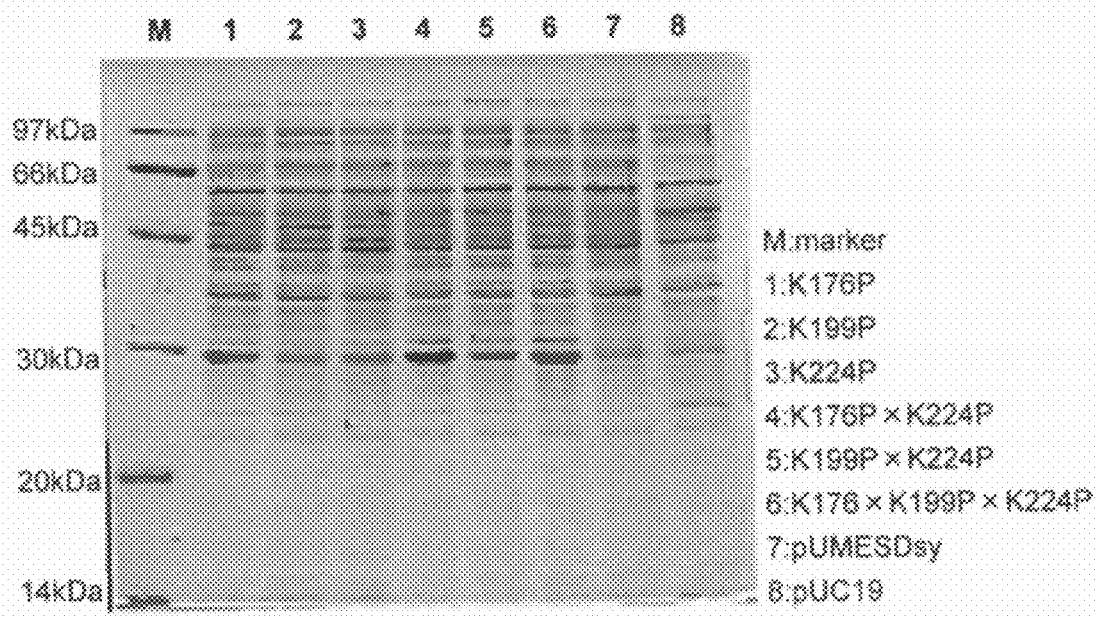

HYDROXYNITRILE LYASE

TECHNICAL FIELD

The present invention relates to an improved hydroxynitrile lyase and a method for producing the improved hydroxynitrile lyase.

BACKGROUND ART

Hydroxynitrile lyase is an enzyme that catalyzes a reaction for producing cyanohydrins. Briefly, hydroxynitrile lyase is an enzyme catalyst used in the synthesis of cyanohydrins (α-hydroxynitriles) from carbonyl compounds in the presence of a cyanide donor. Cyanohydrins can be converted into various compounds and are useful as intermediates in organic synthesis. Further, optically active cyanohydrins may be used in the synthesis of α-hydroxyacids, α-hydroxyketones, β-aminoalcohols and the like, and are extremely useful in the synthesis of various important optical intermediates which are used for producing, for example, pharmaceuticals and chemicals. Therefore, development of a method for producing a large quantity of hydroxynitrile lyase is desired.

The hydroxynitrile lyase that catalyzes cyanohydrin synthesis is classified into the two groups of (S) selective group and (R) selective group. Of these groups, (S)-hydroxynitrile lyase catalyzes a reaction to produce (S)-cyanohydrin from either ketone or aldehyde and a cyanide compound under acidic conditions. As a representative reaction of this type, a reaction may be given in which (S)-mandelonitrile is produced from benzaldehyde and a cyanide compound, prussic acid. (S)-Hydroxynitrile lyase is also used as a biocatalyst capable of producing from inexpensive substrates optically active substances highly useful as intermediates for pharmaceuticals and chemicals. Thus, (S)-hydroxynitrile lyase is extremely useful in many fields. In order to utilize hydroxynitrile lyase in industrial production of optically active cyanohydrins, development of a method for producing a large quantity of a hydroxynitrile lyase which has high activity per cell or protein and high stereo-selectivity is desired.

It is known that hydroxynitrile lyase exists only in those plants that have cyanogenic glucosides. For example, as (R)-hydroxynitrile lyases, those derived from plants of the family Rosaceae, such as almond (*Prunus amygdalus*), are known. Further, as (S)-hydroxynitrile lyases, those derived from plants of the family Gramineae, such as sorghum (*Sorghum bicolor*); plants of the family Euphorbiaceae, such as cassava (*Manihot esculenta*) and Para rubber tree (*Hevea brasiliensis*); and plants of the family Olacaceae, such as tallow wood (*Ximenia americana*); are known. However, it has only been possible to extract extremely small quantities of hydroxynitrile lyases from these plants.

In order to obtain a large quantity of a hydroxynitrile lyase which is useful in pharmaceutical and chemical fields, attempts to obtain such a hydroxynitrile lyase with genetic engineering methods have been made[1-9]. However, when a heterologous protein is expressed using a transformant, results obtained from researches on a corresponding homologous protein (such as yield, biochemical activities, etc.) are not always applicable. In other words, when a heterologous proteins is expressed using a transformant, it is not easy to predict the behavior and expression level of the transformant, the biochemical activities of the protein of interest, and so forth.

Further, depending on the type of the protein to be expressed, normal folding of the protein may not occur in the transformed host, resulting in the formation of an inclusion body. It is known that, in many cases, the protein within this inclusion body becomes an inactive protein without its inherent activity. In hydroxynitrile lyase, it is reported, for example, that 99% of hydroxynitrile lyase which has been expressed by culturing an *Escherichia coli* transformant at 37° C. is found in the insoluble fraction in the form of an inactive inclusion body[1]. It is also reported that the enzyme activity of crude enzyme solution produced using *E. coli* is 0.545 units/mg protein[2-4]; that the liquid activity of crude enzyme solution produced using *E. coli* (host: M15[pREP4]) is 0.5 U/ml[14]; and that the specific activities of crude enzyme solutions are 0.20 U/mg protein (host: Top10', 28° C.) and 0.61 U/mg protein (host: XL1-blue, 22° C.), respectively[15, 16]. However, none of the above-mentioned enzyme activities is satisfactory.

As means to solve these problems, for example, an attempt has been made in which a hydroxynitrile lyase-expressing *E. coli* transformant is cultured at a low temperature to thereby inhibit the formation of inclusion bodies and improve the yield of a hydroxynitrile lyase having activity[8]. However, this technology requires a long time for cultivation and needs to use large quantities of utility such as electricity and cooling water for maintaining the low temperature. Considering industrial production of hydroxynitrile lyase, these drawbacks will increase production cost greatly.

On the other hand, due to recent advancement in recombinant DNA techniques, it has become rather easy to prepare a mutant protein in which one or more amino acids constituting the original protein are deleted, added, inserted or substituted with other amino acids. In particular, when the protein of interest is an enzyme, it is known that mutants thereof acquire improvement in properties such as stability, resistance to organic solvents, thermal resistance, acid resistance, alkali resistance, substrate specificity or substrate affinity compared to the original enzyme, depending on the sites of the amino acid residues deleted, added, inserted or substituted and the types of the amino acids which replace those amino acids. These improvements in properties may bring about large reduction of production cost in industrial production utilizing enzyme reactions, through stabilization of enzymes as catalysts, simplification of reaction steps, improvement of reaction yield and so forth. Therefore, a large number of improved enzymes with various improved properties are now being developed.

In hydroxynitrile lyase, mutants in which one or more constituent amino acids are deleted, added, inserted or substituted have also been reported. For example, it is reported that a mutant hydroxynitrile lyase has an improved affinity to aromatic aldehydes, in particular, 3-phenoxybenzaldehyde[9, 10]. However, a great increase in the production yield of hydroxynitrile lyase has not been achieved yet. It is also reported that a mutant in which tryptophan at position 128 is substituted with another amino acid and a mutant in which cysteine at position 81 is substituted with alanine were prepared and transformed into *E. coli* M15. When these *E. coli* M15 transformants were cultured in TB medium containing 100 μM IPTG under conditions cooled from 37° C. to 20° C., some of the mutant-expressing M15 transformants exhibited a hydroxynitrile lyase activity per cell higher than that exhibited by the wild-type hydroxynitrile lyase-expressing M15 transformants[6]. However, according to this document, the hydroxynitrile lyase activity of the wild-type hydroxynitrile lyase-expressing M15 transformants is about ½ of that of the wild-type hydroxynitrile lyase-expressing JM109 transformants obtained under the same culture conditions. Thus, the effects of mutants are not necessarily demonstrated in hosts with high expression ability. It is also reported that substitution of glycine at position 113 with serine in a hydroxynitrile lyase derived from a subspecies of cassava (*Manihot esculenta*) grown in China increased the specific activity of the resultant mutant hydroxynitrile lyase[11]. However, the amino acid at position 113 of the hydroxynitrile lyase derived from common cassava (*Manihot esculenta*) is serine. Thus, this report merely shows that this amino acid is important for hydroxynitrile lyase activity.

On the other hand, it is reported that the N-terminal methionine present at the time of translation undergoes processing in 40% of the proteins in *E. coli* cell extract[17]. This processing is catalyzed by an enzyme called methionine aminopeptidase[18]. It is reported that whether or not an endogenous protein in *E. coli* cells is ready to undergo processing by aminopeptidase is decided by the type of the amino acid at position 2 of the protein; and that the larger the side chains of the amino acid at position 2 is, it is more difficult for the protein to undergo the processing[12]. There is also reported an N-end rule that "the stability of a protein in *E. coli* cells is decided by the type of the N-terminus amino acid of the protein"[13]. According to this N-end rule, when the N-terminus of a protein is arginine, lysine, leucine, phenylalanine, tyrosine, tryptophan or the like, the stability of the protein in cells is low and the protein is readily degraded. Based on these findings, it may be possible to improve the stability of a protein of interest in a host transformant by selecting at position 2 of the protein an amino acid which has large side chains (i.e., hard to undergo the processing by methionine aminopeptidase) and which is not arginine, lysine, leucine, phenylalanine, tyrosine or tryptophan. However, the above-described results[12, 13] were obtained from analysis of endogenous proteins in hosts or some model proteins. Therefore, hydroxynitrile lyase which is a heterologous protein to a host will not necessarily follow the above-described rule because, as mentioned earlier, when a heterologous protein is expressed using a transformant, it is very difficult to predict the behavior and expression level of the transformant, the biochemical activities of the protein of interest, etc.

As described so far, attempts to obtain a hydroxynitrile lyase with remarkably improved properties can not be said successful. Creation of still more useful hydroxynitrile lyase mutants has been strongly desired.

REFERENCES (1) Japanese Unexamined Patent Publication (kohyo) No. 11-508775
(2) Japanese Unexamined Patent Publication No. 2000-189159
(3) Japanese Unexamined Patent Publication No. 2000-189160
(4) Japanese Unexamined Patent Publication No. 2000-245486
(5) Japanese Unexamined Patent Publication No. 2002-330791
(6) International Publication WO 01/48178
(7) Japanese Unexamined Patent Publication No. 2004-194550
(8) Japanese Unexamined Patent Publication No. 2004-194551
(9) Japanese Unexamined Patent Publication No. 2000-125886
(10) Holger Buhler et al, Chembiochem. 4 (2003) 211-216
(11) Gonghong Yan et al, Biotechnol. Lett. 25 (2003) 1041-1047
(12) Ph.-Herve Hirel et al, Proc. Natl. Acad. USA 86 (1989), 8247-8251
(13) Alexander Varshaysky, Proc. Natl. Acad. USA 93 (1996), 12142-12149
(14) Siegfried Forster et al, Angew. Chem. Int. Ed. Engl. 35 (1996) 437-439
(15) Meinhard Hasslacher et al, J. Biol. Chem. 271 (1996), 5884-5891
(16) Meinhard Hasslacher et al, Protein Expression and Purification 11 (1997), 61-71
(17) Waller, J.P. et al, J. Mol. Bio. 7 (1963), 483-496
(18) Ben-Bassat, A. et al, J. Bacteriol. 169(1987), 751-757

DISCLOSURE OF THE INVENTION

It is an object of the present invention to provide an improved hydroxynitrile lyase and a method for producing the improved hydroxynitrile lyase.

As a result of extensive and intensive researches toward the solution of the above-described problems, the present inventors have found that it is possible to greatly improve hydroxynitrile lyase activity per transformant by substituting at least one amino acid residue in the amino acid sequence of a wild-type hydroxynitrile lyase with another amino acid. Thus, the present invention has been achieved.

The present invention relates to the following inventions.

(1) An improved hydroxynitrile lyase selected from any one of the following (A) to (G):

(A) an improved hydroxynitrile lyase in which the amino acid residue at position 2 of the amino acid sequence of a wild-type hydroxynitrile lyase is substituted with another amino acid residue;

(B) an improved hydroxynitrile lyase in which the histidine residue at position 103 or a neighboring position thereto of the amino acid sequence of a wild-type hydroxynitrile lyase is substituted with another amino acid residue;

(C) an improved hydroxynitrile lyase in which at least one lysine residue of the amino acid sequence of a wild-type hydroxynitrile lyase is substituted with another amino acid residue;

(D) an improved hydroxynitrile lyase in which the amino acid residue at position 2 and the histidine residue at position 103 or a neighboring position thereto of the amino acid sequence of a wild-type hydroxynitrile lyase are substituted with other amino acid residues;

(E) an improved hydroxynitrile lyase in which the amino acid residue at position 2 and at least one lysine residue of the amino acid sequence of a wild-type hydroxynitrile lyase are substituted with other amino acid residues;

(F) an improved hydroxynitrile lyase in which the histidine residue at position 103 or a neighboring position thereto and at least one lysine residue of the amino acid sequence of a wild-type hydroxynitrile lyase are substituted with other amino acid residues;

(G) an improved hydroxynitrile lyase in which the amino acid residue at position 2, the histidine residue at position 103 or a neighboring position thereto and at least one lysine residue of the amino acid sequence of a wild-type hydroxynitrile lyase are substituted with other amino acid residues.

(2) The improved hydroxynitrile lyase of (1) above, wherein the wild-type hydroxynitrile lyase is derived from cassava (*Manihot esculenta*) or Para rubber tree (*Hevea brasiliensis*).

(3) The improved hydroxynitrile lyase of (1) or (2) above, wherein the amino acid residue at position 2 is substituted with any amino acid selected from the group consisting of lysine, asparagine, isoleucine, arginine, glutamine, proline, threonine, tyrosine, leucine, methionine, serine and glutamic acid.

(4) The improved hydroxynitrile lyase of any one of (1) to (3) above, wherein the histidine residue at position 103 or a neighboring position thereto is substituted with an amino acid having one or both of the following properties (a) and (b):
(a) an amino acid containing one or two nitrogen atoms in its molecule;
(b) a neutral amino acid.
(5) The improved hydroxynitrile lyase of any one of (1) to (4) above, wherein the histidine residue at position 103 or a neighboring position thereto is substituted with any amino acid selected from the group consisting of methionine, leucine, isoleucine, valine, cysteine, glutamine, serine, threonine, alanine and tryptophan.
(6) The improved hydroxynitrile lyase of any one of (1) to (5) above, wherein at least one lysine residue present in a region from positions 175 to 224 of the amino acid sequence of the wild-type hydroxynitrile lyase is substituted with another amino acid.
(7) The improved hydroxynitrile lyase of any one of (1) to (6) above, wherein at least one lysine residue present in a region from positions 175 to 224 of the amino acid sequence of the wild-type hydroxynitrile lyase is substituted with an amino acid having one or both of the following properties (a) and (b):
(a) an amino acid containing one or two nitrogen atoms in its molecule;
(b) a neutral amino acid.
(8) The improved hydroxynitrile lyase of any one of (1) to (7) above, wherein at least one lysine residue present in a region from positions 175 to 224 of the amino acid sequence of the wild-type hydroxynitrile lyase is substituted with proline.
(9) The improved hydroxynitrile lyase of any one of (1) to (8) above, wherein at least one lysine residue selected from the group consisting of the lysine residues at positions 176, 199 and 224 in the amino acid sequence as shown in SEQ ID NO: 1 is substituted with another amino acid.
(10) The improved hydroxynitrile lyase of any one of (1) to (8) above, wherein at least one lysine residue selected from the group consisting of the lysine residues at positions 175, 198 and 223 in the amino acid sequence as shown in SEQ ID NO: 102 is substituted with another amino acid.
(11) An improved hydroxynitrile lyase consisting of the amino acid sequence of the improved hydroxynitrile lyase of any one of (1) to (10) above, wherein one or several amino acids other than those amino acids at the substitution positions specified in (A) to (G) are deleted, substituted or added.
(12) An improved hydroxynitrile lyase gene encoding the improved hydroxynitrile lyase of any one of (1) to (11) above.
(13) A recombinant vector comprising the improved hydroxynitrile lyase gene of (12) above.
(14) A transformant obtained by introducing the recombinant vector of (13) above into a host.
(15) A culture obtained by culturing the transformant of (14) above.
(16) An improved hydroxynitrile lyase recovered from the culture of (15) above.
(17) A method for producing an improved hydroxynitrile lyase, comprising recovering the improved hydroxynitrile lyase from the culture of (15) above.
(18) A method for producing a cyanohydrin, comprising treating a ketone compound or aldehyde compound, and a cyanide compound with the improved hydroxynitrile lyase of any one of (1) to (11) and (16) above and recovering the cyanohydrin from the treated culture.
(19) A method for producing a hydroxycarboxylic acid, comprising hydrolyzing the cyanohydrin obtained by the method of (18) above.

BRIEF DESCRIPTION OF THE DRAWINGS

FIG. 5 is a diagram showing the results of SDS-PAGE analysis on cell extract soluble fractions (S) and insoluble fractions (I) prepared respectively from an *E. coli* codon wild-type hydroxynitrile lyase-expressing transformant (JM109/pUMESDsy), a plant codon wild-type hydroxynitrile lyase-expressing transformant (JM109/pUMESD), a transformant expressing an improved hydroxynitrile lyase obtained by introducing H103L mutation into the *E. coli* codon wild-type hydroxynitrile lyase (JM109/pUMESDsy-H103L), and a transformant expressing an improved hydroxynitrile lyase obtained by introducing H103L mutation into the plant codon wild-type hydroxynitrile lyase (pUMESD-H103L) in Example 9.

Figure 8:
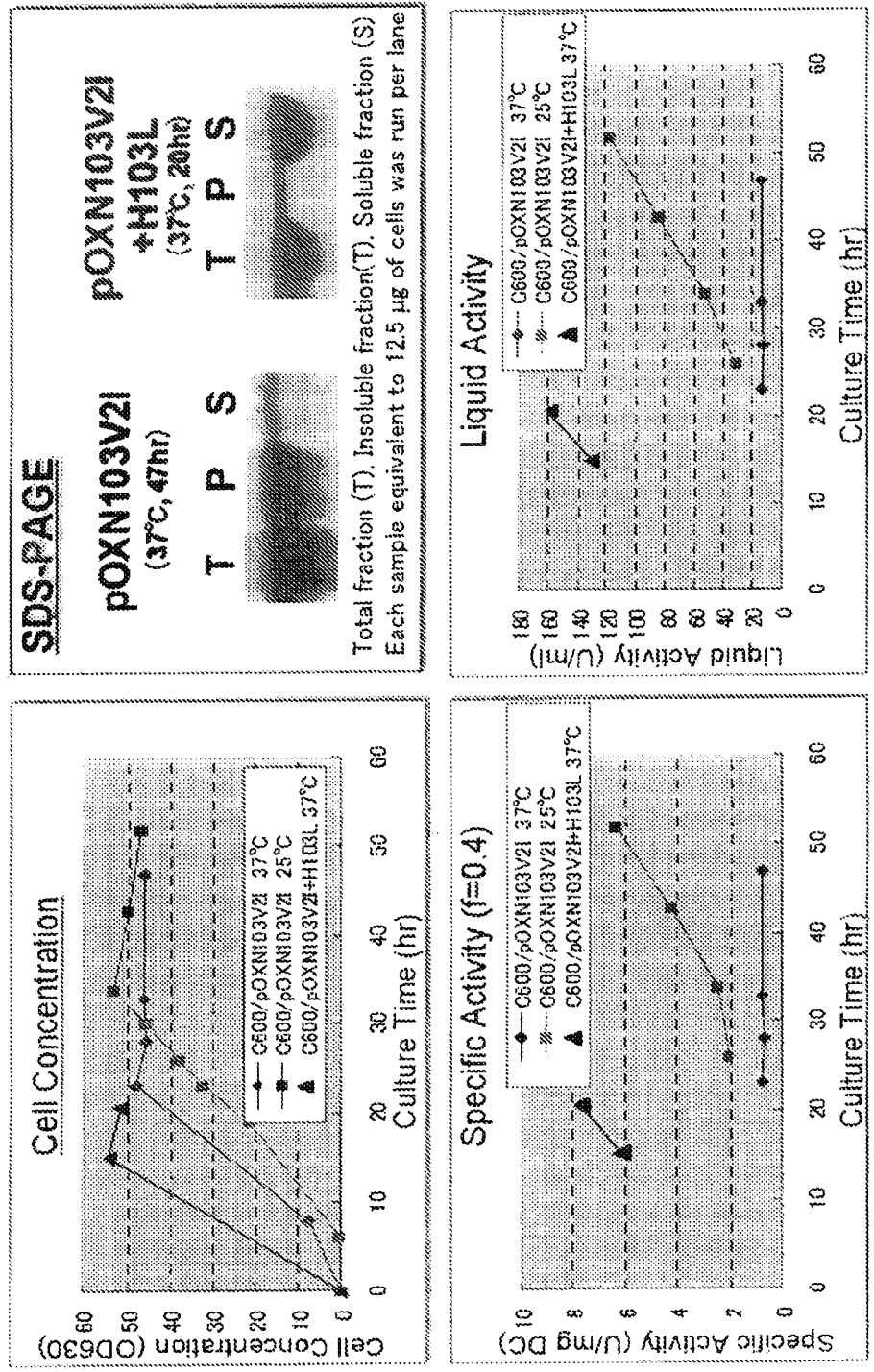

FIG. 8 shows the results of cell concentration, activity (specific activity and liquid activity) and SDS-PAGE (evaluation of T: total fraction; P: insoluble fraction; S: soluble fraction) in the evaluation of jar cultivation of V2I mutation-introduced, plant codon improved hydroxynitrile lyase-expressing transformant (C600/pOXN103V2I) and V2I and H103L mutations-introduced, plant codon combined type improved hydroxynitrile lyase-expressing transformant (C600/pOXN103V2I+H103L) in Example 12.

Figure 9:
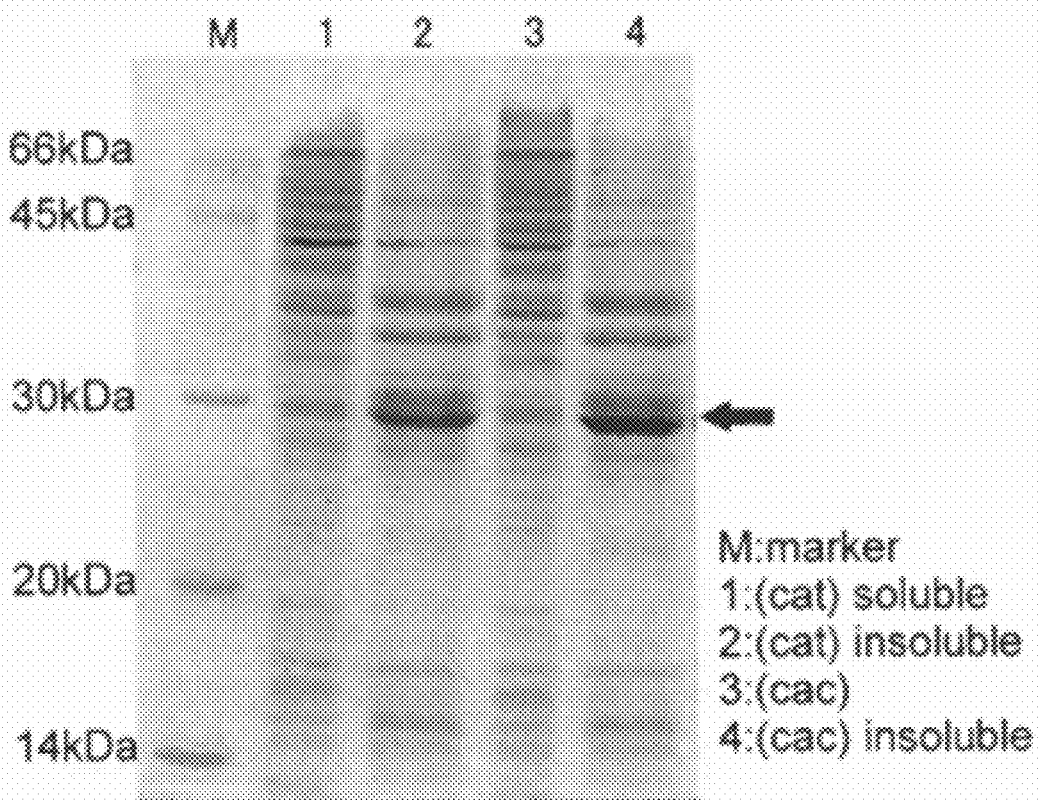

FIG. 9 shows the results of SDS-PAGE analysis in Example 13 which examined the effect of difference in the codon encoding H103 residue in the *E. coli* codon wild-type hydroxynitrile lyase upon expression levels.

Figure 10:
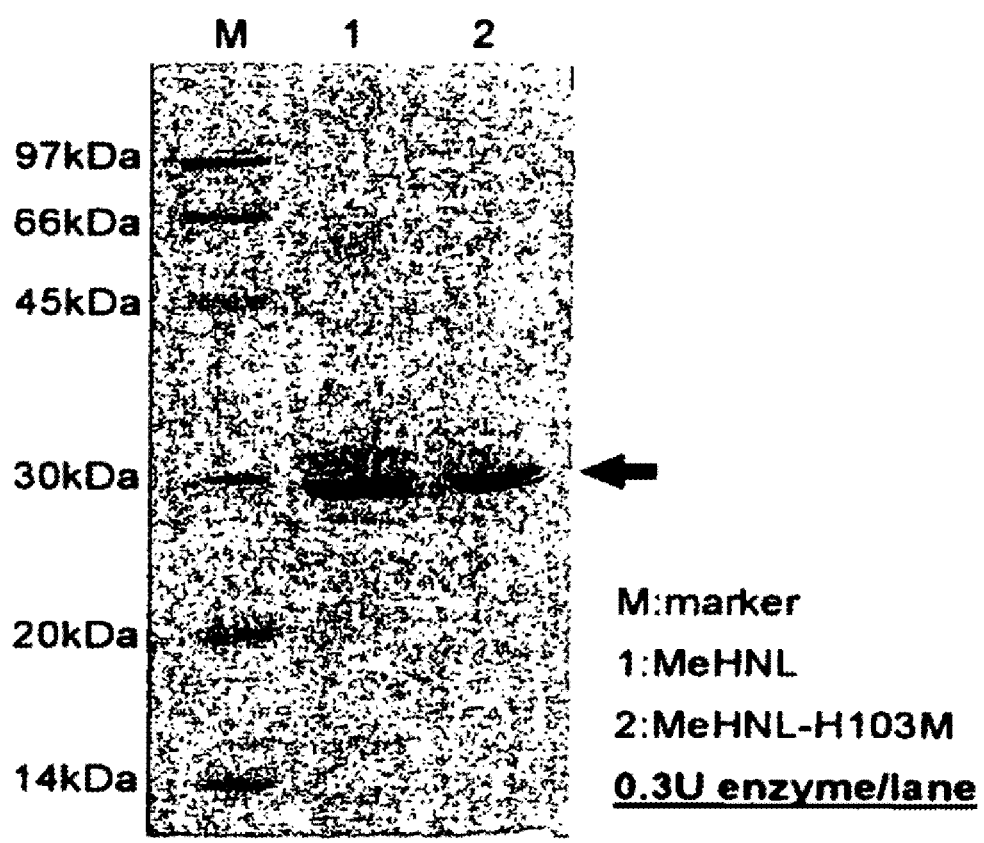

FIG. 10 shows the results of SDS-PAGE analysis on purified wild-type hydroxynitrile lyase (MeHNL) and purified H103M improved hydroxynitrile lyase (MeHNL-H103M) in Example 14.

FIG. 11 shows the results of SDS-PAGE analysis on 10 μg of protein samples derived from soluble fractions of lysine residue-substituted mutants in Examples 15 and 16.

BEST MODE FOR CARRYING OUT THE INVENTION

Hereinbelow, embodiments of the present invention will be described. These embodiments are provided only to illustrate the present invention, and the present invention is not limited to these embodiments. The present invention may be practiced in various ways without departing from the gist of the present invention. All publications, and patent publications such as unexamined patent publications and issued patent publications cited herein are incorporated herein by reference in their entirety.

The present invention is based on a finding that it is possible to greatly improve hydroxynitrile lyase activity per transformant by substituting at least one amino acid residue in the amino acid sequence of a wild-type hydroxynitrile lyase with another amino acid.

(I) Hydroxynitrile Lyase Activity

The term "hydroxynitrile lyase activity" used in the present specification means both the activity to catalyze reactions producing a cyanohydrin from either ketone or aldehyde and a cyanide compound (hereinafter, referred to as "synthesis activity") and the activity to catalyze reverse reactions thereof (hereinafter, referred to as "degradation activity"). In the present invention, the synthesis activity may be calculated by measuring the amount of (S)-mandelonitrile generated from benzaldehyde. Generation of mandelonitrile may be quantitatively determined, for example, by HPLC. The degradation activity may be calculated by measuring the amount of benzaldehyde generated from mandelonitrile (substrate). Generation of benzaldehyde may be quantitatively determined, for example, by tracing increase in absorbance at 280 nm when an improved hydroxynitrile lyase and racemic mandelonitrile are added to a sodium citrate buffer.

The present invention relates to an improved hydroxynitrile lyase obtainable by substituting some amino acid residues of the amino acid sequence of a wild-type hydroxynitrile lyase with other amino acids. The improved hydroxynitrile lyase of the present invention is, as described later, characterized by its hydroxynitrile lyase activity per transformant being higher than the hydroxynitrile lyase activity per transformant of the corresponding wild-type hydroxynitrile lyase. The essential cause which brought about the above-described improvement in activity per transformant may be any cause as long as it is attributable to the introduction of mutation. For example, improvement in the specific activity per enzyme protein itself, improvement in the ability to form active conformation, increase in the expression level in transformants (in particular, soluble fraction) and the like may be enumerated. Further, improvement in resistances, such as resistance to metal ions, resistance to organic solvents, thermal resistance, acid resistance or alkali resistance, may also be enumerated. Therefore, the improved hydroxynitrile lyase of the present invention may be a hydroxynitrile lyase whose hydroxynitrile lyase activity per transformant has been increased by the introduction of mutation. The improved hydroxynitrile lyase of the present invention also includes a hydroxynitrile lyase whose specific activity per enzyme protein itself has been increased; a hydroxynitrile lyase whose ability to form active conformation has been increased; or a hydroxynitrile lyase whose expression level per transformant has been increased.

As used herein, the term "activity per transformant" means hydroxynitrile lyase activity per transformant culture equipment, per culture broth, per amount of transformant (wet or dry), per (crude) enzyme solution, per soluble fraction, per weight of protein or the like in enzyme solution. High (low) in this activity means that hydroxynitrile lyase activity (specific activity, liquid activity) per unit weight of protein in enzyme solution or the like, or per unit volume of enzyme solution or the like is higher (lower) than that of control.

As used herein, the term "specific activity" means hydroxynitrile lyase activity per unit weight of protein or per unit cell mass.

As used herein, the term "liquid activity" means hydroxynitrile lyase activity per unit volume of solution.

(II) Hydroxynitrile Lyase (II-1) Wild-Type Hydroxynitrile Lyase

The improved hydroxynitrile lyase of the present invention has been improved by introducing a mutation into a wild-type hydroxynitrile lyase. The source of this wild-type hydroxynitrile lyase is not particularly limited. However, plant-derived hydroxynitrile lyases are preferable. As used herein, the term "wild-type hydroxynitrile lyase" refers to a hydroxynitrile lyase which can be isolated from an organism (such as plant) in the natural world and means that this hydroxynitrile lyase has no intentional or unintentional alterations in the sequence of amino acids constituting the enzyme (such as deletion or insertion of amino acids or substitution with other amino acids) and that this hydroxynitrile lyase is retaining its properties derived from nature. In the present invention, the wild-type hydroxynitrile lyase may be (S)-hydroxynitrile lyase or (R)-hydroxynitrile lyase. Preferably, (S)-hydroxynitrile lyase is used. Examples of plants from which the wild-type hydroxynitrile lyase is derived include, but are not limited to, cassava (*Manihot esculenta*), Para rubber tree (*Hevea brasiliensis*), sorghum (*Sorghum bicolor*), almond (*Prunus amygdalus*) and tallow wood (*Ximenia americana*). Among them, cassava or Para rubber tree is preferable. For example, the amino acid sequence of cassava-derived wild-type hydroxynitrile lyase is disclosed in GenBank /EMBL accession number Z29091 and shown in SEQ ID NO: 1. The amino acid sequence of Para rubber tree-derived wild-type hydroxynitrile lyase is disclosed in GenBank/EMBL accession number U40402 and shown in SEQ ID NO: 102.

In the present specification, the cassava-derived wild-type hydroxynitrile lyase is mainly taken as an example to describe the present invention. However, as described above, the source of hydroxynitrile lyase is not particularly limited. Even when a wild-type hydroxynitrile lyase other than the one derived from cassava is used, it is possible to improve hydroxynitrile lyase activity per transformant by applying the site of mutation or the type of amino acid or nucleotide sequence to be mutated disclosed in the present invention. Some wild-type hydroxynitrile lyases have high homology in amino acid sequence though they are derived from different organism species. For example, cassava-derived wild-type hydroxynitrile lyase and Para rubber tree-derived wild-type hydroxynitrile lyase may be enumerated. They have 74% amino acid sequence homology (Japanese Unexamined Patent Publication No. 11-508775). In the present invention, high homology refers to 60% or more homology, preferably 75% or more homology, and particularly preferably 90% or more homology. Even when homology over the full length of amino acid sequence is low, some hydroxynitrile lyases have high similarity in the secondary structure (e.g., the structure or position of α helix or β sheet), tertiary structure or quaternary structure of protein. It is preferable that the wild-type hydroxynitrile lyase used in the present invention derived from an organism other than cassava or Para rubber tree have the above-described homology and similarity.

(II-2) Improved Hydroxynitrile Lyase

The "improved hydroxynitrile lyase" in the present invention is defined as a hydroxynitrile lyase characterized by having a mutation of substitution of at least one amino acid residue in the amino acid sequence of a corresponding wild-type hydroxynitrile lyase with another amino acid mainly using DNA recombination techniques and by its hydroxynitrile lyase activity per transformant being higher than that of the wild-type hydroxynitrile lyase. The "improved hydroxynitrile lyase" is included in the scope of the present invention.

In the present invention, preferably, the "improved hydroxynitrile lyase" has any one of the characteristics described in the following (A) to (G), and yet its hydroxynitrile lyase activity per transformant is higher than the hydroxynitrile lyase activity per transformant into which the corresponding wild-type hydroxynitrile lyase gene is introduced.

(A) an improved hydroxynitrile lyase in which the amino acid residue at position 2 of the amino acid sequence of a wild-type hydroxynitrile lyase is substituted with another amino acid residue;

(B) an improved hydroxynitrile lyase in which the histidine residue at position 103 or a neighboring position thereto of the amino acid sequence of a wild-type hydroxynitrile lyase is substituted with another amino acid residue;

(C) an improved hydroxynitrile lyase in which at least one lysine residue of the amino acid sequence of a wild-type hydroxynitrile lyase is substituted with another amino acid residue;

(D) an improved hydroxynitrile lyase in which the amino acid residue at position 2 and the histidine residue at position 103 or a neighboring position thereto of the amino acid sequence of a wild-type hydroxynitrile lyase are substituted with other amino acid residues;

(E) an improved hydroxynitrile lyase in which the amino acid residue at position 2 and at least one lysine residue of the amino acid sequence of a wild-type hydroxynitrile lyase are substituted with other amino acid residues;

(F) an improved hydroxynitrile lyase in which the histidine residue at position 103 or a neighboring position thereto and at least one lysine residue of the amino acid sequence of a wild-type hydroxynitrile lyase are substituted with other amino acid residues;

(G) an improved hydroxynitrile lyase in which the amino acid residue at position 2, the histidine residue at position 103 or a neighboring position thereto and at least one lysine residue of the amino acid sequence of a wild-type hydroxynitrile lyase are substituted with other amino acid residues.

In (A), (D), (E), or (G) above, the substituent amino acid which replaces the amino acid residue at position 2 (e.g., valine) of a wild-type hydroxynitrile lyase is not particularly limited. Any amino acid other than the one at position 2 of the wild-type hydroxynitrile lyase may be used as long as the activity of the resultant polypeptide after the substitution per transformant becomes higher than the activity of the wild-type hydroxynitrile lyase per transformant. The substituent amino acid which replaces the amino acid residue at position 2 is selected from 19 types of amino acids excluding valine in cassava-derived hydroxynitrile lyase; and selected from 19 types of amino acids excluding alanine in Para rubber tree-derived hydroxynitrile lyase. The substituent amino acid which replaces the amino acid residue at position 2 is preferably lysine, asparagine, isoleucine, arginine, glutamine, proline, threonine, tyrosine, leucine, methionine, serine, glutamic acid, alanine, glycine or aspartic acid; more preferably lysine, asparagine, isoleucine, arginine, glutamine, proline, threonine, tyrosine, leucine, methionine, serine or glutamic acid; still more preferably lysine, asparagine, isoleucine, arginine, glutamine, proline, threonine, tyrosine, leucine, methionine or serine; and particularly preferably lysine, asparagine, isoleucine, arginine or glutamine.

As a finding relating to the stability of proteins in cells, relationship between the amino acid at position 2 and formylmethionine processing or the N-end rule has been reported. The "relationship between the amino acid at position 2 and formylmethionine processing" means that whether or not a protein is ready to undergo processing by methionine aminopeptidase is decided by the type of the amino acid at position 2 of the protein and that the larger the side chains of the amino acid at position 2 are, the more difficult it is for the protein to undergo the processing. The "N-end rule" says that when the N-terminus residue of a protein is arginine, lysine, leucine, phenylalanine, tyrosine, tryptophan or the like, the protein in cells is low in stability and degraded rapidly. According to these relationship or rule, it was considered that there is no significant difference in the stability of proteins when comparing, for example, a protein which has valine at position 2 of SEQ ID NO: 1 and a protein which has isoleucine at position 2 of SEQ ID NO: 1. However, one of the characteristics of the present invention resides in a point that the expression level of a hydroxynitrile lyase is improved by substituting the amino acid at position 2 with another amino acid as described above and, as a result, hydroxynitrile lyase activity per transformant is improved. Therefore, the present invention can not be explained by the existing, above-described relationship or rule. It is believed that the present invention results from a thoroughly new principle.

In (B), (D), (F), or (G) above, the substituent amino acid which replaces the histidine residue at position 103 of a wild-type hydroxynitrile lyase is not particularly limited. Any amino acid other than histidine may be used as long as the activity of the resultant polypeptide after the substitution per transformant becomes higher than the activity of the wild-type hydroxynitrile lyase per transformant. The substituent amino acid which replaces the histidine residue at position 103 is preferably an amino acid having one or both of the following properties (a) and (b):

(a) an amino acid containing one or two nitrogen atoms in its molecule;

(b) a neutral amino acid.

Here, the "amino acid containing one or two nitrogen atoms in its molecule" in (a) refers to, for example, alanine, asparagine, aspartic acid, cysteine, glutamine, glutamic acid, glycine, isoleucine, leucine, lysine, methionine, phenylalanine, proline, serine, threonine, tryptophan, tyrosine or valine. The "neutral amino acid" in (b) refers to an amino acid other than acidic amino acids and basic amino acids. Specific examples of neutral amino acids include methionine, leucine, isoleucine, valine, cysteine, glutamine, serine, threonine, alanine, tryptophan, phenylalanine, asparagine, tyrosine, glycine and proline ("Dictionary of Biochemistry" published by Tokyo Kagaku Dojin). The substituent amino acid which replaces the histidine residue at position 103 is not particularly limited; any amino acid having the above property (a) and/or property (b) may be used. Preferably, methionine, leucine, isoleucine, valine, cysteine, glutamine, serine, threonine, alanine or tryptophan is used. More preferably, methionine, leucine, isoleucine, valine, cysteine or tryptophan is used.

Further, an improved hydroxynitrile lyase in which the histidine residue at a neighboring position to position 103 of the amino acid sequence of a wild-type hydroxynitrile lyase is substituted with another amino acid is also included in the present invention. In wild-type hydroxynitrile lyases not derived from cassava or Para rubber tree, a histidine residue corresponding to the histidine residue at position 103 of cassava or Para rubber tree hydroxynitrile lyase may exist at a neighboring position to position 103. In such a case, the histidine residue existing at a neighboring position to position 103 may be substituted with another amino acid in the same manner as described above.

In the present invention, a histidine residue "at a neighboring position to position 103" means a histidine residue located at a position from 93 to 113, preferably from 98 to 108, and more preferably from 100 to 106.

The position of a histidine residue corresponding to the histidine residue at position 103 of cassava or Para rubber tree hydroxynitrile lyase may be ascertained by, for example, aligning the amino acid sequence of cassava- or Para rubber tree-derived wild-type hydroxynitrile lyase and the amino acid sequence of a hydroxynitrile lyase of interest. Alignment of amino acid sequences may be performed using, for example, ClustalW available from the website of DNA Data Bank of Japan (http://www.ddbj.nig.ac.jp/search/clustalw-j.html).

In (C), (E), (F) or (G) above, the lysine residue to be substituted with another amino acid residue is not particularly limited. Any lysine residue present in the amino acid sequence of the wild-type hydroxynitrile lyase may be selected as long as the activity of the resultant polypeptide after the substitution per transformant becomes higher than the activity of the wild-type hydroxynitrile lyase per transformant. The lysine residue to be substituted with another amino acid residue is preferably at least one lysine residue present in a region from positions 175 to 224 in the amino acid sequence of a wild-type hydroxynitrile lyase. More preferably, one or more residues selected from the lysine residues at positions 176, 199 and 224 in cassava-derived wild-type hydroxynitrile lyase and one or more residues selected from the lysine residues at positions 175, 198 and 223 in Para rubber tree-derived wild-type hydroxynitrile lyase are substituted, respectively.

The substituent amino acids which replace these lysine residues are preferably amino acids having one or both of the following properties (a) and (b):

(a) an amino acid containing one or two nitrogen atoms in its molecule;

(b) a neutral amino acid.

Here, the "amino acid containing one or two nitrogen atoms in its molecule" in (a) is as defined above. The "neutral amino acid" in (b) is as defined above. The most preferable substituent amino acid which replaces these lysine residues is proline.

As preferred embodiments of the improved hydroxynitrile lyases of (A) to (C) above, specifically, the following hydroxynitrile lyases may be enumerated, for example.

(A) An improved hydroxynitrile lyase in which the valine or alanine residue at position 2 of the amino acid sequence of a wild-type hydroxynitrile lyase as shown in SEQ ID NO: 1 or SEQ ID NO: 102 is substituted with any amino acid selected from the group consisting of lysine, asparagine, isoleucine, arginine, glutamine, proline, threonine, tyrosine, leucine, methionine, serine and glutamic acid.

(B) An improved hydroxynitrile lyase in which the histidine residue at position 103 of the amino acid sequence of a wild-type hydroxynitrile lyase as shown in SEQ ID NO: 1 or SEQ ID NO: 102 is substituted with any amino acid selected from the group consisting of methionine, leucine, isoleucine, valine, cysteine, glutamine, serine, threonine, alanine and tryptophan.

(C) An improved hydroxynitrile lyase in which one of the lysine residues at positions 176, 199 and 224, the lysine residues at positions 176 and 199, the lysine residues at positions 176 and 224, the lysine residues at positions 199 and 224, or the lysine residues at positions 176, 199 and 224 in the amino acid sequence of a wild-type hydroxynitrile lyase as shown in SEQ ID NO: 1 are substituted with proline residues; and an improved hydroxynitrile lyase in which one of the lysine residues at positions 175, 198 and 223, the lysine residues at positions 175 and 198, the lysine residues at positions 175 and 223, the lysine residues at positions 198 and 223, or the lysine residues at positions 175, 198 and 223 in the amino acid sequence of a wild-type hydroxynitrile lyase as shown in SEQ ID NO: 102 are substituted with proline residues.

Further, the improved hydroxynitrile lyases of (D) to (G) above are improved hydroxynitrile lyases provided with two or three of the embodiments described in (A) to (C) above. For example, (D) is a combination of (A) and (B), and represents an improved hydroxynitrile lyase in which the valine or alanine residue at position 2 of the amino acid sequence of a wild-type hydroxynitrile lyase as shown in SEQ ID NO: 1 or SEQ ID NO: 102 is substituted with any amino acid selected from the group consisting of lysine, asparagine, isoleucine, arginine, glutamine, proline, threonine, tyrosine, leucine, methionine, serine and glutamic acid, and yet the histidine residue at position 103 thereof is substituted with any amino acid selected from the group consisting of methionine, leucine, isoleucine, valine, cysteine, glutamine, serine, threonine, alanine and tryptophan.

It should be noted here that SEQ ID NO: 1 shows the amino acid sequence of cassava-derived wild-type hydroxynitrile lyase, and SEQ ID NO: 102 shows the amino acid sequence of Para rubber tree-derived wild-type hydroxynitrile lyase.

The present invention also includes an improved hydroxynitrile lyase in which the phenylalanine residue at position 125 in SEQ ID NO: 1 or SEQ ID NO: 102 is substituted with leucine; an improved hydroxynitrile lyase in which the threonine residue at position 205 therein is substituted with serine; or an improved hydroxynitrile lyase in which the asparagine residue at position 235 therein is substituted with glycine.

Further, the improved hydroxynitrile lyase of the present invention includes within its scope a polypeptide which has a characteristic as described in (A) to (G) above (i.e., retaining the embodiment of substitution), which consists of an amino acid sequence having deletion, substitution or addition of one or several (e.g., about 1-10, preferably 1-5) amino acids other than those located at the substitution positions specified in (A) to (G), and whose hydroxynitrile lyase activity per transformant is higher than that of the wild-type hydroxynitrile lyase. Examples of such polypeptides include the following embodiments.

(A) A polypeptide which consists of an amino acid sequence of a wild-type hydroxynitrile lyase wherein the amino acid residue at position 2 is substituted with another amino acid residue, the amino acid sequence further having deletion, substitution or addition of one or several amino acids other than the substituent amino acid at position 2; and yet which has hydroxynitrile lyase activity.

(B) A polypeptide which consists of an amino acid sequence of a wild-type hydroxynitrile lyase wherein the histidine residue at position 103 or a neighboring position thereto is substituted with another amino acid residue, the amino acid sequence further having deletion, substitution or addition of one or several amino acids other than the substituent amino acid at position 103 or a neighboring position thereto; and yet which has hydroxynitrile lyase activity.

(C) A polypeptide which consists of an amino acid sequence of a wild-type hydroxynitrile lyase wherein at least one lysine residue is substituted with another amino acid residue, the amino acid sequence further having deletion, substitution or addition of one or several amino acids other than the substituent amino acid for the lysine residue; and yet which has hydroxynitrile lyase activity.

(D) A polypeptide which consists of an amino acid sequence of a wild-type hydroxynitrile lyase wherein the amino acid residue at position 2 and the histidine residue at position 103 or a neighboring position thereto are substituted with other amino acid residues, the amino acid sequence further having deletion, substitution or addition of one or several amino acids other than the substituent amino acids at position 2 and position 103 or a neighboring position thereto; and yet which has hydroxynitrile lyase activity.

(E) A polypeptide which consists of an amino acid sequence of a wild-type hydroxynitrile lyase wherein the amino acid residue at position 2 and at least one lysine residue are substituted with other amino acid residues, the amino acid sequence further having deletion, substitution or addition of one or several amino acids other than the substituent amino acid at position 2 and the substituent amino acid for the lysine residue; and yet which has hydroxynitrile lyase activity.

(F) A polypeptide which consists of an amino acid sequence of a wild-type hydroxynitrile lyase wherein the histidine residue at position 103 or a neighboring position thereto and at least one lysine residue are substituted with other amino acid residues, the amino acid sequence further having deletion, substitution or addition of one or several amino acids other than the substituent amino acid at position 103 or a neighboring position thereto and the substituent amino acid for the lysine residue; and yet which has hydroxynitrile lyase activity.

(G) A polypeptide which consists of an amino acid sequence of a wild-type hydroxynitrile lyase wherein the amino acid residue at position 2, the histidine residue at position 103 or a neighboring position thereto and at least one lysine residue are substituted with other amino acid residues, the amino acid sequence further having deletion, substitution or addition of one or several amino acids other than the substituent amino acid at position 2, the substituent amino acid at position 103 or a neighboring position thereto and the substituent amino acid for the lysine residue; and yet which has hydroxynitrile lyase activity.

It should be noted that amino acids are sometimes expressed in the commonly used three-letter or one-letter abbreviation codes in the present specification. An alphabet placed before a numerical figure may represent the one-letter abbreviation of the amino acid before substitution, and an alphabet placed after the numerical figure may represent the one-letter abbreviation of the amino acid after substitution. For example, when lysine at position 176 is substituted with proline, an expression "K176P" may be used. This method of expression is applicable to other substitutions.

(III) Hydroxynitrile Lyase Gene (III-1) Wild-Type Hydroxynitrile Lyase Gene

Genetic sequences of some wild-type hydroxynitrile lyases have been elucidated. For example, the genetic sequence for the above-described cassava-derived wild-type hydroxynitrile lyase is shown in SEQ ID NO: 2 (GenBank; accession number Z29091). In the present invention, this is sometimes referred to as the "plant codon wild-type hydroxynitrile lyase gene". Further, the genetic sequence for the above-described Para rubber tree-derived wild-type hydroxynitrile lyase is shown in SEQ ID NO: 103 (GenBank; accession number U40402).

As one example of method for obtaining the plant codon wild-type hydroxynitrile lyase gene, a method may be given which comprises extracting total RNA or mRNA containing the mRNA of the gene from a plant and synthesizing cDNA by conventional methods (see, for example, Molecular Cloning, A Laboratory Manual 2nd ed. (Cold Spring Harbor Press (1989)). Briefly, primers are designed based on known information about the genetic sequence of the plant codon wild-type hydroxynitrile lyase. Then, the gene encoding hydroxynitrile lyase is amplified by PCR using the primers to thereby obtain the plant codon wild-type hydroxynitrile lyase gene. Alternatively, it is also possible to chemically synthesize the full length of the plant codon wild-type hydroxynitrile lyase gene using, for example, PCR with a combination of synthetic oligo-DNAs (assembly PCR) based on known information about the genetic sequence. For example, the plant codon wild-type hydroxynitrile lyase gene is divided into several regions (each consisting of about 50 bp), and a number of oligo-nucleotides having an overlap (e.g., about 20 bp) with the adjacent region at both ends are designed and synthesized. Then, these oligo-nucleotides are annealed with each other by PCR to thereby amplify the plant codon wild-type hydroxynitrile lyase gene.

Recently, it has become possible to produce a protein of interest in a heterologous host using recombinant DNA techniques. It is known that use of those codons frequently used in the host organism improves the expression level of the protein in many cases. As used herein, frequency in the use of codons means the frequency at which codons are used in the process of information conversion from nucleotide sequence to amino acid sequence, and codon means the positioning of three nucleotides in mRNA. In the above-mentioned process of information conversion, the three nucleotides as a unit are translated into one amino acid. Since 64 types of codons correspond to 20 types of amino acids, there is degeneracy in the genetic code and one amino acid has 1 to 6 types of codons which specify the amino acid. For example, valine has 4 codons of GUU, GUC, GUA and GUG When there are a plurality of codons for one amino acid, the organism does not use those codons equally but uses specific codons in a biased manner at ratios characteristic to each organism. Such frequency in the use of codons (codon usage) by each organism is partially stored in databases and can be available from Codon Usage Database (http://www.kazusa.or.jp/codon/).

As used herein, the term "high" in frequency means higher than the lowest frequency when there are a plurality of codons specifying one amino acid, and may not mean the highest frequency. When there is only one codon for one amino acid (e.g., methionine and tryptophan), the codon is used regardless of frequency. However, considering expression efficiency in hosts, it is preferable to use high frequency codons in high expression genes or the highest frequency codons in the host. More specifically, when *E. coli* K12 strain is used as a host, the highest frequency codons (Table 2) may be known from the table of codon usage shown in Table 1. Therefore, when *E. coli* K12 strain is used as a host, codons of a gene of interest to be expressed may be converted to those codons shown in Table 2 using genetic engineering techniques. For example, when the codon used for valine is GTA in the plant codon wild-type hydroxynitrile lyase gene obtained by extracting total RNA or mRNA comprising the mRNA of the gene from cassava and synthesizing cDNA therefrom, as described above, GTA may be converted to GTG which is the highest frequency codon for valine in *E. coli* K12 strain.

The region in which codons are converted may be any region within the coding sequence (CDS). Every codon or a part thereof (at one or several sites) in the CDS may be converted. In the case of the cassava-derived wild-type hydroxynitrile lyase in the present invention, the number of amino acid residues in which codons are converted may be one or more, preferably 1 to 100, more preferably 10 to 70 in the 258 amino acid residues.

A genetic sequence thus composed of codons suitable for the host and encoding the amino acid sequence of a wild-type hydroxynitrile lyase is designated a "host codon wild-type hydroxynitrile lyase gene" in the present invention. When the host is *E. coli*, the gene is sometimes called the "*E. coli* codon wild-type hydroxynitrile lyase gene" and discriminated from the above-described "plant codon wild-type hydroxynitrile lyase gene". When the term "hydroxynitrile lyase gene" is used without the expression of "XXX codon" at the beginning, it is intended that this gene is not limited to plant codon gene or *E. coli* codon gene or it encompasses the both genes.

When the number of codons to be converted is relatively small, the host codon hydroxynitrile lyase gene may be prepared from the plant codon wild-type hydroxynitrile lyase

TABLE 1

Codon Usage in *E. coli* K12 Strain
*Escherichia coli* K12 [gbbct]: 5089 CDS's (1608122 codons)
fields: [triplet] [frequency: per thousand] ([number])

| 1st Nucleotide | | 2nd Nucleotide | | | | | | | | | | | |
|---|---|---|---|---|---|---|---|---|---|---|---|---|---|
| | | U | | | C | | | A | | | G | | |
| U | Phe | UUU | 22.4 (35982) | Ser | UCU | 8.5 (13687) | Tyr | UAU | 16.3 (26266) | Cys | UGU | 5.2 (8340) |
| | | UUC | 16.6 (26678) | | UCC | 8.6 (13849) | | UAC | 12.3 (19728) | | UGC | 6.4 (10347) |
| | | UUA | 13.9 (22376) | | UCA | 7.2 (11511) | termination | UAA | 2.0 (3246) | termination | UGA | 0.9 (1468) |
| | | UUG | 13.7 (22070) | | UCG | 8.9 (14379) | termination | UAG | 0.2 (378) | Trp | UGG | 15.3 (24615) |
| C | Leu | CUU | 11.0 (17754) | Pro | CCU | 7.1 (11340) | His | CAU | 12.9 (20728) | Arg | CGU | 21.0 (33894) |
| | | CUC | 11.0 (17723) | | CCC | 5.5 (8915) | | CAC | 9.7 (15595) | | CGC | 22.0 (35306) |
| | | CUA | 3.9 (6212) | | CCA | 8.5 (13707) | Gln | CAA | 15.4 (24835) | | CGA | 3.6 (5716) |
| | | CUG | 52.7 (84673) | | CCG | 23.2 (37328) | | CAG | 28.8 (46319) | | CGG | 5.4 (8684) |
| A | Ile | AUU | 30.4 (48818) | Thr | ACU | 9.0 (14397) | Asn | AAU | 17.7 (28465) | Ser | AGU | 8.8 (14092) |
| | | AUC | 25.0 (40176) | | ACC | 23.4 (37624) | | AAC | 21.7 (34912) | | AGC | 16.1 (25843) |
| | | AUA | 4.3 (6962) | | ACA | 7.1 (11366) | Lys | AAA | 33.6 (54097) | Arg | AGA | 2.1 (3337) |
| | Met (Initiation) | AUG | 27.7 (44614) | | ACG | 14.4 (23124) | | AAG | 10.2 (16401) | | AGG | 1.2 (1987) |
| G | Val | GUU | 18.4 (29569) | Ala | GCU | 15.4 (24719) | Asp | GAU | 32.2 (51852) | Gly | GGU | 24.9 (40019) |
| | | GUC | 15.2 (24477) | | GCC | 25.5 (40993) | | GAC | 19.0 (30627) | | GGC | 29.4 (47309) |
| | | GUA | 10.9 (17508) | | GCA | 20.3 (32666) | Glu | GAA | 39.5 (63517) | | GGA | 7.9 (12776) |
| | | GUG | 26.2 (42212) | | GCG | 33.6 (53988) | | GAG | 17.7 (28522) | | GGG | 11.6 (17704) |

Coding GC 51.80% 1st letter GC 58.89% 2nd letter GC 40.72% 3rd letter GC 55.79%
Codons expressed in bold letters are frequently used codons in *E. coli*.
This Table is based on http://www.kazusa.orjp/codon/cgi-bin/showcodon.cgi?species=Eschericia+coli+K12+[gbbct] as of Feb. 20, 2004.

TABLE 2

Highest Frequency Codons in *E. coli* K12 Strain

| Amino Acid (three-letter abbreviation) | codon | Amino Acid (three-letter abbreviation) | codon |
|---|---|---|---|
| Ala | GCG | Thr | ACC |
| Val | GUG | Cys | UGC |
| Leu | CUG | Gln | CAG |
| Ile | AUU | Asn | AAC |
| Pro | CCG | Tyr | UAU |
| Phe | UUU | Lys | AAA |
| Trp | UGG | Arg | CGC |
| Met | AUG | His | CAU |
| Gly | GGC | Asp | GAU |
| Ser | AGC | Glu | GAA | gene using the site-directed mutagenesis method described, for example, in Molecular Cloning, A Laboratory Manual 2nd ed., Cold Spring Harbor Laboratory Press (1989) and Current Protocols in Molecular Biology, John Wiley & Sons (1987-1997). Recently, it has become possible to perform site-directed mutagenesis relatively easily using mutagenesis introduction kits such as QuickChange™ Site-Directed Mutagenesis Kit (Stratagene), GeneTailor™ Site-Directed Mutagenesis System (Invitrogen) or TaKaRa Site-Directed Mutagenesis System (e.g., Mutan-K, Mutan-Super Express Km; Takara Bio). Alternatively, it is also possible to synthesize the full length of host codon wild-type hydroxynitrile lyase gene in which a large number of codons are converted to highest frequency codons in the relevant host, by PCR using a combination of synthetic oligo-DNAs (assembly PCR) as described earlier. As an example of *E. coli* codon wild-type hydroxynitrile lyase gene, the *E. coli* codon wild-type hydroxynitrile lyase gene consisting of the nucleotide sequence as shown in SEQ ID NO: 3 described later in Examples may be given.

(III-2) Improved Hydroxynitrile Lyase Gene

The improved hydroxynitrile lyase gene in the present invention means a gene encoding the improved hydroxynitrile lyase enzyme protein described in (II-2) above. The improved hydroxynitrile lyase gene of the present invention include, for example, genes encoding improved hydroxynitrile lyases which have such amino acid substitution mutations as described in (A) to (G) in (II-2) above in the wild-type hydroxynitrile lyase represented by the amino acid sequence of SEQ ID NO: 1 (derived form cassava) or SEQ ID NO: 102 (derived from Para rubber tree). The codons of the wild-type hydroxynitrile lyase which are bases upon which the improved hydroxynitrile lyase gene is prepared may be either plant codons or host codons. Examples of the improved hydroxynitrile lyase gene of the present invention include the following embodiments.

(A)

The sequence as shown in SEQ ID NO: 2 wherein the nucleotides GTA at positions 4 to 6 are substituted with AAA or AAG preferably the nucleotides G and T at positions 4 and 5 are substituted with A and A, respectively (this sequence encodes an improved hydroxynitrile lyase wherein the valine residue at position 2 is substituted with lysine);

The sequence as shown in SEQ ID NO: 2 wherein the nucleotides GTA at positions 4 to 6 are substituted with AAC or AAT, preferably the nucleotides GTA at positions 4 to 6 are substituted with AAC (this sequence encodes an improved hydroxynitrile lyase wherein the valine residue at position 2 is substituted with asparagine);

The sequence as shown in SEQ ID NO: 2 wherein the nucleotides GTA at positions 4 to 6 are substituted with ATA, ATC or ATT, preferably the nucleotides G and A at positions 4 and 6 are substituted with A and C, respectively (this sequence encodes an improved hydroxynitrile lyase wherein the valine residue at position 2 is substituted with isoleucine);

The sequence as shown in SEQ ID NO: 2 wherein the nucleotides GTA at positions 4 to 6 are substituted with AGA, AGG, CGA, CGC, CGG or CGT, preferably the nucleotides GTA at positions 4 to 6 are substituted with CGT (this sequence encodes an improved hydroxynitrile lyase wherein the valine residue at position 2 is substituted with arginine);

The sequence as shown in SEQ ID NO: 2 wherein the nucleotides GTA at positions 4 to 6 are substituted with CAA or CAG, preferably the nucleotides GTA at positions 4 to 6 are substituted with CAG (this sequence encodes an improved hydroxynitrile lyase wherein the valine residue at position 2 is substituted with glutamine);

The sequence as shown in SEQ ID NO: 2 wherein the nucleotides GTA at positions 4 to 6 are substituted with CCA, CCC, CCG or CCT, preferably the nucleotides GTA at positions 4 to 6 are substituted with CCG (this sequence encodes an improved hydroxynitrile lyase wherein the valine residue at position 2 is substituted with proline);

The sequence as shown in SEQ ID NO: 2 wherein the nucleotides GTA at positions 4 to 6 are substituted with ACA, ACC, ACG or ACT, preferably the nucleotides GTA at positions 4 to 6 are substituted with ACC (this sequence encodes an improved hydroxynitrile lyase wherein the valine residue at position 2 is substituted with threonine);

The sequence as shown in SEQ ID NO: 2 wherein the nucleotides GTA at positions 4 to 6 are substituted with TAC or TAT, preferably the nucleotides GTA at positions 4 to 6 are substituted with TAC (this sequence encodes an improved hydroxynitrile lyase wherein the valine residue at position 2 is substituted with tyrosine);

The sequence as shown in SEQ ID NO: 2 wherein the nucleotides GTA at positions 4 to 6 are substituted with TTA, TTG, CTA, CTC, CTG or CTT, preferably the nucleotides G and A at positions 4 and 6 are substituted with C and G, respectively (this sequence encodes an improved hydroxynitrile lyase wherein the valine residue at position 2 is substituted with leucine);

The sequence as shown in SEQ ID NO: 2 wherein the nucleotides GTA at positions 4 to 6 are substituted with ATG, i.e., the nucleotides G and A at positions 4 and 6 are substituted with A and G, respectively (this sequence encodes an improved hydroxynitrile lyase wherein the valine residue at position 2 is substituted with methionine);

The sequence as shown in SEQ ID NO: 2 .wherein the nucleotides GTA at positions 4 to 6 are substituted with AGC, AGT, TCA, TCC, TCG or TCT, preferably the nucleotides GTA at positions 4 to 6 are substituted with AGC (this sequence encodes an improved hydroxynitrile lyase wherein the valine residue at position 2 is substituted with serine);

The sequence as shown in SEQ ID NO: 2 wherein the nucleotides GTA at positions 4 to 6 are substituted with GAA or GAG, preferably the nucleotide T at position 5 is substituted with A (this sequence encodes an improved hydroxynitrile lyase wherein the valine residue at position 2 is substituted with glutamic acid);

The sequence as shown in SEQ ID NO: 2 wherein the nucleotides GTA at positions 4 to 6 are substituted with GCA, GCC, GCG or GCT, preferably the nucleotides T and A at positions 5 and 6 are substituted with C and T, respectively (this sequence encodes an improved hydroxynitrile lyase wherein the valine residue at position 2 is substituted with alanine);

The sequence as shown in SEQ ID NO: 2 wherein the nucleotides GTA at positions 4 to 6 are substituted with GGA, GGC, GGG or GGT, preferably the nucleotides T and A at positions 5 and 6 are substituted with G and C, respectively (this sequence encodes an improved hydroxynitrile lyase wherein the valine residue at position 2 is substituted with glycine);

The sequence as shown in SEQ ID NO: 2 wherein the nucleotides GTA at positions 4 to 6 are substituted with GAC or GAT, preferably the nucleotides T and A at positions 5 and 6 are substituted with A and C, respectively (this sequence encodes an improved hydroxynitrile lyase wherein the valine residue at position 2 is substituted with aspartic acid);

The sequence as shown in SEQ ID NO: 3 wherein the nucleotides GTG at positions 4 to 6 are substituted with AAA or AAG, preferably the nucleotides GTG at positions 4 to 6 are substituted with AAA (this sequence encodes an improved hydroxynitrile lyase wherein the valine residue at position 2 is substituted with lysine);

The sequence as shown in SEQ ID NO: 3 wherein the nucleotides GTG at positions 4 to 6 are substituted with AAC or AAT, preferably the nucleotides GTG at positions 4 to 6 are substituted with AAC (this sequence encodes an improved hydroxynitrile lyase wherein the valine residue at position 2 is substituted with asparagine);

The sequence as shown in SEQ ID NO: 3 wherein the nucleotides GTG at positions 4 to 6 are substituted with ATA, ATC or ATT, preferably the nucleotides G and G at positions 4 and 6 are substituted with A and C, respectively (this sequence encodes an improved hydroxynitrile lyase wherein the valine residue at position 2 is substituted with isoleucine);

The sequence as shown in SEQ ID NO: 3 wherein the nucleotides GTG at positions 4 to 6 are substituted with AGA, AGG, CGA, CGC, CGG or CGT, preferably the nucleotides GTG at positions 4 to 6 are substituted with CGT (this sequence encodes an improved hydroxynitrile lyase wherein the valine residue at position 2 is substituted with arginine);

The sequence as shown in SEQ ID NO: 3 wherein the nucleotides GTG at positions 4 to 6 are substituted with CAA or CAG, preferably the nucleotides G and T at positions 4 and 5 are substituted with C and A, respectively (this sequence encodes an improved hydroxynitrile lyase wherein the valine residue at position 2 is substituted with glutamine);

The sequence as shown in SEQ ID NO: 3 wherein the nucleotides GTG at positions 4 to 6 are substituted with CCA, CCC, CCG or CCT, preferably the nucleotides G and T at positions 4 and 5 are substituted with C and C, respectively (this sequence encodes an improved hydroxynitrile lyase wherein the valine residue at position 2 is substituted with proline);

The sequence as shown in SEQ ID NO: 3 wherein the nucleotides GTG at positions 4 to 6 are substituted with ACA, ACC, ACG or ACT, preferably the nucleotides GTG at positions 4 to 6 are substituted with ACC (this sequence encodes an improved hydroxynitrile lyase wherein the valine residue at position 2 is substituted with threonine);

The sequence as shown in SEQ ID NO: 3 wherein the nucleotides GTG at positions 4 to 6 are substituted with TAC or TAT, preferably the nucleotides GTG at positions 4 to 6 are substituted with TAC (this sequence encodes an improved hydroxynitrile lyase wherein the valine residue at position 2 is substituted with tyrosine);

The sequence as shown in SEQ ID NO: 3 wherein the nucleotides GTG at positions 4 to 6 are substituted with TTA, TTG, CTA, CTC, CTG or CTT, preferably the nucleotide G at position 4 is substituted with C (this sequence encodes an improved hydroxynitrile lyase wherein the valine residue at position 2 is substituted with leucine);

The sequence as shown in SEQ ID NO: 3 wherein the nucleotides GTG at positions 4 to 6 are substituted with ATG, i.e., the nucleotide G at position 4 is substituted with A (this sequence encodes an improved hydroxynitrile lyase wherein the valine residue at position 2 is substituted with methionine);

The sequence as shown in SEQ ID NO: 3 wherein the nucleotides GTG at positions 4 to 6 are substituted with AGC, AGT, TCA, TCC, TCG or TCT, preferably the nucleotides GTG at positions 4 to 6 are substituted with AGC (this sequence encodes an improved hydroxynitrile lyase wherein the valine residue at position 2 is substituted with serine);

The sequence as shown in SEQ ID NO: 3 wherein the nucleotides GTG at positions 4 to 6 are substituted with GAA or GAG, preferably the nucleotides T and G at positions 5 and 6 are substituted with A and A, respectively (this sequence encodes an improved hydroxynitrile lyase wherein the valine residue at position 2 is substituted with glutamic acid);

The sequence as shown in SEQ ID NO: 3 wherein the nucleotides GTG at positions 4 to 6 are substituted with GCA, GCC, GCG or GCT, preferably the nucleotides T and G at positions 5 and 6 are substituted with C and T, respectively (this sequence encodes an improved hydroxynitrile lyase wherein the valine residue at position 2 is substituted with alanine);

The sequence as shown in SEQ ID NO: 3 wherein the nucleotides GTG at positions 4 to 6 are substituted with GGA, GGC, GGG or GGT, preferably the nucleotides T and G at positions 5 and 6 are substituted with G and C, respectively (this sequence encodes an improved hydroxynitrile lyase wherein the valine residue at position 2 is substituted with glycine);

The sequence as shown in SEQ ID NO: 3 wherein the nucleotides GTG at positions 4 to 6 are substituted with GAC or GAT, preferably the nucleotides T and G at positions 5 and 6 are substituted with A and C, respectively (this sequence encodes an improved hydroxynitrile lyase wherein the valine residue at position 2 is substituted with aspartic acid);

The sequence as shown in SEQ ID NO: 103 wherein the nucleotides GCA at positions 4 to 6 are substituted with AAA or AAG, preferably the nucleotides G and C at positions 4 and 5 are substituted with A and A, respectively (this sequence encodes an improved hydroxynitrile lyase wherein the alanine residue at position 2 is substituted with lysine);

The sequence as shown in SEQ ID NO: 103 wherein the nucleotides GCA at positions 4 to 6 are substituted with AAC or AAT, preferably the nucleotides GCA at positions 4 to 6 are substituted with AAC (this sequence encodes an improved hydroxynitrile lyase wherein the alanine residue at position 2 is substituted with asparagine);

The sequence as shown in SEQ ID NO: 103 wherein the nucleotides GCA at positions 4 to 6 are substituted with ATA, ATC or ATT, preferably the nucleotides GCA at positions 4 to 6 are substituted with ATC (this sequence encodes an improved hydroxynitrile lyase wherein the alanine residue at position 2 is substituted with isoleucine);

The sequence as shown in SEQ ID NO: 103 wherein the nucleotides GCA at positions 4 to 6 are substituted with AGA, AGG, CGA, CGC, CGG or CGT, preferably the nucleotides GCA at positions 4 to 6 are substituted with CGT (this sequence encodes an improved hydroxynitrile lyase wherein the alanine residue at position 2 is substituted with arginine);

The sequence as shown in SEQ ID NO: 103 wherein the nucleotides GCA at positions 4 to 6 are substituted with CAA or CAG; preferably the nucleotides GCA at positions 4 to 6 are substituted with CAG (this sequence encodes an improved hydroxynitrile lyase wherein the alanine residue at position 2 is substituted with glutamine);

The sequence as shown in SEQ ID NO: 103 wherein the nucleotides GCA at positions 4 to 6 are substituted with CCA, CCC, CCG or CCT, preferably the nucleotides G and A at positions 4 and 6 are substituted with C and G, respectively (this sequence encodes an improved hydroxynitrile lyase wherein the alanine residue at position 2 is substituted with proline);

The sequence as shown in SEQ ID NO: 103 wherein the nucleotides GCA at positions 4 to 6 are substituted with ACA, ACC, ACG or ACT, preferably the nucleotides G and A at positions 4 and 6 are substituted with A and C, respectively (this sequence encodes an improved hydroxynitrile lyase wherein the alanine residue at position 2 is substituted with threonine);

The sequence as shown in SEQ ID NO: 103 wherein the nucleotides GCA at positions 4 to 6 are substituted with TAC or TAT, preferably the nucleotides GCA at positions 4 to 6 are substituted with TAC (this sequence encodes an improved hydroxynitrile lyase wherein the alanine residue at position 2 is substituted with tyrosine);

The sequence as shown in SEQ ID NO: 103 wherein the nucleotides GCA at positions 4 to 6 are substituted with TTA, TTG, CTA, CTC, CTG or CTT, preferably the nucleotides GCA at positions 4 to 6 are substituted with CTG (this sequence encodes an improved hydroxynitrile lyase wherein the alanine residue at position 2 is substituted with leucine);

The sequence as shown in SEQ ID NO: 103 wherein the nucleotides GCA at positions 4 to 6 are substituted with ATG (this sequence encodes an improved hydroxynitrile lyase wherein the alanine residue at position 2 is substituted with methionine);

The sequence as shown in SEQ ID NO: 103 wherein the nucleotides GCA at positions 4 to 6 are substituted with AGC, AGT, TCA, TCC, TCG or TCT, preferably the nucleotides GCA at positions 4 to 6 are substituted with AGC (this sequence encodes an improved hydroxynitrile lyase wherein the alanine residue at position 2 is substituted with serine);

The sequence as shown in SEQ ID NO: 103 wherein the nucleotides GCA at positions 4 to 6 are substituted with GAA or GAG, preferably the nucleotide C at position 5 is substituted with A (this sequence encodes an improved hydroxynitrile lyase wherein the alanine residue at position 2 is substituted with glutamic acid);

The sequence as shown in SEQ ID NO: 103 wherein the nucleotides GCA at positions 4 to 6 are substituted with GGA, GGC, GGG or GGT, preferably the nucleotides C and A at positions 5 and 6 are substituted with G and C, respectively (this sequence encodes an improved hydroxynitrile lyase wherein the alanine residue at position 2 is substituted with glycine);

The sequence as shown in SEQ ID NO: 103 wherein the nucleotides GCA at positions 4 to 6 are substituted with GAC or GAT, preferably the nucleotides C and A at positions 5 and 6 are substituted with A and C, respectively (this sequence encodes an improved hydroxynitrile lyase wherein the alanine residue at position 2 is substituted with aspartic acid);
(B)

The sequence as shown in SEQ ID NO: 2 or 103 wherein the nucleotides CAC at positions 307 to 309 are substituted with ATG (this sequence encodes an improved hydroxynitrile lyase wherein the histidine residue at position 103 is substituted with methionine);

The sequence as shown in SEQ ID NO: 2 or 103 wherein the nucleotides CAC at positions 307 to 309 are substituted with TTA, TTG, CTA, CTC, CTG or CTT, preferably the nucleotides A and C at positions 308 and 309 are substituted with T and $G_S$ respectively (this sequence encodes an improved hydroxynitrile lyase wherein the histidine residue at position 103 is substituted with leucine);

The sequence as shown in SEQ ID NO: 2 or 103 wherein the nucleotides CAC at positions 307 to 309 are substituted with ATA, ATC or ATT, preferably the nucleotides C and A at positions 307 and 308 are substituted with A and T, respectively (this sequence encodes an improved hydroxynitrile lyase wherein the histidine residue at position 103 is substituted with isoleucine);

The sequence as shown in SEQ ID NO: 2 or 103 wherein the nucleotides CAC at positions 307 to 309 are substituted with GTA, GTC, GTG or GTT, preferably the nucleotides C and A at positions 307 and 308 are substituted with G and T, respectively (this sequence encodes an improved hydroxynitrile lyase wherein the histidine residue at position 103 is substituted with valine);

The sequence as shown in SEQ ID NO: 2 or 103 wherein the nucleotides CAC at positions 307 to 309 are substituted with TGC or TGT, preferably the nucleotides C and A at positions 307 and 308 are substituted with T and G, respectively (this sequence encodes an improved hydroxynitrile lyase wherein the histidine residue at position 103 is substituted with cysteine);

The sequence as shown in SEQ ID NO: 2 or 103 wherein the nucleotides CAC at positions 307 to 309 are substituted with CAA or CAG, preferably the nucleotide C at position 309 is substituted with G (this sequence encodes an improved hydroxynitrile lyase wherein the histidine residue at position 103 is substituted with glutamine);

The sequence as shown in SEQ ID NO: 2 or 103 wherein the nucleotides CAC at positions 307 to 309 are substituted with AGC, AGT, TCA, TCC, TCG or TCT, preferably the nucleotides CAC at positions 307 to 309 are substituted with TCG (this sequence encodes an improved hydroxynitrile lyase wherein the histidine residue at position 103 is substituted with serine);

The sequence as shown in SEQ ID NO: 2 or 103 wherein the nucleotides CAC at positions 307 to 309 are substituted with ACA, ACC, ACG or ACT, preferably the nucleotides CAC at positions 307 to 309 are substituted with ACG (this sequence encodes an improved hydroxynitrile lyase wherein the histidine residue at position 103 is substituted with threonine);

The sequence as shown in SEQ ID NO: 2 or 103 wherein the nucleotides CAC at positions 307 to 309 are substituted with GCA, GCC, GCG or GCT, preferably the nucleotides C and A at positions 307 and 308 are substituted with G and C, respectively (this sequence encodes an improved hydroxynitrile lyase wherein the histidine residue at position 103 is substituted with alanine);

The sequence as shown in SEQ ID NO: 2 or 103 wherein the nucleotides CAC at positions 307 to 309 are substituted with TGG (this sequence encodes an improved hydroxynitrile lyase wherein the histidine residue at position 103 is substituted with tryptophan);

The sequence as shown in SEQ ID NO: 3 wherein the nucleotides CAT at positions 307 to 309 are substituted with ATG (this sequence encodes an improved hydroxynitrile lyase wherein the histidine residue at position 103 is substituted with methionine);

The sequence as shown in SEQ ID NO: 3 wherein the nucleotides CAT at positions 307 to 309 are substituted with TTA, TTG, CTA, CTC, CTG or CTT, preferably the nucleotides A and T at positions 308 and 309 are substituted with T and C, respectively (this sequence encodes an improved hydroxynitrile lyase wherein the histidine residue at position 103 is substituted with leucine);

The sequence as shown in SEQ ID NO: 3 wherein the nucleotides CAT at positions 307 to 309 are substituted with ATA, ATC or ATT, preferably the nucleotides CAT at positions 307 to 309 are substituted with ATC (this sequence encodes an improved hydroxynitrile lyase wherein the histidine residue at position 103 is substituted with isoleucine);

The sequence as shown in SEQ ID NO: 3 wherein the nucleotides CAT at positions 307 to 309 are substituted with GTA, GTC, GTG or GTT, preferably the nucleotides CAT at positions 307 to 309 are substituted with GTC (this sequence encodes an improved hydroxynitrile lyase wherein the histidine residue at position 103 is substituted with valine);

The sequence as shown in SEQ ID NO: 3 wherein the nucleotides CAT at positions 307 to 309 are substituted with TGC or TGT, preferably the nucleotides C and A at positions 307 and 308 are substituted with T and G, respectively (this sequence encodes an improved hydroxynitrile lyase wherein the histidine residue at position 103 is substituted with cysteine);

The sequence as shown in SEQ ID NO: 3 wherein the nucleotides CAT at positions 307 to 309 are substituted with CAA or CAG, preferably the nucleotide T at positions 309 is substituted with G (this sequence encodes an improved hydroxynitrile lyase wherein the histidine residue at position 103 is substituted with glutamine);

The sequence as shown in SEQ ID NO: 3 wherein the nucleotides CAT at positions 307 to 309 are substituted with AGC, AGT, TCA, TCC, TCG or TCT, preferably the nucleotides CAT at positions 307 to 309 are substituted with AGC (this sequence encodes an improved hydroxynitrile lyase wherein the histidine residue at position 103 is substituted with serine);

The sequence as shown in SEQ ID NO: 3 wherein the nucleotides CAT at positions 307 to 309 are substituted with ACA, ACC, ACG or ACT, preferably the nucleotides CAT at positions 307 to 309 are substituted with ACC (this sequence encodes an improved hydroxynitrile lyase wherein the histidine residue at position 103 is substituted with threonine);

The sequence as shown in SEQ ID NO: 3 wherein the nucleotides CAT at positions 307 to 309 are substituted with GCA, GCC, GCG or GCT, preferably the nucleotides CAT at positions 307 to 309 are substituted with GCC (this sequence encodes an improved hydroxynitrile lyase wherein the histidine residue at position 103 is substituted with alanine);

The sequence as shown in SEQ ID NO: 3 wherein the nucleotides CAT at positions 307 to 309 are substituted with TGG (this sequence encodes an improved hydroxynitrile lyase wherein the histidine residue at position 103 is substituted with tryptophan).

It should be noted here that the improved hydroxynitrile lyase gene of the present invention also includes genes encoding improved hydroxynitrile lyases in which a histidine residue at a neighboring position to position 103 is substituted with another amino acid as described in (II-2) above (i.e., improved hydroxynitrile lyases in which the histidine residue corresponding to the histidine residue at position 103 of cassava- or Para rubber tree-derived hydroxynitrile lyase is mutated).

(C)

The sequence as shown in SEQ ID NO: 2 wherein the nucleotides AAG at positions 526 to 528 are substituted with CCA, CCC, CCG or CCT, preferably the nucleotides AAG at positions 526 to 528 are substituted with CCC (this sequence encodes an improved hydroxynitrile lyase wherein the lysine residue at position 176 is substituted with proline);

The sequence as shown in SEQ ID NO: 2 wherein the nucleotides AAG at positions 595 to 597 are substituted with CCA, CCC, CCG or CCT, preferably the nucleotides AAG at positions 595 to 597 are substituted with CCC (this sequence encodes an improved hydroxynitrile lyase wherein the lysine residue at position 199 is substituted with proline);

The sequence as shown in SEQ 1D NO: 2 wherein the nucleotides AAA at positions 670 to 672 are substituted with CCA, CCC, CCG or CCT, preferably the nucleotides AAA at positions 670 to 672 are substituted with CCC (this sequence encodes an improved hydroxynitrile lyase wherein the lysine residue at position 224 is substituted with proline);

The sequence as shown in SEQ ID NO: 3 wherein the nucleotides AAA at positions 526 to 528 are substituted with CCA, CCC, CCG or CCT, preferably the nucleotides AAA at positions 526 to 528 are substituted with CCC (this sequence encodes an improved hydroxynitrile lyase wherein the lysine residue at position 176 is substituted with proline);

The sequence as shown in SEQ ID NO: 3 wherein the nucleotides AAA at positions 595 to 597 are substituted with CCA, CCC, CCG or CCT, preferably the nucleotides AAA at positions 595 to 597 are substituted with CCC (this sequence encodes an improved hydroxynitrile lyase wherein the lysine residue at position 199 is substituted with proline);

The sequence as shown in SEQ ID NO: 3 wherein the nucleotides AAA at positions 670 to 672 are substituted with CCA, CCC, CCG or CCT, preferably the nucleotides AAA at positions 670 to 672 are substituted with CCT (this sequence encodes an improved hydroxynitrile lyase wherein the lysine residue at position 224 is substituted with proline);

The sequence as shown in SEQ ID NO: 103 wherein the nucleotides AAG at positions 523 to 525 are substituted with CCA, CCC, CCG or CCT, preferably the nucleotides AAG at positions 523 to 525 are substituted with CCC (this sequence encodes an improved hydroxynitrile lyase wherein the lysine residue at position 175 is substituted with proline);

The sequence as shown in SEQ ID NO: 103 wherein the nucleotides AAG at positions 592 to 594 are substituted with CCA, CCC, CCG or CCT, preferably the nucleotides AAG at positions 592 to 594 are substituted with CCC (this sequence encodes an improved hydroxynitrile lyase wherein the lysine residue at position 198 is substituted with proline);

The sequence as shown in SEQ ID NO: 103 wherein the nucleotides AAA at positions 667 to 669 are substituted with CCA, CCC, CCG or CCT, preferably the nucleotides AAA at positions 667 to 669 are substituted with CCT (this sequence encodes an improved hydroxynitrile lyase wherein the lysine residue at position 223 is substituted with proline).

The improved hydroxynitrile lyase genes of (D) to (G) are improved hydroxynitrile lyase genes which have any two or all three of the embodiments described in (A) to (C) above.

For example, (D) is a combination of (A) and (B). Thus, as one example of the gene of (D), a gene may be given which is an improved hydroxynitrile lyase gene having the sequence as shown in SEQ ID NO: 2 wherein the nucleotides G and T at positions 4 and 5 are substituted with A and A, respectively, and the nucleotide CAC at positions 307 to 309 are substituted with ATG.

Further, the improved hydroxynitrile lyase gene of the present invention may also have any of the following substitutions in addition to the embodiments described in (A) to (G) above.

The sequence as shown in SEQ ID NO: 2 wherein the nucleotides TTT at positions 373 to 375 are substituted with CTT (this sequence encodes an improved hydroxynitrile lyase wherein the phenylalanine residue at position 125 is substituted with leucine);

The sequence as shown in SEQ ID NO: 2 wherein the nucleotides ACC at positions 436 to 438 are substituted with ACA;

The sequence as shown in SEQ ID NO: 2 wherein the nucleotides ACC at positions 613 to 615 are substituted with TCC (this sequence encodes an improved hydroxynitrile lyase wherein the phenylalanine residue at position 205 is substituted with leucine); or The sequence as shown in SEQ ID NO: 2 wherein the nucleotides GAT at positions 703 to 705 are substituted with GGT (this sequence encodes an improved hydroxynitrile lyase wherein the aspartic acid residue at position 235 is substituted with glycine).

Further, the improved hydroxynitrile lyase gene of the present invention also includes a DNA which hybridizes to a DNA consisting of a nucleotide sequence complementary to the nucleotide sequence described in any one of (A) to (G) above under stringent conditions, and encodes a protein whose hydroxynitrile lyase activity per transformant is higher than that of the corresponding wild-type hydroxynitrile lyase. Such a DNA may be obtained from a cDNA library or genomic library by a known hybridization method, such as colony hybridization, plaque hybridization or Southern blotting, using as a probe an improved hydroxynitrile lyase gene DNA consisting of the nucleotide sequence described in any one of (A) to (G) above or a complementary sequence thereto, or a fragment thereof. The library may be one prepared by a known method. Alternatively, a commercial cDNA library or genomic library may also be used.

The term "stringent conditions" refers to conditions at the time of washing after hybridization. Specifically, it means conditions where salt concentration is 300-2000 mM and temperature is 40-75° C., preferably salt concentration is 600-900 mM and temperature is 65° C. Specific example of stringent conditions includes 2×SSC and 50° C. One of ordinary skill in the art can appropriately select the salt concentration and temperature of the buffer, and other conditions such as the concentration and length of the probe, reaction time, etc. to thereby decide conditions for obtaining a DNA encoding the improved hydroxynitrile lyase of the present invention.

Detailed procedures of hybridization methods are described, for example, in Molecular Cloning, A Laboratory Manual 2nd ed. (Cold Spring Harbor Laboratory Press (1989)). As an example of the above DNA which hybridizes, a DNA comprising a nucleotide sequence having 40% or more, preferably 60% or more, more preferably 90% or more identity with the nucleotide sequence as described in any one of (A) to (G) above or a partial fragment thereof may be given.

In the present invention, the method for preparing the improved hydroxynitrile lyase gene may be any of known methods for introducing mutations. Usually, the improved hydroxynitrile lyase gene may be prepared by a known method. For example, a method in which a site-directed substitution is introduced into a wild-type hydroxynitrile lyase gene using a commercial kit; a method in which a genetic DNA is selectively cleaved and then selected oligonucleotides are removed/added and ligated; or the like may be enumerated.

These site-directed mutagenesis methods are described, for example, in Molecular Cloning, A Laboratory Manual 2nd ed. (Cold Spring Harbor Press (1989)); Current Protocols in Molecular Biology (John Wiley & Sons (1987-1997)); Kunkel, Proc. Natl. Acad. Sci. USA 82: 488-92 (1985); Kramer and Fritz, Method. Enzymol. 154:350-67(1987); Kunkel, Method. Enzymol. 85: 2763-6 (1988). Recently, mutagenesis introduction kits utilizing site-directed mutagenesis based on the Kunkel method or the gapped duplex method may be used to perform mutagenesis. Examples of such kits include QuickChange™ Site-Directed Mutagenesis Kit (Stratagene), GeneTailor™ Site-Directed Mutagenesis System (Invitrogen) and TaKaRa Site-Directed Mutagenesis System (e.g., Mutan-K, Mutan-Super Express Km; Takara Bio). When a site into which a mutation of interest is to be introduced is located near a restriction enzyme site (where digestion and ligation are easy) in the target gene sequence, a genetic DNA fragment introduced the mutation of interest may be obtained easily by performing PCR using primers (synthetic oligo-DNAs) into which the mutation of interest is introduced. Alternatively, improved hydroxyl nitrile lyase genes may be obtained as a synthetic gene by PCR elongation with a combination of synthetic oligo-DNAs (assembly PCR).

It is also possible to obtain improved hydroxynitrile lyase genes from wild-type hydroxynitrile lyase genes by random mutation introduction methods, e.g., contacting/reacting mutagens such as hydroxylamine or nitrous acid; mutagenize by UV irradiation; introducing random mutations by PCR (polymerase chain reaction), etc.

(IV) Recombinant Vector and Transformant (IV-1) Recombinant Vector

In order to express the thus obtained improved hydroxynitrile lyase gene of the present invention in a host, an expression cassette into wich a transcription promoter upstream of the gene and a terminator downstream of the gene are inserted may be constructed and inserted into an expression vector. Alternatively, when an expression vector into which the improved hydroxynitrile lyase gene is to be introduced already has a transcription promoter and a terminator, the mutated gene may be inserted between the promoter ant the terminator without construction of an expression cassette. For introduction of the improved hydroxynitrile lyase gene into a vector, such methods as using restriction enzymes or a topoisomerase may be used. If necessary for the introduction, an appropriate linker may be added. In the present invention, it is also possible to perform such integrating operations concurrently with operations for preparing the improved hydroxynitrile lyase gene. Briefly, using primers which have a nucleotide sequence substituted with another nucleotide sequence to encode other amino acids and, as a template, a recombinant vector into which the wild-type hydroxynitrile lyase gene has been cloned, PCR may be performed and the resultant amplified product may be integrated into a vector.

The type of promoter is not particularly limited as long as it allows appropriate expression of the gene of interest in a host. Specific examples of promoters useful in the present invention include, but are not limited to, *E. coli*-derived tryptophan operon (trp) promoter and lactose operon (lac) promoter; lambda phage-derived PL promoter and PR promoter; *Bacillus subtilis*-derived gluconate synthase promoter (gnt), alkali protease promoter (apr), neutral protease promoter (npr) and α-amylase promoter (amy). Modified and designed sequences such as tac promoter and trc promoter may also be used.

Terminators are not necessarily needed, and the type thereof is not particularly limited. For example, ρ factor non-dependent terminators such as lipoprotein terminator, trp operon terminator or rrnB terminator may be used.

As important nucleotide sequences for translation into amino acids, ribosome binding sequences such as SD sequence and Kozak sequence are known. These sequences may be inserted upstream of the mutated gene. When a prokaryote is used as a host, SD sequence may be added by PCR or the like. When a eukaryote is used as a host, Kozak sequence may be added. Examples of SD sequence include *E. coli*-derived or *B. subtilis*-derived sequences. However, any SD sequence may be used as long as it functions in a desired host such as *E. coli* or *B. subtilis*. For example, a consensus sequence consisting of 4 or more consecutive nucleotides complementary to a 3' terminal region of 16S ribosome RNA may be synthesized by DNA synthesis and used.

Generally, vectors comprise an element to select a transformant of interest (selective marker). Specific examples of selective markers include, but are not limited to, drug resistance genes, auxotrophic complementary genes and genes that render assimilability, and they are appropriately selected considering the purpose or the host to be used. For example, specific examples of drug resistance genes used as selective marker in *E. coli* include ampicillin resistance gene, kanamycin resistance gene, dihydrofolate reductase gene, and neomycin resistance gene.

The vector to be used in the present invention is not particularly limited as long as it retains the above-described mutated gene. A vector suitable for each host may be used. Specific examples of vectors useful in the present invention include plasmid DNA, bacteriophages DNA, retrotransposon DNA and artificial chromosomal DNA. For example, when *E. coli* is used as a host, a vector comprising a region capable of autonomous replication in *E. coli*, such as pTrc99A (Centraalbureau voor Schimmelcultures (CBS), Netherland; http://www.cbs.knaw.nl/), pUC19 (Takara Bio; Japan), pKK233-2 (Centraalbureau voor Schimmelcultures (CBS), Netherland; http://www.cbs.knaw.nl/), pET-12 (Novagen; Germany) or pET-26b (Novagen; Germany) may be used. If necessary, a vector modified from these vectors may be used. It is also possible to use an expression vector with high expression efficiency (such as pTrc99A or pKK233-2 having trc promoter and lac operator) may be used.

A recombinant vector comprising the above-described improved hydroxynitrile lyase gene is included within the scope of the present invention.

(IV-1) Transformant

Transformants or transductants (sometimes, these are collectively referred to as the "transformant") may be prepared by transforming or transducing the recombinant vector of the present invention into a host. The transformant is also included in the scope of the present invention.

The host to be used in the present invention is not particularly limited as long as it is capable of expressing an improved hydroxynitrile lyase of interest upon introduction of the above-described recombinant vector. Specific examples of hosts to be used in the present invention include, but are not limited to, bacteria such as *Escherichia coli* and *Bacillus subtilis*, yeasts (*Pichia, Saccharomyces*), fungi (*Aspergillus*), animal cells, insect cells and plant cells.

When a bacterium is used as a host, especially preferable in the present invention is *E. coli*. Examples of *E. coli* strains to be used in the present invention include, but are not limited to, K12 strain and B strain, and derivatives from these wild-type strains, such as JM109 strain, XL1-Blue strain and C600 strain. Especially when a lactose operon (lac) promoter mentioned above or a derivative promoter therefrom is used as an expression promoter, expression of a gene of interest becomes inducible by IPTG or the like in a host with lacI repressor gene; and expression of a gene of interest becomes permanent in a host without lacI repressor gene. So, a convenient host may be selected. These strains are easily available, for example, from American Type Culture Collection (ATCC). As a bacillus, *Bacillus subtilis* may be used, for example. The method for introducing a recombinant vector into the bacterium is not particularly limited. Any method of DNA transfer into bacteria may be used, e.g., the method using calcium ion or electroporation.

When a yeast is used as a host, *Saccharomyces cerevisiae*, *Schizosaccharomyces pombe*, *Pichia pastoris* or the like may be used. The method for introducing a recombinant vector into the yeast is not particularly limited. Any method of DNA transfer into yeasts may be used, e.g., electroporation, the spheroplast method, and the lithium acetate method.

When an animal cell is used as a host, simian COS-7 cells, Vero cells, CHO cells, mouse L cells, rat GH3 cells, human FL cells or the like may be used. As the method for introducing a recombinant vector into the animal cell, electroporation, the calcium phosphate method or lipofection may be used, for example.

When an insect cell is used as a host, Sf9 cells, Sf21 cells or the like may be used. As the method for introducing a recombinant vector into the insect cell, the calcium phosphate method, lipofection or electroporation may be used, for example.

When a plant cell is used as a host, cells to be used in the present invention include, but are not limited to, tobacco BY-2 cells. As the method for introducing a recombinant vector to the plant cell, the agrobacterium method, the particle gun method, the PEG method or electroporation may be used, for example.

(V) Method for Preparing Culture and Improved Hydroxynitrile Lyase

In the present invention, an improved hydroxynitrile lyase may be prepared by culturing the above-described transformant and recovering the improved hydroxynitrile lyase from the resultant culture.

The present invention also includes a method for producing an improved hydroxynitrile lyase, characterized by recovering the improved hydroxynitrile lyase from the culture.

In the present invention, the term "culture" means any of the following materials: culture supernatant, cultured cells, cultured microorganisms, or disrupted materials from cells or microorganisms. The culture obtained by culturing the transformant of the present invention is included in the scope of the present invention.

Cultivation of the transformant of the present invention is carried out in accordance with conventional methods commonly used for culturing hosts. The improved hydroxynitrile lyase of interest is accumulated in the above-described culture.

As a medium to culture the transformant of the present invention, either a natural or synthetic medium may be used as long as it contains carbon sources, nitrogen sources, inorganic salts, etc. assimilable by the host and is capable of efficient culture of the transformant. As carbon sources, carbohydrates such as glucose, galactose, fructose, sucrose, raffinose and starches; organic acids such as acetic acid and propionic acid; and alcohols such as ethanol and propanol may be enumerated. As nitrogen sources, ammonia; ammonium salts of inorganic or organic acids such as ammonium chloride, ammonium sulfate, ammonium acetate and ammonium phosphate; and other nitrogen-containing compounds may be enumerated. Further, peptone, yeast extract, meat extract, corn steep liquor, and various amino acids may also be used. As inorganic substances, potassium dihydrogenphosphate, dipotassium hydrogenphosphate, magnesium phosphate, magnesium sulfate, sodium chloride, iron(III) sulfate, manganese sulfate, zinc sulfate, copper sulfate, calcium carbonate and the like may be enumerated. If necessary, defoaming agents may be added to prevent foaming during cultivation. Vitamins or the like may also be added optionally. If necessary, antibiotics such as ampicillin or tetracycline may be added during cultivation.

The cultivation may be performed under selective pressure in order to prevent the falling off of the vector and the gene of interest. Briefly, when the selective marker is a drug resistance gene, the relevant drug may be added to the medium; and when the selective marker is an auxotrophic complementary gene, the relevant nutritional factor may be removed from the medium. Further, when the selective marker is a gene that renders assimilability, the relevant assimilation factor may be added as the sole factor, if necessary. For example, when *E. coli* transformed with a vector comprising an ampicillin resistance gene is cultured, ampicillin may be added to the medium during cultivation, if necessary.

When a transformant transformed with an expression vector having an inducible promoter is cultured, an inducer may be added to the medium, if necessary. For example, when a transformant transformed with an expression vector having a promoter inducible by isopropyl-β-D-thiogalactoside (IPTG), IPTG or the like may be added to the medium. When a transformant transformed with an expression vector having a trp promoter inducible by indoleacetic acid (IAA), IAA or the like may be added to the medium.

Cultivation conditions for transformants are not particularly limited. Any conditions may be used as long as they do not inhibit the productivity of the improved hydroxynitrile lyase of interest and the growth of the host. Usually, cultivation temperature is 10-45° C., preferably 10-40° C., more preferably 15-40° C., and still more preferably 20-37° C. If necessary, the temperature may be changed during cultivation. Time of cultivation is 5-120 hours, preferably 5-100 hours, more preferably 10-100 hours, and still more preferably 15-80 hours. Adjustment of pH is performed with an inorganic or organic acid or an alkali solution. When the transformant is *E. coli*, pH is adjusted to 6-9. Examples of cultivation methods include solid culture, stationary culture, shaking culture and aeration-agitation culture.

Especially when *E. coli* transformants are cultured, it is preferable to culture the transformants under aerobic conditions by shaking culture or aeration-agitation culture (in a jar fermenter). Although *E. coli* transformants may be cultured by conventional solid culture, it is strongly recommended to employ liquid culture for them. As a medium to culture *E. coli* transformants, a medium containing one or more nitrogen sources such as yeast extract, tryptone, polypeptone, corn steep liquor, a decoction of soybean or wheat bran; supplemented with one or more inorganic salts such as sodium chloride, potassium dihydrogenphosphate, dipotassium hydrogenphosphate, magnesium sulfate, magnesium, chloride, iron(III) chloride, iron(III) sulfate or manganese sulfate; and optionally supplemented with carbohydrate materials, vitamins or the like; may be used. It is appropriate to adjust the initial pH of the medium to 7-9. The culture is performed at 5-40° C., preferably at 10-37° C., for 5-100 hours. Preferably, aeration-agitation submerged culture, shaking culture, stationary culture, feeding culture or the like is used. Especially when an improved hydroxynitrile lyase is produced in an industrial scale, aeration-agitation culture may be used. Operational method for aeration-agitation culture is not particularly limited. Any of batch culture, fed-batch culture (semi-batch culture) or continuous culture may be used. In particular, when enhancement of productivity per apparatus, time, cost or operation is intended by high density culture, fed-batch culture may be used. The composition of fed medium used in fed-batch culture may be the same as that of the initial (batch) medium. Alternatively, the composition may be altered but it is preferable that the medium component concentrations are higher than those in the initial medium. The volume of fed medium is not particularly limited. Usually, ½ or less volume relative to the initial medium may be added. Examples of the feeding mode for fed medium include, but are not limited to, constant feeding, exponential feeding, stepwise increase feeding, specific growth-rate control feeding, pH-stat feeding, DO-stat feeding, glucose concentration control feeding, acetate concentration monitoring feeding, and fuzzy neural network feeding (Trends in Biotechnology (1996), 14, 98-105). Any of these feeding modes may be used as long as a desired hydroxynitrile lyase productivity is achieved. When fed-batch culture is practiced, the time of culture termination is not necessarily limited to the time when addition of fed medium has been completed. If necessary, culture may be continued further and stopped at the time when hydroxynitrile lyase activity per transformant is the highest.

As a medium to culture a transformant obtained from an animal cell as a host, commonly used RPMI1640 medium, DMEM medium or one of these medium supplemented with fetal bovine serum, etc. may be used. Usually, cultivation is performed under 5% $CO_2$ at 37° C. for 1 to 30 days. During cultivation, antibiotics such as kanamycin or penicillin may be added to the medium, if necessary. When the transformant (or transductant) is a plant cell or plant tissue, cultivation may be performed using a conventional plant cell culture medium such as MS basal medium or LS basal medium. The culture method may be either conventional solid culture or liquid culture.

When the transformant is a plant cell or plant tissue, cultivation may be performed using a conventional plant cell culture medium such as MS basal medium or LS basal medium. The culture method may be either conventional solid culture or liquid culture.

By culturing the transformant under the conditions as described above, it is possible to allow accumulation of the improved hydroxynitrile lyase of the present invention in the resultant culture, that is, any of the following materials: culture supernatant, cultured cells, cultured microorganisms, or disrupted cells or microorganisms.

When the improved hydroxynitrile lyase is produced in microorganisms or cells, the improved hydroxynitrile lyase of interest may be recovered by disrupting microorganisms or cells after cultivation.

Before disruption, if necessary, solid-liquid separation operations such as centrifugation or membrane filtration may be performed for medium removal and washing.

Centrifuge is not particularly limited as long as it can provide a centrifugal force to precipitate microorganisms or cells. A cylinder type or disc-stack type centrifuge may be used. As the centrifugal force, 500 G-20,000 G may be used.

The membrane which may be used in this process may be either a microfiltration (MF) membrane or ultrafiltration (UF) membrane as long as it can achieve the intended solid-liquid separation. Usually, it is preferable to use a microfiltration (MF) membrane. Microfiltration may be classified into dead-end mode or cross-flow (tangential flow) mode based on the direction of flow; into weight mode, pressure mode, vacuum mode and centrifugal mode based on the addition of pressure; and into rotary mode and continuous mode based on the operational method. Any of these modes may be used as long as solid-liquid separation can be achieved. The materials of MF membrane may be roughly divided into polymer, ceramic, metal and a combination thereof. The material is not particularly limited provided that it does not decrease the activity of improved hydroxynitrile lyase and the recovery ratio of that activity at the time of solid-liquid separation. Preferably, a polymer membrane made of polysulfone, polyethersulfone, polytetrafluoroethylene, polyvinylidine fluoride, polyvinyl chloride, polypropylene, polyolefin, polyethylene, polycarbonate, polyacrylonitrile, mixed cellulose ester, cuprammonium regenerated cellulose ester, polyimide, nylon, teflon or the like may be used. With respect to the pore size of membrane, any size which is capable of capturing microorganisms or cells and capable of concentration operation may be used. Usually, the pore size may be around 0.1-0.5 μm.

In the present invention, the term "activity recovery ratio" means the relative ratio (%) of the activity recovered after an operation such as solid-liquid separation, taking the activity before the operation as 100%.

At the time of solid-liquid separation by centrifugation and membrane filtration, water, buffer or isotonic solution may be added to perform dilution washing, if necessary. The buffer used for this purpose is not particularly limited provided that it does not decrease the activity of improved hydroxynitrile lyase and the activity recovery ratio thereof at solid-liquid separation. For example, a buffer whose salt concentration is 5-500 mM, preferably about 5-150 mM and pH is about 4-8 may be used. As components of the buffer, salts including phosphoric acid salts, citric acid salts and acetic acid salts of sodium or potassium may be enumerated. Specific examples of buffers include 5 mM potassium phosphate buffer (pH 6-7)

and 20 mM sodium acetate buffer (pH 5-6). As the isotonic solution, 0.7-0.9% sodium chloride solution may be used, for example. Further, substances capable of stabilizing the improved hydroxynitrile lyase (e.g., flavonoids) may be added (Food Technology and Biotechnology (2001), 39(3), 161-167).

As the method for disrupting microorganisms or cells, sonication, high pressure treatment with a French press or homogenizer, grinding treatment with a bead mill, collision treatment with an impact crusher, enzymatic treatment using such as lysozyme, cellulase or pectinase, freeze-thaw treatment, treatment with a hypotonic solution, cell lysis induction by phage, etc. may be enumerated. Any of these methods may be used alone or in combination. When microorganisms or cells are disrupted in an industrial scale, use of high pressure treatment, grinding treatment or collision treatment is preferable from the viewpoints of easiness in operation, recovery ratio and cost. Occasionally, these physical crushing operations may be combined with enzymatic treatment. Operational conditions for individual disrupting methods are not particularly limited provided that the recovery ratio of improved hydroxynitrile lyase from microorganisms or cells is sufficiently high. The "sufficiently high recovery ratio of improved hydroxynitrile lyase" means preferably 85% or more, more preferably 90% or more, still more preferably 95%, and most preferably 99% or more.

When grinding treatment is performed with a bead mill, for example, beads 2.5-6.0 g/cm$^3$ in density and 0.1-1.0 mm in size may be packed in the mill at about 80-85%. Either batch method or continuous method may be used for the operation. The concentration of microorganisms or cells is not particularly limited. For example, the concentration may be about 6-12% for a bacterium and about 14-18% for a yeast.

When high pressure treatment is performed, the pressure to be added is not particularly limited provided that the recovery ratio of improved hydroxynitrile lyase from microorganisms or cells is sufficiently high. For example, crushing may be performed with a pressure of about 40-150 MPa. The concentration of microorganisms or cells is not particularly limited. For example, the concentration may be about 20% or less. If necessary, multi-stage treatment may be performed by connecting apparatuses in series or using an apparatus with multi-stage structure, to thereby improve the efficiency of crushing and operation. Usually, a temperature increase of 2-3° C. per 10 MPa of pressure occurs. So, it is preferable to perform cooling treatment when necessary.

When collision treatment is performed, microorganisms or a cell slurry to be crushed are subjected to spray rapid freezing or the like (freezing rate: e.g., several thousand ° C./min) to obtain frozen microparticles (e.g., 50 μm or less), which are then stroked against a collision board by means of a high speed (e.g., 300 m/sec) carrier gas. Thus, microorganisms or cells are crushed.

As a result of the above-described disrupting treatment for microorganisms or cells, intracellular nucleic acid flows out, which increases the viscosity of the treated liquid and may results in difficulty in handling it. In such a case, or when improvement of activity recovery ratio can be expected in a later step of residue separation, nucleic acid removal or degradation may be performed to decrease the viscosity of the treated liquid or to improve the activity recovery ratio in the step of residue separation, if necessary. As the method for removing or degrading the nucleic acid in the liquid containing disrupted cells, any method may be used provided as long as it is capable of removing or degrading nucleic acid without decreasing the activity of improved hydroxynitrile lyase or the recovery ratio of the activity. For example, as described on pages 200-201 in Biochemistry Experiment Course Vol. 5, a method in which protamine sulfate or streptomycin is added to the liquid containing disrupted cells to precipitate nucleic acid; a method in which nucleic acid is degraded with a nuclease; a method in which liquid-liquid separation is performed with dextran-polyethylene glycol; or the like may be enumerated. It may also be effective to add a physical crushing treatment further. Of these methods, the method of degradation using a nuclease may be employed when rapid degradation of nucleic acid is desired while avoiding complication of steps. The nuclease to be used in the nucleic acid degradation treatment may be any nuclease as long as it acts on at least deoxyribonucleic acid (DNA), has the ability to catalyze nucleic acid degradation and reduces the degree of DNA polymerization. It may be possible to utilize a nuclease inherent within the transformant cell. Alternatively, it is possible to add an exogenous nuclease. Examples of the exogenous nuclease to be added include bovine spleen-derived DNase I (Takara Bio, Japan), porcine spleen-derived DNase II (Wako Purechemical, Japan), *Serratia marcescens*-derived Benzonase® Nuclease (Takara Bio, Japan) and *Staphylococcus aureus*-derived nuclease (Wako Purechemical, Japan). The amount of enzyme to be added varies depending on the type of nuclease and the definition of unit (U), but one of ordinary skill in the art can select appropriately. If necessary, cofactors such as magnesium required for the nuclease may be added. The treatment temperature varies depending on the type of nuclease. When the nuclease is derived from a mesophilic organism, temperatures ranging from 20 to 40° C. may be use, for example.

When it is necessary to remove microorganism or cell debris from the liquid containing disrupted cells, such methods as centrifugation or filtration (dead end mode or cross flow mode) may be used.

Centrifugal operations may be performed as described above. When microorganism or cell debris is too fine to precipitate easily, it is possible to add a flocculant to improve the efficiency of debris precipitation. Organic polymer flocculants may be classified into cationic, anionic, amphoteric and nonionic flocculants based on ionicity; and classified into acryl type, polyethyleneimine type, condensed polycation (polyamine) type, dimethyldiallylammonium chloride type and chitosan type based on raw material. The flocculant to be used in the present invention may be any flocculant provided that it does not decrease the activity of improved hydroxynitrile lyase or the recovery ratio of the activity and yet is capable of improving the efficiency of debris separation. Examples of acrylic aqueous monomers which can be components of acryl type flocculants include acrylamide, sodium acrylate, sodium acrylamide-2-methyl-propanesulfonate, dimethylaminoethyl-methacrylate, methacryloyloxyethyl-trimethylammoniu m-chloride, methacryloyloxyethyl-benzyldimethyl-ammonium chloride, dimethylaminoethyl-acrylate, acryloyloxyethyl-trimethylammonium-chloride, dimethylaminopropyl-acrylamide, acrylamide propyl-trimethylammonium-chloride, and polyamidine-chloride. Single polymers of these monomers; copolymers of diversified composition of these monomers; and high molecular modified products of these monomers; are enumerated as acryl type flocculants. As representative examples of cationic polymer flocculants, polyaminoalkylmethacrylates, copolymers of polyaminoalkylmethacrylate and acrylamide, Mannich modified products of polyacrylamide, polydimethyldiallyammonium salts, polyvinylimidazolines, polyacrylamides, amine type polycondensated products and the like may be enumerated, and a great number of them have already been commercialized. Major products include Sanpoly-K-601, K-602 (principal component: polyamine; Sankyo Kasei); Kuriflock LC-599 (principal components: polyamine and polyamide; Kurita Water); Hymolock M-166, M-566, M-966 (principal component: acrylamide modified product; Kyoritu Organic Industry); Uniflocker UF-301, UF-304, UF-305 (principal component: polyacrylamide; Unitika), UF-330, UF-340 (principal component: aminomethacrylic acid ester; Unitika), UF-505 (principal component: dicyano amine; Unitika); Ryufloc C-110 (principal component: polyamine; Dainippon Ink & Chemicals); and Purifloc C-31 (principal component: polyamine; Dow Chemical) may be enumerated. Further, K-400 series, KM-200 series, KM-1200 series, KAM-200 series, KD-200 series, KP-000 series, KP-100 series, KP-200 series, KP-300 series, KP-500 series, KP-1200 series, KA-000 series, KA-200 series, KA-300 series, KA-400 series, KA-600 series, KA-700 series and KA-800 series manufactured by DiaNitrix (Japan) may also be enumerated. These flocculants may be used alone or in a combination of two or more. Any of the above-described flocculants may be used in the present invention provided that it does not decrease the activity of improved hydroxynitrile lyase and the activity recovery ratio thereof and yet is capable of improving the efficiency of debris separation. Specifically, DiaNitrix (Japan) products such as K-401, K-403B, K-405, K-408, K-409, K-415, KP201H, KP309 or KP7000 may be used, for example. The amount of flocculant to be added varies depending on the type of flocculant and the condition of the liquid containing disrupted microorganisms or cells. For example, the flocculant may be used at a concentration of 1/50-1/2, preferably 1/20-1/5, relative to the dry weight % concentration of the disrupted microorganism. The flocculant may be added as follows, for example; after dissolved in water, the flocculant is added to the liquid containing disrupted microorganisms or cells, and then the liquid is left stationary or agitated for at least 5 minutes to 24 hours, preferably for 30 minutes to 10 hours. The temperature at that time may be preferably 0-60° C., more preferably 0-50° C., still more preferably 0-40° C. When pH adjustment is necessary, an inorganic salt may be added at a final concentration of 5-200 mM to buffer the liquid. Alternatively, a substance which stabilizes the improved hydroxynitrile lyase may be added.

When the debris is separated by filtration, either microfiltration (MF) membrane or ultrafiltration (UF) membrane may be used as along as the desired separation of debris can be achieved. Usually, it is preferable to use a MF membrane. Any MF membrane may be used as long as it is capable of separation of debris. The pore size of the membrane is not particularly limited provided that the pore allows capturing of the microorganism or cell debris and yet the activity of improved hydroxynitrile lyase is recovered in the filtrate. For example, a membrane with a pore size of about 0.1 to 0.5 µm may be used. Further, with the use of a filter aid and occasionally a flocculant, a membrane or filter paper with a pore size of 0.5 µm or more may also be used. Specific examples of filter aids include diatomaceous earth, cellulose powder and active carbon. Flocculants are as described above.

The supernatant obtained after removal of the debris is a cell extract soluble fraction, and this may be used as a crude enzyme solution containing the improved hydroxynitrile lyase. Subsequently, common biochemical methods used for isolation/purification of proteins, such as ammonium sulfate precipitation, various chromatographies [e.g., gel filtration chromatography (with Sephadex column, etc.), ion exchange chromatography (with DEAE-Toyopearl, etc.), affinity chromatography, hydrophobic chromatography (with butyl Toyopearl, etc.), anion chromatography (with MonoQ column, etc.)] or SDS polyacrylamide gel electrophoresis may be performed independently or in a combination to thereby isolate/purify the hydroxynitrile lyase from the culture.

When the improved hydroxynitrile lyase is produced within the microorganisms or cells, the microorganisms or cells per se may be recovered by centrifugation, membrane separation, etc. and used in enzyme reactions of interest without disrupting. In this case, it is also possible to use the treated culture which include cultured cells in a gel such as acrylamide, cultured cells treated with glutaraldehyde, or cultured cells carried by an inorganic substance such as alumina, silica, zeolite, diatomaceous earth or the like, if necessary.

On the other hand, when the transformant of the present invention is a genetic recombinant and there is a possible risk of leakage of the transformant into environments or mixing thereof with the final product during the production process, or a possible risk of causing a microorganism pollution secondarily due to inappropriate handling or the like of the used transformant, inactivation of the transformant may be performed. As the method of inactivation, any method may be used provided as long as it is capable of inactivating the transformant without decreasing the activity of improved hydroxynitrile lyase or the recovery ratio of the activity. For example, such methods as thermal treatment, cell disrupting treatment or drug treatment may be performed independently or in a combination. For example, the transformant may be inactivated by treating it with a drug before or after cell disrupting treatment. The drug to be used varies depending on the type of host of the transformant. For example, cationic surfactants such as benzethonium chloride, cetylpyridinium chloride, methylstearoyl chloride and cetyltrimethylammonium bromide; or aldehydes such as glutaraldehyde may be enumerated. Further, alcohols such as ethanol, thiols such as 2-mercaptoethanol, amines such as ethylenediamine, and amino acids such as cysteine, ornithine and citrulline may also be enumerated. The concentration of drug may be a concentration which is capable of inactivating the transformant without decreasing the activity of improved hydroxynitrile lyase or the recovery ratio of the activity. For example, when the host of the transformant is $E.\ coli$ and the drugs are benzethonium chloride and glutaraldehyde, respective final concentrations of these drugs are preferably in the range from 0.05-0.5%. At the time of this inactivation treatment, flavonoids or the like may be added in order to improve the stability of the improved hydroxynitrile lyase. The treatment temperature may be 0-50° C., preferably 0-40° C. The pH is preferably 4-8.

On the other hand, when the improved hydroxynitrile lyase is produced outside the microorganisms or cells, the culture broth may be used as it is or after removal of microorganisms or cells by the above-described centrifugation or filtration. Then, the improved hydroxynitrile lyase may be recovered from the culture by such method as extraction by ammonium sulfate precipitation and, if necessary, purified by one or a combination of the following methods: dialysis and various chromatographies such as gel filtration, ion exchange chromatography, affinity chromatography and the like.

When the transformant is a plant cell or tissue, cells are disrupted by lysis treatment using enzymes such as cellulase or pectinase, sonication treatment, or grinding treatment. Subsequently, if necessary, common biochemical methods used for isolation/purification of proteins, such as ammonium sulfate precipitation, various chromatographies [e.g., gel filtration chromatography (with Sephadex column, etc.), ion exchange chromatography (with DEAE-Toyopearl, etc.), affinity chromatography, hydrophobic chromatography (with butyl Toyopearl, etc.), anion chromatography (with MonoQ column, etc.)] or SDS polyacrylamide gel electrophoresis may be performed independently or in a combination to thereby isolate/purify the hydroxynitrile lyase from the culture.

The thus obtained improved hydroxynitrile lyase is included in the scope of the present invention. The production yield of the improved hydroxynitrile lyase may be calculated by measuring the activity of improved hydroxynitrile lyase per unit, such as culture equipment, culture broth, cell wet weight or dry weight, weight of protein in enzyme solution, etc. The unit is not particularly limited. The activity of improved hydroxynitrile lyase may be expressed by the value of either degradation activity or synthesis activity as described earlier. Alternatively, the activity may be calculated indirectly by means of analysis such as SDS-PAGE. One of ordinary skill in the art can perform SDS-PAGE using known methods. Further, it is also possible to calculate the activity by preparing an antibody to the improved hydroxynitrile lyase and using immunological techniques such as Western blotting or ELISA.

In the present invention, it is also possible to collect the improved hydroxynitrile lyase from the above-described improved hydroxynitrile lyase gene or a recombinant vector comprising the gene. Briefly, it is possible to produce the improved hydroxynitrile lyase using a cell-free protein synthesis system without using living cells. The term "cell-free protein synthesis system" means a system which synthesizes a protein using a cell extract in an artificial container such as a test tube. A cell-free transcription system which synthesizes RNA from DNA as a template is also included in the cell-free protein synthesis system used in the present invention. In this case, an organism corresponding to the above-described host is the organism from which the cell extract described below is derived. As the cell extract, a eukaryote- or prokaryote-derived cell extract (e.g., an extract from wheat germs or *E. coli*) may be used. These cell extracts may be either concentrated or non-concentrated. Cell extracts may be obtained by such methods as ultrafiltration, dialysis or polyethylene glycol (PEG) precipitation. In the present invention, cell-free protein synthesis may also be performed with a commercial kit. Examples of such kits include reagent kits PROTEIOS™ (Toyobo) and TNT™ System (Promega) and synthesis apparatuses PG-Mate™ (Toyobo) and RTS (Roche Diagnostics).

The improved hydroxynitrile lyase obtained by the above-described cell-free synthesis may be purified, for example, by appropriately selecting chromatography.

(VI) Method for Preparing Cyanohydrin and Method for Preparing Hydroxycarboxylic Acid The improved hydroxynitrile lyase prepared as described above may be utilized in the production of substances as an enzyme catalyst. For example, by contacting the above-described improved hydroxynitrile lyase with either a ketone compound or aldehyde compound and a cyanide compound, an optically active cyanohydrin may be prepared. As the enzyme catalyst, a culture obtained by culturing a host into which the improved hydroxynitrile lyase gene has been transferred as to express the gene in any hosts or a treated culture may be used. The treated culture, for example, include cultured cells in a gel such as acrylamide, cultured cells treated with glutaraldehyde, or cultured cells carried by an inorganic carrier such as alumina, silica, zeolite or diatomaceous earth may be enumerated.

Either a ketone compound or aldehyde compound and a cyanide compound which are used as substrates are selected considering the substrate specificity of the enzyme and the stability of the enzyme against substrates. When the enzyme is a cassava (*Manihot esculenta*)-derived hydroxynitrile lyase, suitable substrates are an aldehyde compound and a cyanide compound. As the aldehyde compound, benzaldehyde is preferable. As the cyanide compound, prussic acid is preferable.

The effect of metal ions in cyanohydrin synthesis reaction becomes less when H103M improved hydroxynitrile lyase is used, as compared to the case where wild-type hydroxynitrile lyase is used. Further, the synthesis of cyanohydrin is hardly affected by the presence of nickel ions.

The form of use and the reaction mode of a biocatalyst are selected appropriately depending on the type, etc. of the biocatalyst. As the form of use of the biocatalyst, the above-described culture or purified enzyme may be used as it is. Alternatively, the culture or purified enzyme may be carried on an appropriate carrier and used as an immobilized enzyme.

The method of reaction and the method of recovering cyanohydrin after completion of the reaction are selected appropriately considering the properties of the substrates and the enzyme catalyst. It is preferable to recycle an enzyme catalyst as long as it is not deactivated. From the viewpoints of preventing deactivation and facilitating recycling, it is preferable to use the enzyme catalyst in the form of a treated culture.

In the present invention, the term "optically active" refers to the state of a substance where one enantiomer is contained more than the other enantiomer, or the state of a substance where the substance is consisting of either one of the enantiomers.

It is also possible to convert the recovered optically active cyanohydrin to optically active hydroxycarboxylic acid by performing hydrolysis reaction with a mineral acid such as sulfuric acid or hydrochloric acid. Preferably, the hydrolysis reaction is performed using a mineral acid in the same manner as in conventional methods. Examples of mineral acid which may be used here include hydrochloric acid, sulfuric acid, nitric acid, boric acid, phosphoric acid and perchloric acid. Of these, hydrochloric acid is preferable. Usually, the solvent used in the hydrolysis process is water. If necessary, polar solvents such as dimethylsulfoxide, dimethylformamide or dimethylacetamide; hydrocarbon solvents such as toluene, hexane or heptane; or ether solvents such as diethyl ether, diisopropyl ether, t-butylmethyl ether or tetrahydrofuran may be used in conjunction with water. These solvents may be used alone or in a combination. The amount of mineral acid to be used is preferably 0.5-20 equivalents, more preferably 0.9-10 equivalents and most preferably 1-5 equivalents, relative to the amount of optically active cyanohydrin contained in the reaction mixture supplied to hydrolysis. Use of a mineral acid within this range is preferable because it is advantageous economically and improves the recovery ratio of hydroxycarboxylic acid. The reaction temperature of the hydrolysis process is preferably from −5° C. to the boiling point of the solvent used, especially preferably in the range from 10 to 90° C. The temperature within this range is desirable from the viewpoints of the rate of hydrolysis reaction and reduction of impurities.

Hereinbelow, the present invention will be described more specifically with reference to the following Examples. However, the present invention is not limited by these Examples.

EXAMPLE 1

Obtainment of Plant Codon Wild-type Hydroxynitrile Lyase Gene (1) Preparation of Plant Codon Wild-type hydroxynitrile Lyase Gene by PCR Based on the nucleotide sequence disclosed in GenBank accession number Z29091, a cassava (*Manihot esculenta*)-derived hydroxynitrile lyase gene represented by the sequence of SEQ ID NO: 2 was synthesized by PCR.

Figure 1:
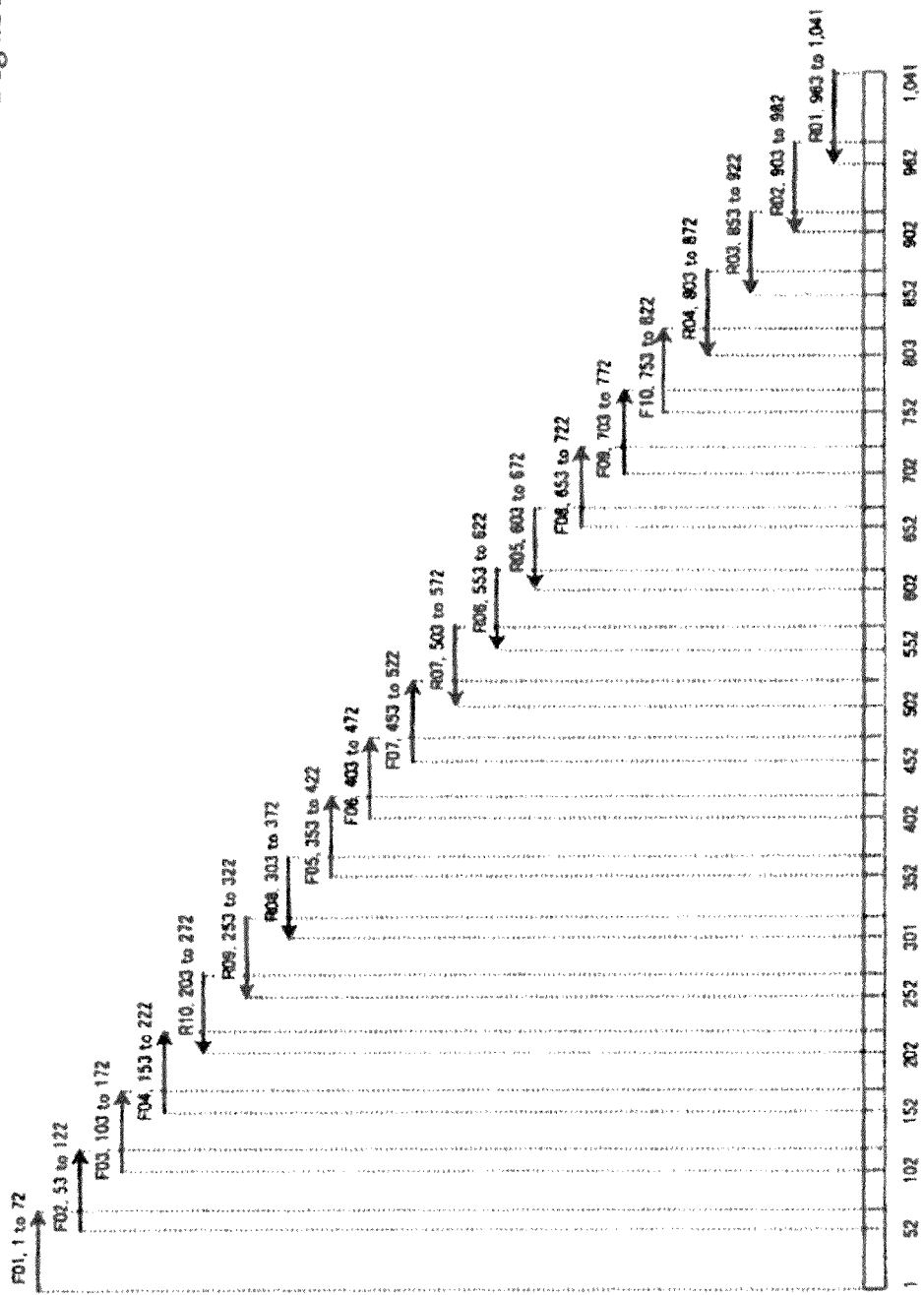
FIG. 1 is a schematic diagram showing the preparation of a plant codon wild-type hydroxynitrile lyase gene in Example 1.

Specifically, 20 oligonucleotides designated F01-F10 and R01-R10 (SEQ ID NOS: 4-23) were designed and synthesized. Briefly, the 20 oligonucleotides F01-F10 and R01-R10 were designed so that they are complementary to a nucleotide sequence comprising the cassava (*Manihot esculenta*)-derived hydroxynitrile lyase gene disclosed in GenBank accession number Z29091 and its 5' and 3' untranslated regions (sense strand) and a complementary sequence thereto (antisense strand) (1,041 bp). In F01, 11 nucleotides (shown in italics) containing a BamHI recognition site are added to its 5' end. In R01, 9 nucleotides (shown in italics) containing a KpnI recognition site are added to its 5' end. These oligonucleotides were designed so that the 1,041 bp comprising the cassava-derived hydroxynitrile lyase gene are ultimately amplified. These oligonucleotides were designed so that they overlap with the adjacent oligonucleotide(s) by about 20 bp. For example, F01 and F02 are designed so that the underlined part of F01 and the underlined part of F02 are overlapping with each other. FIG. 1 schematically illustrates the positional relations among these 20 oligonucleotides F01-F10 and R01-R10 (SEQ ID NOS: 4-23).

```
F01 (SEQ ID NO: 4):
cgggatccccaaaaagagttagatatcatttccaaaatggtaactgcacatttgttctgattcataccatt F02 (SEQ ID NO: 5):
ttgttctgattcataccatttgccatggtgcatggatttggcataagctcaaaccagcccttgagagagc F03 (SEQ ID NO: 6):
aaaccagcccttgagagagctggccacaaagtcactgcactggacatggcagccagcggcattgacccaa F04 (SEQ ID NO: 7):
agccagcggcattgacccaaggcaaattgagcagattaattcatttgatgaatactctgaacccttattg F05 (SEQ ID NO: 8):
tattgccagacaccgttcatagcccatcttacactgtggaaaagcttttggagtcgtttcctgactggag F06 (SEQ ID NO: 9):
gagtcgtttcctgactggagagacacagagtattttacgttcactaatatcactggagagacaattacaa F07 (SEQ ID NO: 10):
cactggagagacaattacaacaatgaagctgggcttcgtacttctgagggaaaatttatttaccaaatgc F08 (SEQ ID NO: 11):
atcaagacaaaatattttaccagactttcaacgctggcaaattgcaaactacaaaccagacaaggttta F09 (SEQ ID NO: 12):
tacaaaccagacaaggtttatcaggttcaaggtggagatcataagctccagcttacaaaaactgaggagg F10 (SEQ ID NO: 13):
gcttacaaaaactgaggaggtagctcatattctccaagaggtggctgatgcatatgcttgaagcttttag R01 (SEQ ID NO: 14):
gcggtaccettaataggatatttatttatttaatttaaagattacataatagggataacattcccttaaatacacacat R02 aactca (SEQ ID NO: 15):
attcccttaaatacacacatctcagcaaatgaagagacaccaacgtggaactctcccatatttaaagaaaaaaa R03 (SEQ ID NO: 16):
tttaaagaaaaaaaaactcaaactttatttagtgcaatttaattctcacatgaaaatgtgagattattt R04 (SEQ ID NO: 17):
atgaaaatgtgagattatttataactgcacccaggttaacttaataggagctaaaagcttcaagcatatg R05 (SEQ ID NO: 18):
taaaaatattttgtcttgatcggtccaaatataaactttcttaattgatccgtaacctttttcggtgaac R06 (SEQ ID NO: 19):
cgtaaccttttcggtgaacttcggtctctgagccaaaacattttgaaacagtgatcccttcctcattac R07 (SEQ ID NO: 20):
agtgatcccttcctcattaccatttttgccagttcatattcccatcagtgcatttggtaaataaatttt R08 (SEQ ID NO: 21):
atgaacggtgtctggcaataaggaattgtggaaaacaccagctgcaattttgtcaacgtatctatcagca R09 (SEQ ID NO: 22):
tgtcaacgtatctatcagcagcaatagcaatattcagccctgcacagctctcaccaacaatgatgacctt R10 (SEQ ID NO: 23):
tcaccaacaatgatgacctttcccttgagggagtttctccaagaaagtcaataagggttcagagtatt
```

Each of the oligonucleotides was lyophilized and re-suspended in distilled water to give a concentration of 100 pmol/μl. One μl aliquot was taken from each of the 20 oligonucleotide suspensions to prepare a mix oligo. The resultant mixture was added to PCR-mix (Pwo 10× buffer, dNTP mix, Pwo DNA polymerase) (Boehringer Mannheim). Table 3 shows the composition of the PCR reaction solution.

TABLE 3

| PCR solution | A (μl) | B (μl) | C (μl) |
| --- | --- | --- | --- |
| Mix oligo (μl) | 0.5 | 1 | 2 |
| Pwo 10× buffer | 5 | 5 | 5 |
| dNTP mix | 5 | 5 | 5 |
| Pwo DNA polymerase | 0.5 | 0.5 | 0.5 |
| Distilled water | 39 | 38.5 | 37.5 |

PCR was performed for 55 cycles (94° C. for 30 sec, 52° C. for 30 sec and 72° C. for 30 sec) to extend the oligonucleotides to thereby synthesize the gene of interest (1st PCR).

Subsequently, the thus synthesized gene was amplified (2nd PCR). Briefly, to 1.3 μl of the reaction product of PCR solution B in the 1st PCR, 5 μl of Pwo 10× buffer, 5 μl of dNTP mix, 0.5 μl of Pwo DNA polymerase, 36.2 μl of distilled water and 1 μl of external primers were added. As the external primers, F01 (SEQ ID NO: 4) and R01 (SEQ ID NO: 14) were used. The 2nd PCR were performed for 23 cycles (94° C. for 30 sec, 50° C. for 30 sec and 72° C. for 60 sec) to amplify the gene.

The amplified product of the 2nd PCR was confirmed on 1.5% agarose gel.

(2) Preparation of Recombinant Vector Comprising Plant Codon Wild-type Hydroxynitrile Lyase Gene A 0.9 kb band which is the amplified product in the 2nd PCR obtained in (1) above was purified with QIAquick Gel Extraction Kit (QIAGEN). The DNA purified from gel (5 μl) was digested with restriction enzymes BamHI (1 μl) (its recognition site is included in oligonucleotide F01) and KpnI (1 μl) (its recognition site is included in oligonucleotide R01) at 37° C. for one hour. Then, the DNA was purified from the reaction solution by phenol extraction, chloroform extraction and ethanol precipitation [Molecular Cloning, A Laboratory Manual, 2nd ed. (Cold Spring Harbor Laboratory Press (1989))]. The thus purified DNA (5 μl), a vector pUC19 (Takara Bio) (1 μl) predigested with BamHI and KpnI, distilled water (4 μl) and solution I (DNA Ligation Kit ver. 2; Takara Bio) (10 μl) were mixed to prepare a ligation mixture. This mixture was incubated at 16° C. for 12 hours to thereby ligate the amplified product to the vector.

(3) Preparation of E. coli JM109 Competent Cells

E. coli JM109 strain was inoculated into 1 ml of LB medium (1% Bacto tryptone, 0.5% Bacto yeast extract, 0.5% NaCl) and precultured at 37° C. for 5 hours aerobically. The resultant preculture (0.4 ml) was added to 40 ml of SOB medium (2% Bacto tryptone, 0.5% Bacto yeast extract, 10 mM NaCl, 2.5 mM KCl, 1 mM MgSO$_4$, 1 mM MgCl$_2$) and cultured at 18° C. for 20 hours. The resultant culture was harvested by centrifugation (3,700×g, 10 minutes, 4° C.) and, after addition of 13 ml of cold TF solution (20 mM PIPES-KOH (pH 6.0), 200 mM KCl, 10 mM CaCl$_2$, 40 mM MnCl$_2$) thereto, the culture was left at 0° C. for 10 minutes. Subsequently, the culture was re-centrifuged (3,700×g, 10 minutes, 4° C.) to remove the supernatant. The precipitated E. coli cells were suspended in 3.2 ml of cold TF solution and, after addition of 0.22 ml of dimethylsulfoxide thereto, the cell suspension was left at 0° C. for 10 minutes.

(4) Cloning of the Plant Codon Wild-type hydroxynitrile Lyase Gene

The competent cell prepared in (3) above (200 μl) was added to the ligation product prepared in (2) above (10 μl) and left at 0° C. for 30 minutes. Subsequently, heat shock was given to the competent cell at 42° C. for 30 sec, followed by cooling at 0° C. for 2 minutes. Then, 1 ml of SOC medium (20 mM glucose, 2% Bacto tryptone, 0.5% Bacto yeast extract, 10 mM NaCl, 2.5 mM KCl, 1 mM MgSO$_4$, 1 mM MgCl$_2$) was added thereto, and the resultant mixture was subjected to shaking culture at 37° C. for 1 hour. The resultant culture was plated in 200 μl aliquots on LB Amp agar medium (LB medium containing 100 mg/L ampicillin and 1.5% agar) and cultured overnight at 37° C. A plurality of transformant colonies grown on the agar medium were cultured overnight in 1.5 ml of LB Amp medium (LB medium containing 100 mg/L ampicillin) at 37° C. Each of the resultant cultures was harvested, followed by recovery of the recombinant vector with Flexi Prep (Amersham Bioscience). The nucleotide sequence of the resultant recombinant vector was analyzed with CEQ DTCS Quick Start Kit and a fluorescence sequencer CEQ 2000XL DNA Analysis system (both from BECKMAN COULTER; USA). As primers, oligonucleotides F01-F10 and R01-R10 were used. One of the recombinant vectors having a nucleotide sequence identical to the nucleotide sequence of the cassava (*Manihot esculenta*)-derived hydroxynitrile lyase gene as disclosed in GenBank accession number Z29091 and shown in SEQ ID NO: 2 was designated pUME.

EXAMPLE 2

Preparation of Plant Codon Wild-Type Hydroxynitrile Lyase Expression Vectors (1) Preparation of Plant Codon Wild-Type Hydroxynitrile Lyase Expression Vector (Based on pUC19)

An SD sequence was added to the nucleotide sequence of the plant codon wild-type hydroxynitrile lyase gene obtained in Example 1 to obtain a DNA fragment, which was then inserted at the PstI-BamHI site of pUC19 to thereby prepare a pUC19-based plant codon wild-type hydroxynitrile lyase expression vector pUMESD, as described below. First, a modified DNA fragment encoding the hydroxynitrile lyase was prepared by PCR. The reaction mixture for PCR was composed of 5 μl of Pwo 10× buffer, 5 μl of dNTP mix, 0.5 μl of Pwo DNA polymerase, 36.2 μl of distilled water, 1 μl of sense and antisense primers, and 1 μl of pUME as a template. PCR was performed as follows: 95° C. for 2 minutes for denaturation, 30 cycles of 94° C. for 30 sec, 50° C. for 30 sec and 72° C. for 2 minutes; and finally 72° C. for 10 minutes. The sense primer MES-1 (SEQ ID NO: 24) consists of 62 nucleotides, and has an PstI recognition site, a ribosome binding site, the TAG termination codon for the lacZ gene frame of pUC19 and the ATG initiation codon for the hydroxynitrile lyase gene in its sequence. The antisense primer MES-2 (SEQ ID NO: 25) consists of 33 nucleotides and has a BamHI recognition site in its sequence.

```
Sense primer:      cccccaaactgcagtaaggaggaatagaaaatggtaactgcacattttgttctgattcatacc
```
(SEQ ID NO: 24)

```
Antisense primer:  tagtgcaattggatcctcacatgaaaatgtgag
```
(SEQ ID NO: 25)

The amplified PCR product obtained by the PCR was digested with PstI and BamHI, separated by agarose gel electrophoresis, and then purified with QIAquick Gel Extraction Kit. The resultant purified DNA fragment (5 µl), pUC19 (Takara Bio, Japan) (5 µl) predigested with PstI and BamHI, and solution I (DNA Ligation Kit ver.2; Takara Bio) (10 µl) were mixed to prepare a ligation mixture. This mixture was incubated at 16° C. for 12 hours to ligate the linker to the vector. E. coli JM109 strain was transformed in the same manner as described in (4) in Example 1. The recombinant vectors were recovered from the grown colonies. A plasmid in which the modified DNA fragment (PstI-BamHI fragment) comprising the plant codon wild-type hydroxynitrile lyase gene was inserted correctly downstream of the lac promoter of pUC19 was designated expression vector pUMESD.

(2) Preparation of Plant Codon Wild-Type Hydroxynitrile Lyase Expression Vector (Based on pKK233-2)

A DNA fragment of the cassava (*Manihot esculenta*)-derived wild-type hydroxynitrile lyase gene obtained in Example 1 was inserted at the NcoI-Sse8387I site of pKK233-2(+Sse), a derivative of pKK233-2 (Centraalbureau voor Schimmelcultures (CBS), Netherlands; http://www.cbs.knaw.nl/), to prepare a plant codon wild-type hydroxynitrile lyase expression vector pOXN103 based on pKK233-2, as described below. First, a DNA fragment encoding the plant codon wild-type hydroxynitrile lyase was amplified by PCR in such a manner that the amplified fragment has at its both ends a restriction enzyme recognition site which can be easily introduced into an expression vector. The PCR reaction mixture was composed of 5 µl of Pwo 10× buffer, 5 µl of dNTP mix, 0.5 µl of Pwo DNA polymerase, 36.2 µl of distilled water, 1 µl of sense and antisense primers, and 1 µl of plasmid pUME as a template. PCR was performed as follows: 95° C. for 2 minutes for denaturation and 30 cycles of 94° C. for 30 sec, 50° C. for 30 sec and 72° C. for 2 minutes. The sense primer OXYN-6 (SEQ ID NO: 26) consists of 29 nucleotides, and includes an NcoI recognition site and the AGT initiation codon and subsequent several codons of the hydroxynitrile lyase gene in its sequence. The antisense primer OXYN-9 (SEQ ID NO: 27) consists of 33 nucleotides, and includes an Sse8387I recognition site in its sequence.

```
                                      (SEQ ID NO: 26)
OXYN-6:    ccaccatggtaactgcacattttgttctg
```

```
                                      (SEQ ID NO: 27)
OXYN-9:    ggcctgcaggttaacttaataggagctaaaagc
```

The resultant amplified PCR product was digested with Sse8387I and then partially digested with NcoI. The digest was separated by agarose gel electrophoresis. A band (about 0.8 kb) comprising the full length of the plant codon wild-type hydroxynitrile lyase gene was cut out from the gel. The amplified PCR product in the gel was purified with QIAquick Gel Extraction Kit.

Subsequently, an expression vector pKK233-2(+Sse) was prepared as described below. pKK233-2 (Centraalbureau voor Schimmelcultures (CBS), Netherlands; http://www.cbs.knaw.nl/) (5 µl) was digested with HindIII (1 µl) and purified by phenol extraction, chloroform extraction and ethanol precipitation. The purified digest was blunt-ended using DNA Blunting Kit (Takara Bio). The thus treated solution was re-purified by phenol extraction, chloroform extraction and ethanol precipitation. The purified expression vector (5 µl) was subjected to dephosphorylation treatment using Shrimp Alkaline Phosphatase (Takara Bio). The treated solution was re-purified by ethanol precipitation. The purified vector DNA (5 µl), annealed Sse8387I phosphorylated linker pSse8387I (Takara Bio) (5 µl) and solution I (DNA Ligation Kit ver.2; Takara Bio) (10 µl) were mixed to prepare a ligation mixture. This mixture was incubated at 16° C. for 12 hours to ligate the linker to the vector. E. coli JM109 strain was transformed in the same manner as described in (4) in Example 1. The recombinant vectors were recovered from the grown colonies. The recovered recombinant vectors were subjected to Sse8387I digestion, and those which had been confirmed to be digested linearly were designated pKK233-2(+Sse). After digestion with restriction enzymes NcoI and Sse8387I, pKK233-2(+Sse) was purified by phenol extraction, chloroform extraction and ethanol precipitation.

The above-described DNA fragment (5 µl) of the plant codon wild-type hydroxynitrile lyase gene and expression vector pKK233-2(+Sse) (5 µl) were mixed. Solution I (DNA Ligation Kit ver.2; Takara Bio) (10 µl) was added to this mixture to prepare a ligation mixture. This mixture was incubated at 16° C. for 12 hours to ligate the linker to the vector. E. coli JM109 strain was transformed in the same manner as described in (4) in Example 1. The recombinant vectors were recovered from the grown colonies. A plasmid in which the DNA fragment of the plant codon wild-type hydroxynitrile lyase gene was ligated to the vector correctly was confirmed, and designated plant codon wild-type hydroxynitrile lyase expression recombinant vector pOXN103. At the same time, a plant codon wild-type hydroxynitrile lyase-expressing transformant JM109/pOXN103 was obtained.

EXAMPLE 3

Figure 2:
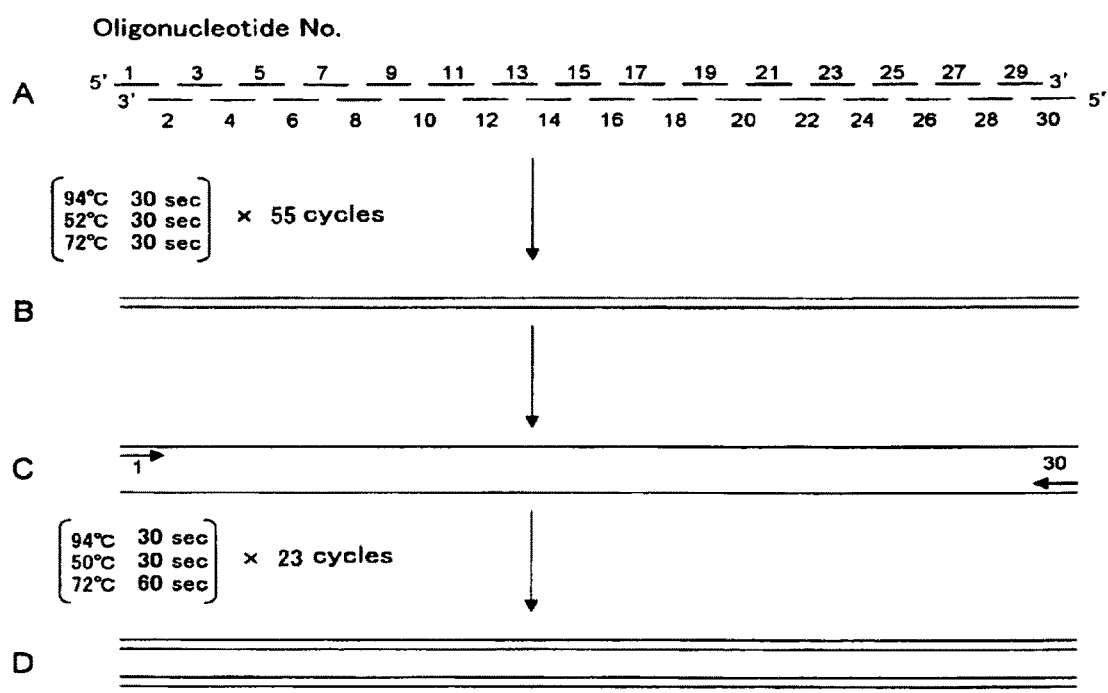
FIG. 2 is a schematic diagram showing the preparation of an *E. coli* codon wild-type hydroxynitrile lyase gene in Example 3.

Obtainment of E. coli Codon Wild-Type Hydroxynitrile Lyase Gene (1) Design and Preparation of E. coli Codon Wild-Type Hydroxynitrile Lyase Gene by PCR A hydroxynitrile lyase gene was newly designed, and some of its codons were converted to those codons frequently used in E. coli. Specifically, 30 oligonucleotides Nos. 1-30 (of these, 6 types consisting of 49 nt; 21 types consisting of 50 nt; 2 types consisting of 27 nt; and 1 type consisting of 48 nt) (SEQ ID NOS: 28-57) were designed and synthesized ultimately, and then prepared on 50 nmol scale. These 30 oligonucleotides were designed so that they overlap by 20 nt (FIG. 2).

No. 1:
```
                                      (SEQ ID NO: 28)
aaaagagttagatatcatttccaaaatggtgaccgcgcattttgtgctg
```

No. 2:
```
                                      (SEQ ID NO: 29)
tccacgcgccatggcaaatggtatgaatcagcacaaaatgcgcggtcacc
```

No. 3:
(SEQ ID NO: 30)
ttgccatggcgcgtggatttggcataaactgaaaccggcgctggaacgcg

No. 4:
(SEQ ID NO: 31)
ccatatccagcgcggtcactttatggcccgcgcgttccagcgccggtttc

No. 5:
(SEQ ID NO: 32)
agtgaccgcgctggatatggcggcgagcggcattgatccgcgccagattg

No. 6:
(SEQ ID NO: 33)
cgctatattcatcaaagctgttaatctgttcaatctggcgcggatcaatg

No. 7:
(SEQ ID NO: 34)
cagctttgatgaatatagcgaaccgctactgacctttctggaaaaactgc

No. 8:
(SEQ ID NO: 35)
cgcccacaataatcacttttcgccctgcggcagttttccagaaaggtc

No. 9:
(SEQ ID NO: 36)
aaaagtgattattgtgggcgaaagctgcgcgggcctgaacattgcgattg

No. 10:
(SEQ ID NO: 37)
ccgcaattttatccacatagcgatccgccgcaatcgcaatgttcaggccc

No. 11:
(SEQ ID NO: 38)
ctatgtggataaaattgcggcgggcgttttcataacagcctgctgccgg

No. 12:
(SEQ ID NO: 39)
ccacggtatagctcgggctatgcacggtatccggcagcaggctgttatg

No. 13:
(SEQ ID NO: 40)
tagcccgagctataccgtggaaaaactgctggaaagctttccggattggc

No. 14:
(SEQ ID NO: 41)
tgttggtaaaggtaaaatattcggtatcgcgccaatccggaaagctttcc

No. 15:
(SEQ ID NO: 42)
atattttacctttaccaacattaccggcgaaaccattaccaccatgaaac

No. 16:
(SEQ ID NO: 43)
acaggttttcgcgcagcagcacaaagcccagtttcatggtggtaatgg

No. 17:
(SEQ ID NO: 44)
ctgctgcgcgaaaacctgtttaccaaatgcaccgatggcgaatatgaac

No. 18:
(SEQ ID NO: 45)
ggctgcctttgcgcatcaccattttcgccagttcatattcgccatcggtg

No. 19:
(SEQ ID NO: 46)
ggtgatgcgcaaaggcagcctgtttcagaacgtgctggcgcagcgcccg

No. 20:
(SEQ ID NO: 47)
taatgctgccatagccttttcggtaaatttcgggcgctgcgccagcacg

No. 21:
(SEQ ID NO: 48)
aaaaggctatggcagcattaaaaaagtgtatatttggaccgatcagg

No. 22:
(SEQ ID NO: 49)
agcgctgaaaatccggcagaaaaattttatcctgatcggtccaaatatac

No. 23:
(SEQ ID NO: 50)
gccggattttcagcgctggcagattgcgaactataaaccggataaagtg

No. 24:
(SEQ ID NO: 51)
gtttatgatcgccgccctgcacctgatacactttatccggtttatagttc

No. 25:
(SEQ ID NO: 52)
gggcggcgatcataaactgcagctgaccaaaaccgaagaagtggcgc

No. 26:
(SEQ ID NO: 53)
catacgcatccgccacttcctgcagaatatgcgccacttcttcggttttg

No. 27:
(SEQ ID NO: 54)
agtggcggatgcgtatgcgtgaagcttttagctcctattaagttaacctg

No. 28:
(SEQ ID NO: 55)
tgaaaatgtgagattatttataactgcacccaggttaacttaataggagc

No. 29:
(SEQ ID NO: 56)
taaataatctcacatttcatgtgagaattaaattgcactaaaataaag

No. 30:
(SEQ ID NO: 57)
catatttaaagaaaaaaaaactcaaactttattttagtgcaatttaattc

Each of the oligonucleotides was lyophilized and re-suspended in distilled water to give a concentration of 100 pmol/µl. One µl aliquot was taken from each of the 30 oligonucleotide suspensions to prepare a mix oligo. The resultant mixture was added to PCR-mix (Pwo 10× buffer, dNTP mix, Pwo DNA polymerase) (Boehringer Mannheim) in the amounts indicated in Table 4 below.

TABLE 4

| Composition of PCR Solution | | |
| --- | --- | --- |
| PCR solution | A (µl) | B (µl)) |
| Mix oligo | 0.5 | 1 |
| Pwo 10× buffer | 5 | 5 |
| dNTP mix | 5 | 5 |
| Pwo DNA polymerase | 0.5 | 0.5 |
| Distilled water | 39 | 38.5 |
| Total (µl) | 50 | 50 |

PCR was performed for 55 cycles (94° C. for 30 sec, 52° C. for 30 sec and 72° C. for 30 sec) to extend the oligonucleotides to thereby synthesize a gene of interest (1st PCR).

Subsequently, the thus synthesized gene was amplified (2nd PCR). Briefly, to 1.3 µl of the reaction product of A or B shown in above the Table, 5 µl of Pwo 10× buffer, 5 µl of dNTP mix, 0.5 µl of Pwo DNA polymerase, 36.2 µl of distilled water and 1 µl of external primers were added. As the external primers, oligonucleotides No. 1 (SEQ ID NO: 28) and No. 30 (SEQ ID NO: 57) were used. The 2nd PCR were performed for 23 cycles (94° C. for 30 sec, 50° C. for 30 sec and 72° C. for 60 sec) to amplify the gene.

The amplified product from the 2nd PCR was analyzed on 1.5% agarose gel. Subsequently, a 0.9 kb band was purified with QIAquick Gel Extraction Kit (QIAGEN). The DNA purified from gel (5 µl), vector pT7 Blue (1 µl), distilled water (4 µl) and solution I (DNA Ligation Kit ver.2; Takara Bio, Japan) (10 µl) were mixed to prepare a ligation mixture, which was then incubated at 16° C. for 12 hours to thereby ligate the amplified product to the vector. *E. coli* JM109 strain was transformed in the same manner as described in (4) in Example 1. The recombinant vectors were recovered from the grown colonies. A recombinant vector in which the DNA fragment of the *E. coli* codon wild-type hydroxynitrile lyase gene was ligated to the expression vector correctly was confirmed.

(2) Analysis of DNA Nucleotide Sequence

An automated plasmid separation apparatus (Kurabo, Osaka, Japan) was used for preparing double-stranded DNA for use in sequencing. Plasmid DNA purified from the transformant obtained in (1) above were treated with EcoRI and XbaI, followed by analysis of the size of digested DNA on agarose gel. Plasmid No. 78 which showed a 0.9 kb DNA fragment was used as a template DNA for determination of nucleotide sequences. Analysis of nucleic acid sequences was performed with M13 Forward and Reverse IRD800 Infrared Dye Labeled primer (ALOKA) by the dideoxynucleotide chain termination method. Sequencing reaction was performed with Thermo Sequence Cycle Sequencing Kit (Amersham Bioscience; Uppsala, Sweden) and the reaction mixture was supplied to DNA Sequencer 4000L (Li-cor, Licon, Nebr., USA). It was confirmed that the genetic sequence of the *E. coli* codon wild-type hydroxynitrile lyase in plasmid No. 78 was identical with the genetic sequence of interest.

EXAMPLE 4

Preparation of *E. coli* Codon Wild-Type Hydroxynitrile Lyase Expression Vector

An SD sequence was added to the nucleotide sequence of the *E. coli* codon wild-type hydroxynitrile lyase gene obtained in Example 3 to obtain a DNA fragment, which was then inserted at the SphI-BamHI site of pUC19 to thereby prepare a pUC19-based *E. coli* codon wild-type hydroxynitrile lyase expression vector pUMESDsy, as described below. First, a modified DNA fragment encoding the *E. coli* codon wild-type hydroxynitrile lyase was prepared by PCR. The reaction mixture for PCR was composed of 5 µl of Pwo 10× buffer, 5 µl of dNTP mix, 0.5 µl of Pwo DNA polymerase, 36.2 µl of distilled water, 1 µl of sense and antisense primers, and 1 µl of plasmid No. 78 as a template. PCR was performed as follows: 95° C. for 2 minutes for denaturation, and 30 cycles of 94° C. for 30 sec, 50° C. for 30 sec and 72° C. for 2 minutes. The sense primer (SEQ ID NO: 58) consists of 61 nucleotides, and has an SphI recognition site, a ribosome binding site, the TAG termination codon for the lacZ gene frame of pUC19 and the ATG initiation codon for the hydroxynitrile lyase gene in its sequence. The antisense primer (SEQ ID NO: 59) consists of 37 nucleotides and has a BamHI recognition site in its sequence.

```
                                                         (SEQ ID NO: 58)
Sense primer:      tgcaaagcatgctaaggaggaatagaaaatggtgaccgcgcattttgtgctgattcatacc (SEQ ID NO: 59)
Antisense primer:  attttagtgcaattggatcctcacatgaaaatgtgag
```

The amplified PCR product obtained by PCR was digested with SphI and BamHI, separated by agarose gel electrophoresis, and then purified with QIAquick Gel Extraction Kit. This purified DNA fragment (5 µl), pUC19 (Takara Bio, Japan) (5 µl) predigested with SphI and BamHI, and solution I (DNA Ligation Kit ver.2; Takara Bio) (10 µl) were mixed to prepare a ligation mixture. This mixture was incubated at 16° C. for 12 hours to ligate the linker to the vector. *E. coli* JM109 strain was transformed in the same manner as described in (4) in Example 1. The recombinant vectors were recovered from the grown colonies. A plasmid in which the modified DNA fragment (SphI-BamHI fragment) comprising the *E. coli* codon wild-type hydroxynitrile lyase gene was inserted correctly downstream of the lac promoter of pUC19 was designated expression vector pUMESDsy.

EXAMPLE 5

Preparation of Expression Vector for Improved Hydroxynitrile Lyase in Which the Amino Acid at Position 2 is Substituted, and Hydroxynitrile Lyase-Expressing Transformant Comprising the Vector (1) Preparation of Expression Vector for Improved Hydroxynitrile Lyase in Which the Amino Acid at Position 2 is Substituted, and Hydroxynitrile Lyase-Expressing Transformant Comprising the Vector (Part 1)

Hydroxynitrile lyase genes in which the amino acid valine (Val; V) at position 2 of the cassava (*Manihot esculenta*)-derived wild-type hydroxynitrile lyase is substituted with alanine (Ala; A), aspartic acid (Asp; D), glutamic acid (Glu; E), glycine (Gly; G), isoleucine (Ile; I), methionine (Met; M), threonine (Thr; T), asparagine (Asn; N), lysine (Lys; K), serine (Ser; S), phenylalanine (Phe; F), tyrosine (Tyr; Y), cysteine (Cys; C) or tryptophan (Trp; W) were prepared by introducing, at the time of PCR amplification, into a sense primer a restriction enzyme recognition site (which is at the same time a codon encoding an amino acid of interest) capable of ligating to the NcoI restriction site on the above-described expression vector pKK233-2(+Sse).

PCR reaction mixture was composed of 5 µl of Pwo 10× buffer, 5 µl of dNTP mix, 0.5 µl of Pwo DNA polymerase, 36.2 µl of distilled water, 1 µl of sense and antisense primers, and 1 µl of pUME as a template. PCR was performed as follows: 95° C. for 2 minutes for denaturation, and 30 cycles of 94° C. for 30 sec, 50° C. for 30 sec and 72° C. for 2 minutes. For sense primers, the following oligonucleotides were used.

OXYN-32: agaccatggc tactgcacat tttgtt (SEQ ID NO: 60; this sequence consists of 26 nucleotides, and has an NcoI recognition site and the ATG initiation codon and subsequent several codons of the hydroxynitrile lyase gene; the codon corresponding to the amino acid at position 2 is GCT and encodes alanine.)

OXYN-33: agaccatgga cactgcacat tttgtt (SEQ ID NO: 61; this sequence consists of 26 nucleotides, and has an NcoI recognition site and the ATG initiation codon and subsequent several codons of the hydroxynitrile lyase gene; the codon corresponding to the amino acid at position 2 is GAC and encodes aspartic acid.)

OXYN-34: agaccatgga aactgcacat tttgtt (SEQ ID NO: 62; this sequence consists of 26 nucleotides and has an NcoI recognition site and the ATG initiation codon and subsequent several codons of the hydroxynitrile lyase gene; the codon corresponding to the amino acid at position 2 is GAA and encodes glutamic acid.)

OXYN-35: agaccatggg cactgcacat tttgtt (SEQ ID NO: 63; this sequence consists of 26 nucleotides, and has an NcoI recognition site and the ATG initiation codon and subsequent several codons of the hydroxynitrile lyase gene; the codon corresponding to the amino acid at position 2 is GGC and encodes glycine.)

OXYN-10: atttccatca tgatcactgc acattttgtt ctg (SEQ ID NO: 64; this sequence consists of 33 nucleotides, and has a BspHI recognition site and the ATG initiation codon and subsequent several codons of the hydroxynitrile lyase gene; the codon corresponding to the amino acid at position 2 is ATC and encodes isoleucine.)

OXYN-36: agatcatgat gactgcacat tttgttc (SEQ ID NO: 65; this sequence consists of 27 nucleotides, and has a BspHI recognition site and the ATG initiation codon and subsequent several codons of the hydroxynitrile lyase gene; the codon corresponding to the amino acid at position 2 is ATG and encodes methionine.)

OXYN-37: agatcatgac cactgcacat tttgtt (SEQ ID NO: 66; this sequence consists of 26 nucleotides, and has a BspHI recognition site and the ATG initiation codon and subsequent several codons of the hydroxynitrile lyase gene; the codon corresponding to the amino acid at position 2 is ACC and encodes threonine.)

OXYN-38: agatcatgaa cactgcacat tttgttc (SEQ ID NO: 67; this sequence consists of 27 nucleotides, and has a BspHI recognition site and the ATG initiation codon and subsequent several codons of the hydroxynitrile lyase gene; the codon corresponding to the amino acid at position 2 is AAC and encodes asparagine.)

OXYN-39: agatcatgaa aactgcacat tttgttc (SEQ ID NO: 68; this sequence consists of 27 nucleotides, and has a BspHI recognition site and the ATG initiation codon and subsequent several codons of the hydroxynitrile lyase gene; the codon corresponding to the amino acid at position 2 is AAA and encodes lysine.)

OXYN-40: agatcatgag cactgcacat tttgtt (SEQ ID NO: 69; this sequence consists of 26 nucleotides, and has a BspHI recognition site and the ATG initiation codon and subsequent several codons of the hydroxynitrile lyase gene; the codon corresponding to the amino acid at position 2 is AGC and encodes serine.)

OXYN-41: agaacatgtt cactgcacat tttgttc (SEQ ID NO: 70; this sequence consists of 27 nucleotides, and has a PciI recognition site and the ATG initiation codon and subsequent several codons of the hydroxynitrile lyase gene; the codon corresponding to the amino acid at position 2 is TTC and encodes phenylalanine.)

OXYN-42: agaacatgta cactgcacat tttgttc (SEQ ID NO: 71; this sequence consists of 27 nucleotides, and has a PciI recognition site and the ATG initiation codon and subsequent several codons of the hydroxynitrile lyase gene; the codon corresponding to the amino acid at position 2 is TAC and encodes tyrosine.)

OXYN-43: agaacatgtg cactgcacat tttgttc (SEQ ID NO: 72; this sequence consists of 27 nucleotides, and has a PciI recognition site and the ATG initiation codon and subsequent several codons of the hydroxynitrile lyase gene; the codon corresponding to the amino acid at position 2 is TGC and encodes cysteine.)

OXYN-44: agaacatgtg gactgcacat tttgttc (SEQ ID NO: 73; this sequence consists of 27 nucleotides, and has a PciI recognition site and the ATG initiation codon and subsequent several codons of the hydroxynitrile lyase gene; the codon corresponding to the amino acid at position 2 is TGG and encodes tryptophan.)

As the antisense primer, OXYN-09 used in (2) in Example 2 was used.

The thus amplified PCR products were double-digested. For mutants substituted with alanine, aspartic acid, glutamic acid and glycine, restriction enzymes NcoI and Sse8387I were used. For mutants substituted with isoleucine, methionine, threonine, asparagine, lysine and serine, restriction enzymes BspHI and Sse8387I were used. For mutants substituted with phenylalanine, tyrosine, cysteine and tryptophan, restriction enzymes PciI and Sse8387I were used. It should be note that digestion with NcoI was partial digestion. After separation by agarose gel electrophoresis, a band comprising the full length hydroxynitrile lyase gene (about 0.8 kb) was purified with QIAquick Gel Extraction Kit. The purified DNA fragment of hydroxynitrile lyase gene (5 µl each) and the expression vector pKK233-2(+Sse) (5 µl) prepared in (2) in Example 2 were mixed. Solution I (DNA Ligation Kit ver.2; Takara Bio) (10 µl) was further added to the mixture to prepare a ligation mixture. This mixture was incubated at 16° C. for 12 hours to thereby ligate the linker to the vector. E. coli JM109 strain was transformed in the same manner as described in (4) in Example 1. The recombinant vectors were recovered from the grown colonies. Expression-type recombinant vectors in which the DNA fragment of the hydroxynitrile lyase gene was ligated to the expression vector correctly were confirmed. The recombinant vectors comprising genes encoding hydroxynitrile lyases in which the amino acid at position 2 is substituted with alanine, aspartic acid, glutamic acid, glycine, isoleucine, methionine, threonine, asparagine, lysine, serine, phenylalanine, tyrosine, cysteine and tryptophan were designated pOXN103V2A, pOXN103V2D, pOXN103V2E, pOXN103V2G, pOXN103V2I, pOXN103V2M, pOXN103V2T, pOXN103V2N, pOXN103V2K, pOXN103V2S, pOXN103V2F, pOXN103V2Y, pOXN103V2C and pOXN103V2W, respectively. At the same time, transformants expressing the individual hydroxynitrile lyases, respectively, were also obtained: JM109/pOXN103V2A, JM109/pOXN103V2D, JM109/pOXN103V2E, JM109/pOXN103V2G, JM109/pOXN103V2I, JM109/pOXN103V2M, JM109/pOXN103V2T, JM109/pOXN103V2N, JM109/pOXN103V2K, JM109/pOXN103V2S, JM109/pOXN103V2F, JM109/pOXN103V2Y, JM109/pOXN103V2C and JM109/pOXN103V2W.

(2) Preparation of Expression Vector for Improved Hydroxynitrile Lyase in Which the Amino Acid at Position 2 is Substituted, and Hydroxynitrile Lyase-Expressing Transformant Comprising the Vector (Part 2)

Hydroxynitrile lyase genes in which the amino acid valine (Val; V) at position 2 of the cassava (*Manihot esculenta*)-derived wild-type hydroxynitrile lyase is substituted with arginine (Arg; R), glutamine (Gln; Q), histidine (His; H), leucine (Leu; L) or proline (Pro; P) were prepared by site-directed mutagenesis with QuikChange™ Site-Directed Mutagenesis Kit (Stratagene) using the wild-type hydroxynitrile lyase expression vector pOXN 103 prepared in (2) in Example 2 as a template. Primers used for introducing mutations were as follows.

Arginine Substitution Mutant

OXYN-45: aaacagacca tgcgtactgc acattttg (SEQ ID NO: 74; this is a sense primer consisting of 28 nucleotides and has a complementary sequence to OXYN-46; the codon corresponding to the amino acid at position 2 is CGT and encodes arginine.)

OXYN-46: caaaatgtgc agtacgcatg gtctgttt (SEQ ID NO: 75; this is an antisense primer consisting of 28 nucleotides and has a complementary sequence to OXYN-45.)

Glutamine Substitution Mutant

OXYN-47: aaacagacca tgcagactgc acattttg (SEQ ID NO: 76; this is a sense primer consisting of 28 nucleotides and has a complementary sequence to OXYN-48; the codon corresponding to the amino acid at position 2 is CAG and encodes glutamine.)

OXYN-48: caaaatgtgc agtctgcatg gtctgttt (SEQ ID NO: 77; this is an antisense primer consisting of 28 nucleotides and has a complementary sequence to OXYN-47.)

Histidine Substitution Mutant

OXYN-49: aaacagacca tgcacactgc acattttg (SEQ ID NO: 78; this is a sense primer consisting of 28 nucleotides and has a complementary sequence to OXYN-50; the codon corresponding to the amino acid at position 2 is CAC and encodes histidine.)

OXYN-50: caaaatgtgc agtgtgcatg gtctgttt (SEQ ID NO: 79; this is an antisense primer consisting of 28 nucleotides and has a complementary sequence to OXYN-49.)

Leucine Substitution Mutant

OXYN-51: aaacagacca tgctgactgc acattttg (SEQ ID NO: 80; this is a sense primer consisting of 28 nucleotides and has a complementary sequence to OXYN-52; the codon corresponding to the amino acid at position 2 is CTG and encodes leucine.)

OXYN-52: caaaatgtgc agtcagcatg gtctgttt (SEQ ID NO: 81; this is an antisense primer consisting of 28 nucleotides and has a complementary sequence to OXYN-51.)

Proline Substitution Mutant

OXYN-53: aaacagacca tgccgactgc acattttg (SEQ ID NO: 82; this is a sense primer consisting of 28 nucleotides and has a complementary sequence to OXYN-54; the codon corresponding to the amino acid at position 2 is CCG and encodes proline.)

OXYN-54: caaaatgtgc agtcggcatg gtctgttt (SEQ ID NO: 83; this is an antisense primer consisting of 28 nucleotides and has a complementary sequence to OXYN-53.)

According to the protocol of the above-mentioned Kit, extension reaction and DpnI treatment were performed. Then, *E. coli* JM109 was transformed, followed by recovery of plasmid DNA from grown colonies. Plasmids in which the DNA fragment of the hydroxynitrile lyase gene was ligated to the expression vector correctly were confirmed. Expression vectors comprising the genes encoding hydroxynitrile lyases in which the amino acid at position 2 is substituted with arginine, glutamine, histidine, leucine and proline were designated pOXN103V2R, pOXN103V2Q, pOXN103V2H, pOXN103V2L and pOXN103V2P, respectively. At the same time, transformants JM109/pOXN103V2R, JM109/pOXN103V2Q, JM109/pOXN103V2H, JM109/pOXN103V2L and JM109/pOXN103V2P expressing the individual hydroxynitrile lyases were also obtained.

EXAMPLE 6

Evaluation of Expression Levels on Transformants Expressing Improved Hydroxynitrile Lyases in which the Amino Acid at Position 2 is Substituted (1) Preparation of Cell Extracts Of the transformants expressing the improved hydroxynitrile lyases in which the amino acid at position 2 is substituted prepared in (1) and (2) in Example 5, transformants carrying pOXN103V2K, pOXN103V2N, pOXN103V2I, pOXN103V2R, pOXN103V2Q, pOXN103V2P, pOXN103V2T, pOXN103V2Y, pOXN103V2L, pOXN103V2M, pOXN103V2S, pOXN103V2E, pOXN103V2A, pOXN103V2G and pOXN103V2D were cultured in the medium described below (100 ml in 500 ml Erlenmeyer flask) at 37° C. for 24 hours.

| Medium Composition | |
|---|---|
| Peptone | 10 g/L |
| Yeast extract | 5 g/L |
| NaCl | 10 g/L |
| Ampicillin | 50 mg/L |
| IPTG | 1 mM (final concentration) |

As a control, the wild-type hydroxynitrile lyase expression vector-introduced transformant JM109/pOXN103 obtained in (2) in Example 2 was cultured in the same manner.

Cells were harvested from the resultant culture by centrifugation (3,700×g, 10 minutes, 4° C.), washed with 10 mM sodium phosphate buffer (pH 7.0) and suspended in 10 ml of the same buffer. The resultant cell suspension (1 ml) was disrupted with a sonicator VP-15S (Taitec, Japan) for 3 minutes under the following conditions: output control 4, DUTY CYCLE 40%, PULS, TIMER=B mode 10s, while ice-cooling. The disrupted cell suspension was used as the total fraction of cell extract.

(2) Analysis of Expression Levels by Polyacrylamide Gel Electrophoresis

Figure 3:
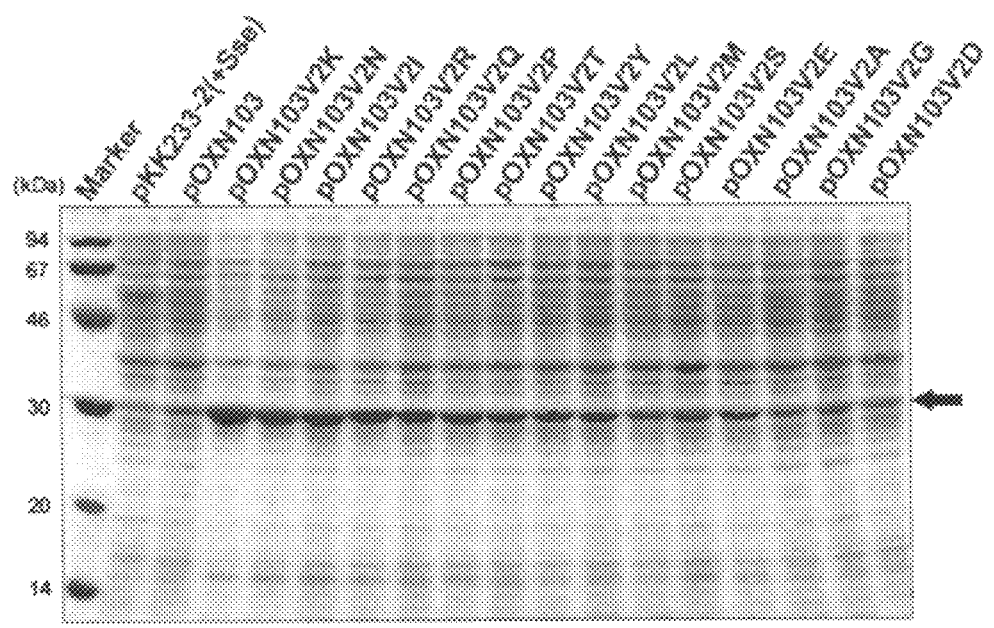
FIG. 3 is a diagram showing the comparative analysis by SDS-PAGE of expression levels of hydroxynitrile lyase protein in an empty vector-introduced transformant (JM109/pKK233-2(+Sse)); a wild-type hydroxynitrile lyase-expressing transformant (JM109/pOXN103); and hydroxynitrile lyase-expressing transformants in which the 2nd amino acid is substituted (pOXN103V2K, pOXN103V2N, pOXN103V2I, pOXN103V2R, pOXN103V2Q, pOXN103V2P, pOXN102V2T, pOXN103V2Y, pOXN103V2L, pOXN103V2M, pOXN103V2S, pOXN103V2E, pOXN103V2A, pOXN103V2G and pOXN103V2D) in Example 6. The arrow mark indicates the band of hydroxynitrile lyase protein.

The total fraction of cell extract obtained in (1) above was diluted with 10 mM sodium phosphate buffer (pH 7.0) to give a concentration of OD630=12.5 as calculated for the cell density in the culture broth. The diluted total fraction of cell extract from each *E. coli* clone was mixed with an equal amount of polyacrylamide gel electrophoresis sample buffer (0.1M Tris-HCl (pH 6.8), 4% w/v SDS, 12% v/v β-mercaptoethanol, 20% v/v glycerol, trace bromophenol blue), followed by boiling for 5 minutes for denaturation. 10% polyacrylamide gel was prepared, and the denatured sample was applied thereto (5 µl per lane) and electrophoresed (FIG. 3). Each hydroxynitrile lyase was observed as an approx. 30 kDa band (the arrow mark in FIG. 3). With JM109/pKK233-2(+Sse) carrying only an empty vector as background, the thickness of bands corresponding to mutant hydroxynitrile lyases were compared with that of the band of the wild-type hydroxynitrile lyase-expressing transformant JM109/pOXN103 using an analysis software Image-Pro Plus Ver 4.5 (Planetron). As a result, relative values as shown in Table 5 were obtained. It was demonstrated that improved hydroxynitrile lyases with greatly enhanced expression levels can be obtained by substituting the amino acid at position 2 with another amino acid.

According to the relationship between the amino acid at position 2 and formylmethionine processing, and the N-end rule, it is said that there is no significant difference in the stability of protein when comparing a protein which has valine at position 2 and a protein which has isoleucine at position 2. Therefore, the above-described improvement effect on expression level cannot be explained by those relationship and rule. It is believed that this improvement effect is resulting from a thoroughly new principle.

TABLE 5

Relative Ratio of Band Thickness of Improved Hydroxynitrile Lyases

| Expression plasmid | Hydroxynitrile lyase | Relative ratio of band thickness (%) |
|---|---|---|
| pOXN103 | wild-type | 100 |
| pOXN103V2K | V2K | 736 |
| pOXN103V2N | V2N | 567 |
| pOXN103V2I | V2I | 560 |
| pOXN103V2R | V2R | 446 |

TABLE 5-continued

Relative Ratio of Band Thickness of Improved Hydroxynitrile Lyases

| Expression plasmid | Hydroxynitrile lyase | Relative ratio of band thickness (%) |
|---|---|---|
| pOXN103V2Q | V2Q | 349 |
| pOXN103V2P | V2P | 365 |
| pOXN103V2T | V2T | 313 |
| pOXN103V2Y | V2Y | 264 |
| pOXN103V2L | V2L | 294 |
| pOXN103V2M | V2M | 190 |
| pOXN103V2S | V2S | 314 |
| pOXN103V2E | V2E | 155 |
| pOXN103V2A | V2A | 120 |
| pOXN103V2G | V2G | 138 |
| pOXN103V2D | V2D | 105 |

EXAMPLE 7

Activity Evaluation on Transformants Expressing Improved Hydroxynitrile Lyases in Which the Amino Acid at Position 2 is Substituted Of the transformants expressing the improved hydroxynitrile lyases in which the amino acid at position 2 is substituted prepared in (1) and (2) in Example 5, transformants carrying pOXN103V2K, pOXN103V2N, pOXN103V2I, pOXN103V2R and pOXN103V2Q were cultured in the same manner as described in (1) in Example 6 except that they were cultured at 30° C. for 24 hours. As a control, the wild-type hydroxynitrile lyase expression vector-introduced transformant JM109/pOXN103 obtained in (2) in Example 2 was cultured in the same manner. From the resultant culture, the total fraction of cell extract was obtained in the same manner as described in (1) in Example 6 and then centrifuged (10,000×g, 5 minutes, 4° C.). The resultant supernatant was collected as the soluble fraction of cell extract. Using the thus obtained soluble fraction of cell extract, hydroxynitrile lyase activity was measured according to the method disclosed in Japanese Unexamined Patent Publication No. 11-508775. Briefly, the activity was measured by tracing the generation of benzaldehyde from racemic mandelonitrile. The enzyme solution (50 µl) was mixed with 50 mM sodium citrate buffer (pH 5.0) (900 µl). A substrate solution (100 µl) (37.5 mM racemic mandelonitrile/10 mM sodium citrate buffer (pH 3.5)) was added to the above mixture, and the measurement of activity was started. Increase in absorbance at 280 nm was traced for 5 minutes (as a control, measurement was performed on an enzyme-free substrate solution). 1 U corresponds to the amount of enzyme that catalyzes conversion of racemic mandelonitrile to 1 µmol benzaldehyde per minute under the above-described conditions. Further, quantitative determination of the protein in the soluble fraction was performed with Bio-Rad Protein Assay (Bio-Rad) according to the protocol attached thereto. As a result, specific activities per mg of protein in cell extract soluble fraction were 22.7 U/mg protein for JM109/pOXN103V2K-derived protein; 8.1 U/mg protein for JM109/pOXN103V2N-derived protein; 5.5 U/mg protein for JM109/pOXN103V2I-derived protein; 7.8 U/mg protein for JM109/pOXN103V2R-derived protein; and 4.5 U/mg protein for JM109/pOXN103V2Q-derived protein. On the other hand, the specific activity per mg of protein in cell extract soluble fraction of the wild-type hydroxynitrile lyase expression vector-introduced transformant JM109/pOXN103 was 2.7 U/mg protein. Thus, it was confirmed that the specific activities per protein in cell extract of improved hydroxynitrile lyases obtained by substituting the amino acid at position 2 with another amino acid are greatly improved compared to the activity of protein from the wild-type hydroxynitrile lyase expression vector-introduced transformant.

EXAMPLE 8

Random Mutagenesis by Error Prone PCR and Screening (1) Error Prone PCR (1 st)

Error prone PCR was performed using as a template the *E. coli* codon wild-type hydroxynitrile lyase expression vector pUMESDsy prepared in Example 4.

With respect to the conditions of the error prone PCR, the quantities of $MgCl_2$ and $MnCl_2$ were increased in the reaction solution. Table 6 shows the composition of the PCR reaction solution.

TABLE 6

| Composition of Error Prone PCR Reaction Solution | |
|---|---|
| Template DNA (pUMESDsy) | 1 (µl) |
| Primer M13-reverse | 1 |
| M13-forward | 1 |
| 10× Buffer (for Taq) (not containing $MgCl_2$) | 5 |
| 10 mM dATP | 1 |
| 10 mM dCTP | 5 |
| 10 mM dGTP | 1 |
| 10 mM dTTP | 5 |
| Taq DNA polymerase | 2.5 |
| 25 mM $MgCl_2$ | 15 |
| 5 mM $MnCl_2$ | 10 |
| $H_2O$ | 2.5 |
| Total | 50 (µl) |

The sequences of the above-mentioned primers are as follows.

```
M13-reverse:  aacagctatgaccatg   (SEQ ID NO: 84)
M13-forward:  gtaaaacgacggccagt  (SEQ ID NO: 85)
```

The reaction conditions of PCR were as described in Table 7 below.

TABLE 7

| Reaction Conditions of Error Prone PCR | |
|---|---|
| 95° C. | 5 min |
| 95° C. | 30 sec |
| 55° C. | 1 min 30 sec  × 30 cycles |
| 72° C. | 1 min |
| 72° C. | 10 min |
| 4° C. | forever |

The resultant PCR products were extracted from agarose gel using Gel Extraction System (VIOGENE).

The amplified DNAs and vector pUC19 were treated with BamHI and SphI, and then electrophoresed. From the electrophoresis gel, the amplified DNAs and vector pUC19 were recovered by extraction and ligated. With the ligation solution, *E. coli* JM109 strain was transformed to obtain transformants. Master plates of mutant colonies were prepared and used in the subsequent experiment.

(2) Screening of the Mutants Obtained by Error Prone PCR

From the mutants obtained in (1), those with improved activity were screened. The activity was determined by measuring mandelonitrile (substrate) degrading activity in the cell extract soluble fraction prepared from cultured cells expressing mutants, using the amount of benzaldehyde generated as an indicator.

(2-1) Sample Preparation

Samples were prepared using 96-well plates. Into 0.8 ml 96-well sterilized plates (ABgene), LB medium (containing 80 μg/ml Amp and 0.1 mM IPTG) were dispensed at 150 μl/well. Then, mutant colonies were seeded therein from the master plate. The 96-well plate was subjected to shake culture at 37° C. at 1,200 rpm for 12 hours with BioShaker (M-BR-024, TAITEC). After cultivation, the culture broth was centrifuged (5,000 rpm, 10 min, 4° C., himac CR20, rotor R6S; Hitachi) to harvest the cells. After removal of the supernatant, the plate was placed upside down on newspaper to remove the medium as much as possible. The resultant cells were suspended in 100 μl of 0.85% NaCl using BioShaker. Then, this suspension was transferred into a 96-well U-bottom plate (Corning). Subsequently, the cells were harvested by centrifugation (4,500 rpm, 10 min, 4° C., himac CR20, rotor R6S; Hitachi) and the supernatant was removed. The plate was placed upside down on newspaper to remove moisture content as much as possible. To the resultant cells, 5 μl of lysozyme solution [10 mg/ml lysozyme (derived from egg white; Seikagaku Corporation), 100 mM KPB (pH 7.0), 10 mM EDTA] was added and suspended with a TUPLE MIXER (speed 7; IWAKI). The suspension was incubated at 37° C. for 1 hour to perform lysozyme treatment to thereby make $E.\ coli$ into protoplast. The resultant $E.\ coli$ was subjected to freeze/thaw treatment at −40° C. and 37° C. To the resultant cells, 100 μl of a hypotonic solution (10 mM KPB (pH 7.0), 5 mM $MgCl_2$) was added for lysis. The resultant solution was centrifuged (4,500 rpm, 10 minutes, 4° C., himac CR20, rotor R6S; HITACHI) to thereby precipitate $E.\ coli$ genome and cell walls, etc. The resultant supernatant was collected as a crude enzyme solution and used in the subsequent experiment.

Alternatively, transformants expressing mutants were cultured, and the cultured cells were washed with phosphate buffer (pH 7) and disrupted by sonication to thereby obtain the total fraction of cell extract. The liquid containing disrupted cells was centrifuged, and the resultant supernatant was collected as the soluble fraction of cell extract. The precipitate was suspended in phosphate buffer (pH 7.0) in an amount equal to that of supernatant to thereby obtain the insoluble fraction of cell extract.

(2-2) Activity Measurement

The activity to degrade mandelonitrile (a substrate for hydroxynitrile lyase) was determined by measuring the amount of benzaldehyde generated. The reaction composition is shown in Table 8 below.

TABLE 8

| Reaction Composition | | |
|---|---|---|
| | | Final concentration |
| 100 mM Na-citrate buffer (pH 5.4) | 100 (μl) | 50 mM |
| 10 mM racemic mandelonitrile | 80 | 4 mM |
| Enzyme solution (crude enzyme solution, soluble fraction of cell extract) | 10 | |
| DIW | 10 | |
| Total | 100 (μl) | |

For activity measurement, sodium citrate buffer was added to 96-well UV plates (Greiner Bio-One) and its temperature was adjusted to 25° C. Then, the crude enzyme solution was added thereto and suspended by pipetting. Subsequently, racemic mandelonitrile was added thereto, followed by pipetting and shaking. Then, increase in absorbance at 280 nm in wavelength was measured at 25° C. for 10 minutes using a microplate reader (GENios; Tecan Japan). For analysis, LS-PLATE manager 2001 (Win) (Wako Purechemical) was used.

(2-3) Results of Screening

Screening was performed using, as a positive control, pUMESDsy or the sample used as a template for PCR and, as a negative control, pUC19. Specifically, 11 samples showing higher activity than the positive control were selected from approx. 5,000 colonies of the obtained mutants. Each of these 11 samples was cultured on a 3 ml scale to allow expression of hydroxynitrile lyase. Then, synthesis activity was determined by measuring production of (S)-mandelonitrile from benzaldehyde. The standard assay solution contains 300 mM citrate buffer (pH 4.0), 50 mM benzaldehyde and 100 mM cyanide solution in its final volume of 0.9 ml. The reaction was immediately started by adding 100 μl of enzyme solution and the reaction solution was incubated at 25° C. for 120 minutes. The reaction was terminated by adding 100 μl of sampled reaction solution to 900 μl of organic solvent (hexane:isopropanol=9:1). Then, the supernatant obtained by centrifugation (15,000×g, 10 minutes, 4° C.) was assayed by HPLC. The amounts of individual components were measured by feeding to CHIRALCEL OJ-H column (Daicel Chemical) at a flow rate of 1.0 ml/minute using hexane:isopropanol=90:10 as a mobile phase. The column temperature was set at 30° C. and absorbance was measured at 254 nm. From the resultant standard curves, the amount of individual components were calculated. The amount of enzyme which generates 1 μmol S-mandelonitrile from benzaldehyde per minute under standard assay conditions was defined as 1 unit of enzyme activity.

After the measurement, samples which exhibited remarkably high activity compared to the positive control were selected. These samples were subjected to SDS-PAGE to confirm the yield of soluble fraction, and further subjected to DNA sequence analysis to confirm the introduction of mutations.

Figure 4:
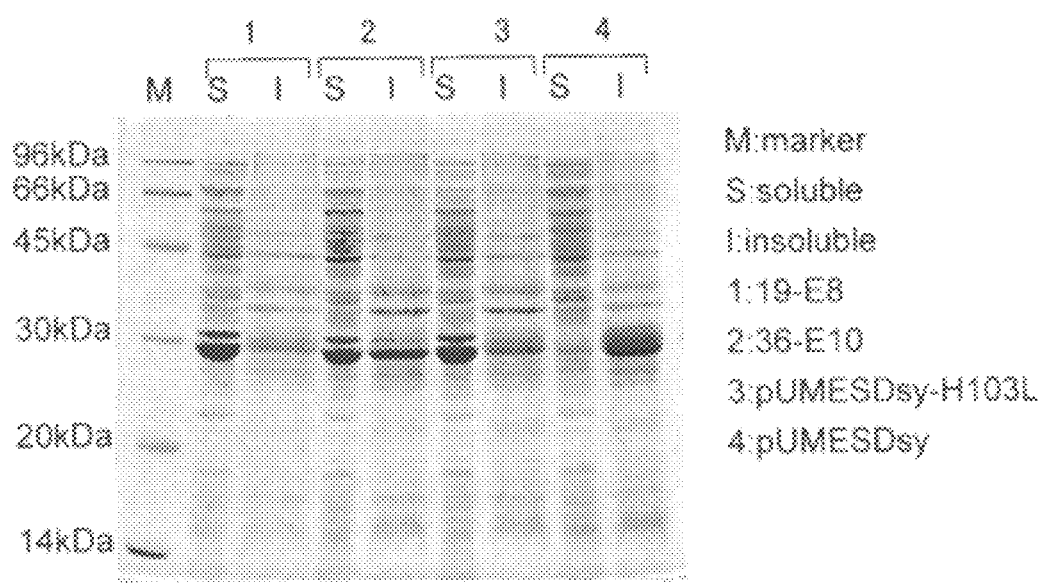
FIG. 4 is a diagram showing the results of SDS-PAGE analysis on cell extract soluble fractions (S) and insoluble fractions (I) prepared respectively from random mutant-expressing transformants (19-E8 and 36-E10) obtained from the second Error Prone PCR using as templates random mutant-expressing transformants (JM109/pUIVIESDsy-H103L and pUMESDsy-H103L) obtained from the first Error Prone PCR using as templates *E. coli* codon wild-type hydroxynitrile lyase-expressing transformants (JM109/pUMESDsy and pUMESDsy) in Example 8.

Of the 11 samples used, the sample with the highest activity exhibited approx. 10-fold synthesis activity (63.3 U/ml) compared to pUMESDsy; the results of SDS-PAGE revealed that most of the expressed hydroxynitrile lyase existed in the soluble fraction (Table 9 and FIG. 4). Sequence analysis confirmed that this increase in activity is resulted from one amino acid substitution from His103 to Leu103. The resultant mutant plasmid was designated pUMESDsy-H103L.

(3) Random Mutations by Error Prone PCR (2nd)

Using pUMESDsy-H103L obtained in (2) above as a template, error prone PCR was performed again. The hydroxynitrile lyase synthesis activities (U/ml) of pUMESDsy (used in the 1st error prone PCR as a template), mutant clone pUMESDsy (obtained in the 1st error prone PCR), and random mutant clones 19-E8 and 36-E10 (obtained in the 2nd error prone PCR using pUMESDsy-H103L as a template) are shown in Table 9 below.

TABLE 9

| (S)-HNL Synthesis Activities of Random Mutants | | | | |
|---|---|---|---|---|
| | 19-E8 | 36-E10 | pUMESDsy-H103L | pUMESDsy |
| Crude enzyme | 74.4 | 60.1 | 63.3 | 4.1 |
| | | | | (U/ml) |

As a result of the error prone PCR using pUMESDsy-H103L as a template, the resultant clone 19-E8 exhibited further rise in activity (Table 9) and further increase of yield of soluble fraction (FIG. 4). The results of sequence analysis revealed that this clone 19-E8 has the following three mutations introduced thereinto: His103(cat)→Leu(ctt), Phe125 (ttt)→Leu(ctt) and Thr146(acc)→Thr(aca) (two amino acid substitutions, three nucleotide mutations). Further, clone 36-E10 which exhibited less activity increase than the template has the following three mutations introduced thereinto: His103(cat)→Leu(ctt), Thr205(acc)→Ser(tcc) and Asp235 (gat)→Gly(ggt) (three amino acid substitutions, three nucleotide mutations).

EXAMPLE 9

Introduction of H103L Substitution into Wild-Type Hydroxynitrile Lyase Gene

Plasmid pUMESD-H103L was constructed by mutating the expression vector pUMESD comprising the plant codon wild-type hydroxynitrile lyase gene prepared in (1) in Example 2 so that the histidine (His, H) at position 103 is substituted with leucine (Leu, L). This site-directed mutagenesis was performed using QuickChange Site-Directed Mutagenesis Kit (STRATAGENE).

PCR reaction conditions are shown in Table 10 below.

TABLE 10

Composition of PCR Reaction Solution

| | |
|---|---|
| 10× reaction Buffer | 5 (μl) |
| Template DNA (pUMESD) | 1 |
| 5'-primer | 1.25 |
| 3'-primer | 1.25 |
| dNTP mix | 1 |
| $H_2O$ | 39.5 |
| Pfu Turbo DNA polymerase | 1 |
| Total | 50 (μl) |

The sequence of the above primer (5'-primer) is as described below.

```
                                    (SEQ ID NO: 86)
OXYN-30:    gctggtgttttcctgaattccttattgcc
```

The sequence of the above primer (3'-primer) is as described below.

```
                                    (SEQ ID NO: 87)
OXYN-31:    ggcaataaggaattcaggaaaacaccagc
```

OXYN-30 (SEQ ID NO: 86) is a sense primer consisting of 29 nucleotides and has a complementary sequence to OXYN-31. The codon corresponding to the amino acid at position 103 is CTG and encodes leucine. OXYN-31 (SEQ ID NO: 87) is an antisense primer consisting of 29 nucleotides and has a complementary sequence to OXYN-30.

PCR reaction conditions are as shown in Table 11 below.

TABLE 11

PCR Reaction Conditions

| | |
|---|---|
| 95° C. | 30 sec |
| ↓ | |
| 95° C. | 30 sec ⎫ |
| 55° C. | 1 min ⎬ ×12 cycles |
| 68° C. | 4 min ⎭ |
| ↓ | |
| 4° C. | forever |

In order to introduce H103L mutation into pUMESD, site-directed mutagenesis (single amino acid substitution) was performed by PCR using the above primers (OXYN-30 and OXYN-31). One μl of DpnI was added to 50 μl of PCR reaction solution, which was then incubated at 37° C. for 1 hour. By this treatment, the template DNA was digested and only those plasmids into which the mutation had been introduced were obtained. Using the DpnI-treated PCR reaction solution, E. coli JM109 strain was transformed in the same manner as described in (4) in Example 1. Recombinant vectors were recovered from grown colonies. The recombinant vector comprising the plant codon wild-type hydroxynitrile lyase gene into which H103L mutation is introduced was designated pUMESD-H103L.

The hydroxynitrile lyase activity of pUMESDsy-H103L obtained in Example 8 and the hydroxynitrile lyase activity (synthesis activity) of the above-described pUMESD-H103L were compared. The measurement of hydroxynitrile lyase synthesis activity was performed based on the method as described in Example 8. With respect to cultivation, IPTG was added to the culture simultaneously with the start of cultivation to give a final concentration of 0.1 mM. Cells were cultured at 37° C. for 12 hours and then harvested.

The hydroxynitrile lyase synthesis activities (U/ml) of the following four samples are shown in Table 12: plasmid pUMESDsy comprising the E. coli codon wild-type hydroxynitrile lyase gene, plasmid pUMESD comprising the plant codon wild-type hydroxynitrile lyase gene, and plasmids pUMESDsy-H103L and pUMESD-H103L obtained by introducing H103L substitution into those plasmids as templates. The results revealed that the H103L substitution mutant of plant codon hydroxynitrile lyase gene (pUMESD-H103L) exhibited increase in enzyme activity (Table 12) and yield increase in soluble fraction (FIG. 5) as seen in the corresponding mutant of E. coli codon gene.

TABLE 12

(S)-HNL Synthesis Activities of Amino Acid Substitution Mutants

| | E. coli codon | | Plant codon | |
|---|---|---|---|---|
| | pUMESDsy-H103L | pUMESDsy | pUMESD-H103L | pUMESD |
| Crude enzyme | 56.3 | 5.7 | 59.5 | 4.3 |

(U/ml)

EXAMPLE 10

All Amino Acid Substitution at H103 Residue in *E. coli* and Plant Codon Wild-Type Hydroxynitrile Lyase Genes (1) Preparation of H103 Substitution Mutants Random primers which change the amino acid residue at position 103 into 20 essential amino acids were designed in both *E. coli* and plant codon wild-type hydroxynitrile lyase genes and used for preparing mutants. PCR reaction conditions are shown in Table 13 below.

TABLE 13

Composition of PCR Reaction Solution

| | |
|---|---|
| 10 × reaction Buffer | 5 (μl) |
| Template DNA (pUMESDsy, pUMESD) | 1 |
| 5'-primer | 1.25 |
| 3'-primer | 1.25 |
| dNTP mix | 1 |
| H$_2$O | 39.5 |
| Pfu Turbo DNA polymerase | 1 |
| Total | 50 (μl) |

The sequences for the above primer (5'-primer) are as described below.

```
H103-20aa-F:
    (SEQ ID NO: 88; for use in amplifying E.
    coli codon wild-type hydroxynitrile lyase gene)
ggcgggcgtttttnnsaacagcctgctgcc ME-H103-20aa-F:
    (SEQ ID NO: 89; for use in amplifying plant
    codon wild-type hydroxynitrile lyase gene)
gcagctggtgttttcnnsaattccttattgccagacaccg
```

The sequences for the above primer (3'-primer) are as described below.

```
H103-20aa-R:
    (SEQ ID NO: 90; for use in amplifying E.
    coli codon wild-type hydroxynitrile lyase gene)
ggcagcaggctgttsnnaaaaacgcccgcc ME-H103-20aa-R:
    (SEQ ID NO: 91; for use in amplifying plant
    codon wild-type hydroxynitrile lyase gene)
cggtgtctggcaataaggaattsnngaaaacaccagctgc
```

In the above primer sequences, n is a, t, g or c.
PCR reaction conditions are as shown in Table 14 below.

TABLE 14

PCR Reaction Conditions

| | |
|---|---|
| 95° C. | 30 sec |
| 95° C. | 30 sec ⎫ |
| 55° C. | 1 min ⎬ × 12 cycles |
| 68° C. | 4 min ⎭ |
| 4° C. | forever |

In the same manner as described in Example 9, 20 amino acid substitution mutants at H103 residue were constructed by site-directed mutagenesis using QuickChange Site-Directed Mutagenesis Kit (STRATAGENE). Briefly, in order to introduce 20 amino acid substitutions at the H103 residue of both pUMESDsy and pUMESD, site-directed mutagenesis (single amino substitution) was performed by PCR using the above primers (combination of H103-20aa-F and H103-20aa-R and combination of ME-H103-20aa-F and ME-H103-20aa-R). One μl of DpnI was added to 50 μl of PCR reaction solution, which was then incubated at 37° C. for 1 hour. By this treatment, the template DNA was digested and only those plasmids into which mutations had been introduced were obtained. With the DpnI-treated PCR reaction solution, *E. coli* JM109 strain was transformed. Colonies were seeded at random in 0.8 ml 96-well sterilized plates (Abgene). After IPTG induction, enzyme solution was prepared by the method described in (2-1) in Example 8. Subsequently, in the same manner as in (2-2) in Example 8, degradation activity was measured with a microplate reader. When the activity was measured using 96-well plates, templates pUMESDsy and pUMESD and high activity mutants pUMESDsy-H103L and pUMESD-H103L were used as controls. For analysis, LS-PLATE manager 2001(Win) (Wako Purechemical) was used. Plasmids were extracted and purified from the resultant colonies. Then, their sequences were confirmed by DNA sequence analysis using BigDye Terminator v3.1 Cycle Sequencing Kit (ABI).

(2) Results

By the site-directed mutagenesis using the above-described random primers, amino acid substitutions were introduced at random into the H103 residue of both pUMESDsy and pUMESD. DNA sequence analysis revealed that total 40 types of mutants in which H103 residue was changed to 20 amino acids were obtained. The codon of the 103 residue in each amino acid substitution mutant is shown in Table 15.

TABLE 15

Codons Used in 20 Amino Acid Substitution Mutants at H103 Residue of pUMESDsy and pUMESD

| Amino acid (one letter abbreviation) | pUMESDsy-derived (*E. coli* codon) | pUMESD-derived (plant codon) |
|---|---|---|
| Ala (A) | gcc | gcc |
| Val (V) | gtc | gtc |
| Leu (L) | ctc | ctg |
| Ile (I) | atc | atc |
| Pro (P) | ccc | ccc |
| Phe (F) | ttc | ttc |
| Trp (W) | tgg | tgg |
| Met (M) | atg | atg |
| Gly (G) | ggg | ggg |
| Ser (S) | agc | tcg |
| Thr (T) | acc | acg |
| Cys (C) | tgt | tgc |
| Gln (Q) | cag | cag |
| Asn (N) | aac | aac |
| Tyr (Y) | tac | tac |
| Lys (K) | aag | aag |
| Arg (R) | cgc | cgc |
| His (H) | cat | cac |
| Asp (D) | gac | gac |
| Glu (E) | gag | gaa |

Figure 6A:
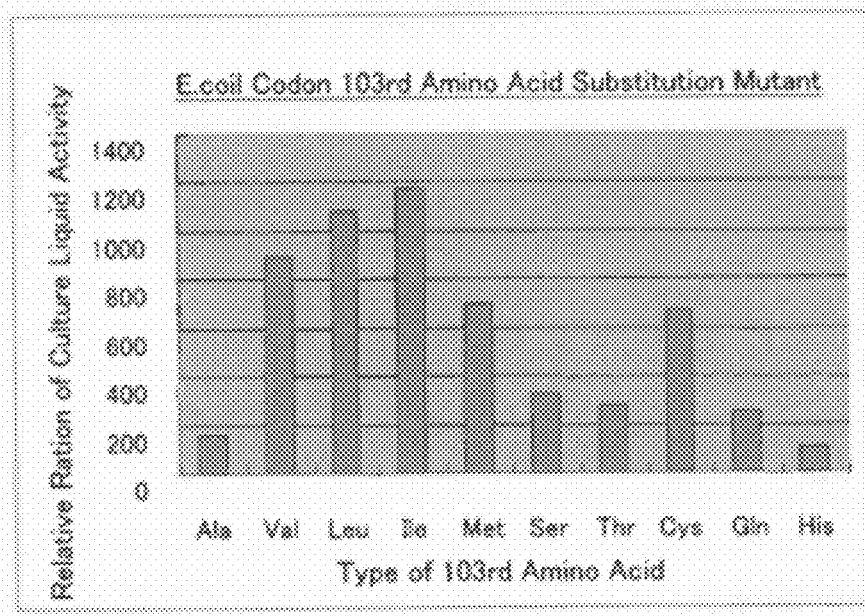
FIG. 6(A) is a graph showing the hydroxynitrile lyase activities of *E. coli* codon wild-type hydroxynitrile lyase (His) and 9 types of mutants obtained by substituting the histidine residue at position 103 of the wild-type amino acid sequence with other amino acids in Example 10.
Figure 6B:
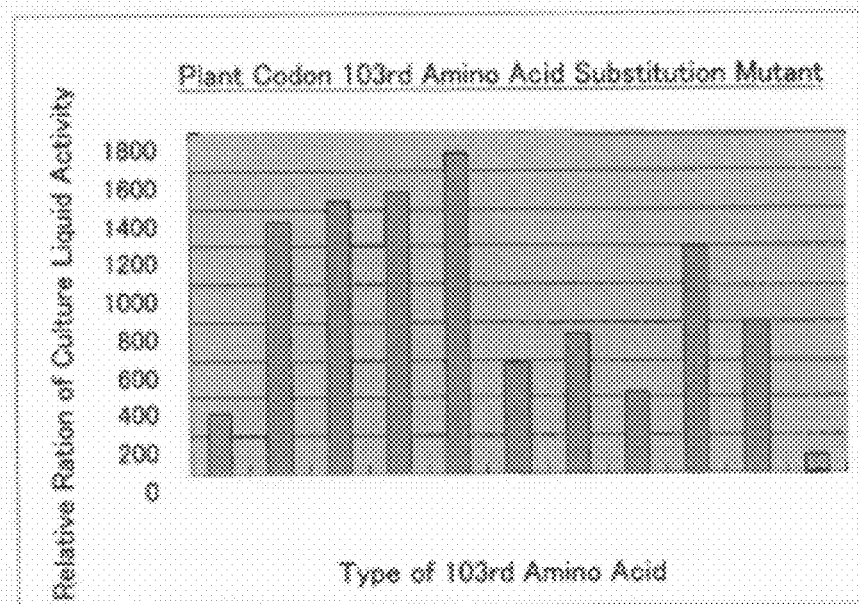
FIG. 6(B) is a graph showing the hydroxynitrile lyase activities of plant codon wild-type hydroxynitrile lyase (His) and 10 types of mutants obtained by substituting the histidine residue at position 103 of the wild-type amino acid sequence with other amino acids.

*E. coli* JM109/pUMESDsy-H103-20aa and JM109/pUMESD-H103-20aa (which are transformants expressing the resultant mutants) (here, "-20aa" represents one letter abbreviation of the amino acid which replaced H103; for example, when H103 was substituted with leucine, it is expressed as JM109/pUMESD-H103L) were cultured in LB+Amp (80 μg/ml) medium at 37° C. Simultaneously with the start of the cultivation, IPTG was added at a final concentration of 0.1 mM. Cells were cultured at 37° C. for 12 hours to allow expression of large quantities of hydroxynitrile lyases. After 12 hours, cells were harvested in 2.4 ml aliquots, washed with physiological saline, and suspended in 800 μl of 10 mM KPB (pH 7.0). Synthesis activity was measured by cell reaction. The results in *E. coli* codon mutants are shown in FIG. 6(A) and the results in plant codon mutants are shown in FIG. 6(B). Higher activity than the wild-type enzyme was confirmed in H103A, H103V, H103I, H103M, H103S, H103T, H103C, H103W and H103Q in addition to H103L. Since the results are almost equal in both codons, it was confirmed that the effect of H103 mutation does not depend on the type of codon.

EXAMPLE 11

Preparation of Transformants Expressing Combined Type Improved Hydroxynitrile Lyases in Which Amino Acids at Positions 2 and 103 are Substituted Based on pOXN103 prepared in (2) in Example 2 and pOXN103V2I prepared in (1) in Example 5, mutants in which the histidine (His; H) at position 103 is substituted with leucine (Leu; L) were prepared in the same manner as in Example 9 using QuickChange Site-Directed Mutagenesis Kit (STRATAGENE). As primers for introducing mutations, OXYN-30 (SEQ ID NO: 86) and OXYN-31 (SEQ ID NO: 87) used in Example 9 were used.

According to the protocol attached to the Kit, PCR reaction and DpnI treatment were performed. Subsequently, *E. coli* JM109 strain was transformed. Plasmid DNA was recovered from grown colonies. Expression vectors comprising a gene encoding hydroxynitrile lyase in which the amino acid at position 103 is substituted with leucine were designated pOXN103H103L (H103L mutation was introduced into pOXN103) and pOXN103V2I+H103L (H103L mutation was introduced into pOXN103V2I).

EXAMPLE 12

Evaluation of Recombinants Expressing Combined Type Improved Hydroxynitrile Lyases in Which Amino Acids at Positions 2 and 103 are Substituted
(1) Experimental Method
(1-1) Plasmids and Cell Strains Used

*E. coli* JM109 strain and C600 strain were transformed with pOXN103 (plant codon wild-type hydroxynitrile lyase expression vector) obtained in (2) in Example 2, pOXN103V2I (plant codon V2I hydroxynitrile lyase expression vector) obtained in (1) in Example 5, pOXN103H103L (plant codon H103L hydroxynitrile lyase expression vector) and pOXN103V2I+H103L (plant codon V2I+H103L hydroxynitrile lyase expression vector) both obtained in Example 11, in the same manner as described in (4) in Example 1. As a result, transformants JM109/pOXN103, JM109/pOXN103V2I, JM109/pOXN103H103L, JM109/pOXN103V2I+H103L, C600/pOXN103V2I and C600/pOXN103V2I+H103L were obtained.
(1-2) Cultivation Conditions
(1-2-1) Flask Culture Evaluation Colonies from transformants JM109/pOXN103, JM109/pOXN103V2I, JM109/pOXN103H103L and JM109/pOXN103V2I+H103L were flask-cultured in 100 ml of LBAmp medium (containing 0 or 1 mM IPTG) in 500 ml flasks at 30° C. or 37° C. under shaking (210 rpm).
(1-2-2) Jar Culture Evaluation Colonies from transformants C600/pOXN103V2I and C600/pOXN103V2I+H103L were precultured in the medium described below (100 ml in 500 ml Erlenmeyer flasks) at 30 ° C. for 12 hours.

Composition of Preculture Medium (pH 7.2):

Polypeptone N (20 g/L), yeast extract (5 g/L), $KH_2PO_4$ (1.5 g/L), ampicillin (0.1 g/L)

The rotational speed was 210 rpm.

The resultant preculture (20 ml) was seeded in the main culture medium described below (2 L in 3 L jar fermenters) and main-cultured at 37° C. or 25° C. for 20-52 hours.

| Composition of Main Culture Medium | |
|---|---|
| Polypeptone N | 20 g/L |
| Yeast extract | 5 g/L |
| $KH_2PO_4$ | 1.5 g/L |
| $MgSO_4 \cdot 7H_2O$ | 0.5 g/L |
| $MnSO_4 \cdot 5H_2O$ | 0.2 g/L |
| $ZnSO_4 \cdot 7H_2O$ | 0.02 g/L |
| $CaCl_2 \cdot 2H_2O$ | 0.02 g/L |
| Pluronic L-61 | 0.5 g/L |
| Fructose | 40 g/L |
| Ampicillin | 0.1 g/L |

The rotational speed was 750 rpm; air flow rate was 2 L/min; internal pressure was ordinary pressure; pH was controlled at 6.8-7.2 (with 3N NaOH and 5N $H_2SO_4$). During the culture, sampling was performed from time to time, followed by measurement of cell density (OD630) and hydroxynitrile lyase degradation activity.
(1-3) Sample Preparation Measurement of degradation activity was performed as described below. Cells were harvested from the sampled culture broth by centrifugation (3,700×g, 10 minutes, 4° C.), washed with 10 mM sodium phosphate buffer (pH 7.0) or phosphate buffer (pH 7) and suspended in 10 ml of the same buffer. The resultant cell suspension (1 ml) was disrupted with a sonicator VP-15S (Taitec, Japan) for 3 minutes under the following conditions: output control 4, DUTY CYCLE 40%, PULS, TIMER=B mode 10s, while ice-cooling. The disrupted cell suspension was collected as the total fraction of cell extract. The liquid contacting disrupted cell was centrifuged (10,000×g, 5 minutes, 4° C.), and the resultant supernatant was collected as the soluble fraction of cell extract. The precipitate was suspended in phosphate buffer (pH 7) in an amount equal to that of the supernatant, to thereby obtain the insoluble fraction of cell extract.
(1-4) Activity Measurement Using the soluble fraction of cell extract obtained above, hydroxynitrile lyase activity was measured. Briefly, activity was calculated by optically detecting (at 280 nm in wavelength) and tracing the activity to degrade a substrate racemic mandelonitrile (=generation of benzaldehyde).

Enzyme solution (50 μl) was mixed with 900 μl of 50 mM sodium citrate buffer (pH 5.0). A substrate solution (100 μl) (37.5 mM racemic mandelonitrile/10 mM sodium citrate buffer (pH 3.5) freshly prepared each time) was added to the above mixture to start the activity measurement. Increase in absorbance at 280 nm was traced for 5 minutes (as a control, enzyme-free substrate solution was used). One unit (1 U) corresponds to the amount of enzyme which catalyzes conversion of 1 μmol benzaldehyde from racemic mandelonitrile per minute under above-described conditions.
(1-5) SDS-PAGE SDS-PAGE was performed with 10% polyacrylamide gel (AA:Bis=38:2) and Tris-Glycine electrophoresis buffer.

Figure 7:
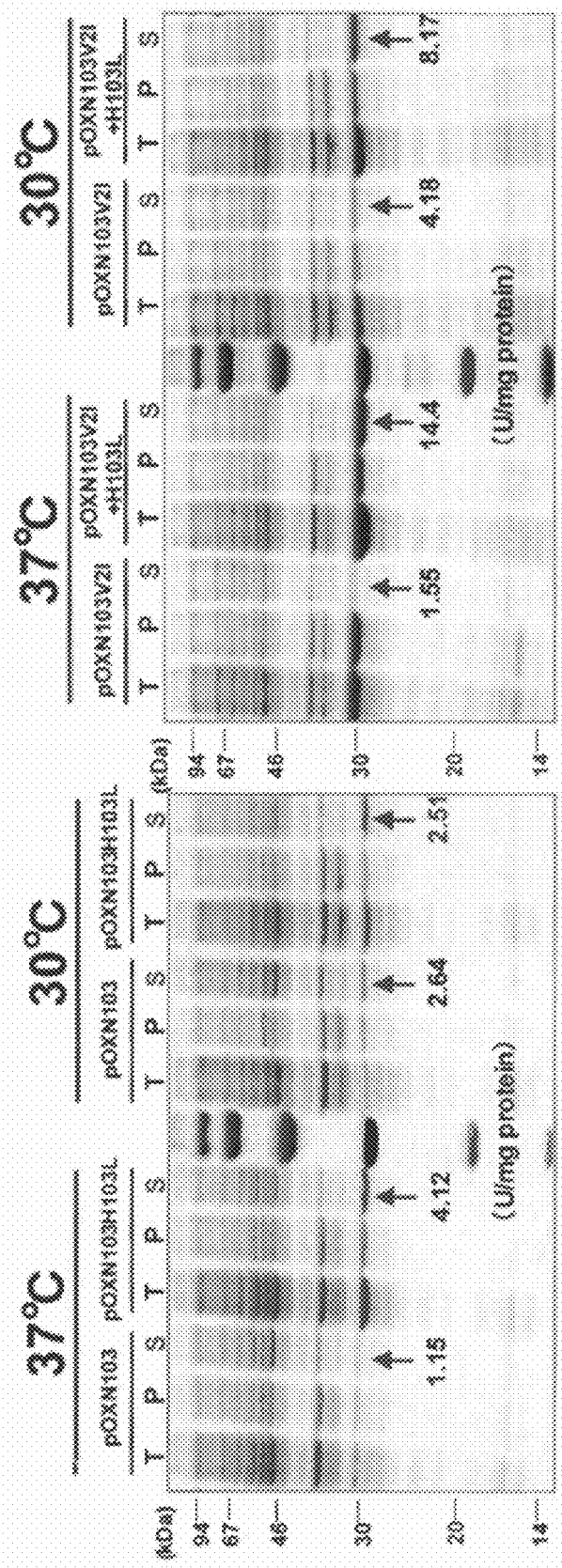
FIG. 7 is a diagram showing the results of SDS-PAGE analysis of individual fractions (T: total fraction; P: insoluble fraction; S: soluble fraction) of cell extracts obtained from flask cultivation at 30° C. and 37° C. of a plant codon wild-type hydroxynitrile lyase-expressing transformant (JM109/pOXN103); V2I mutation-introduced, plant codon improved hydroxynitrile lyase-expressing transformant (JM109/ pOXN103V2I); H103L mutation-introduced, plant codon improved hydroxynitrile lyase-expressing transformant (JM109/pOXN103H103L); and V2I and H103L mutations-introduced, plant codon combined type improved hydroxynitrile lyase-expressing transformant (JM109/pOXN103V2I+H103L) in Example 12.

(2) Evaluation of Flask Culture of Recombinants into Which Amino Acid Substitutions at Positions 2 and 103 are Introduced JM109/pOXN103, JM109/pOXN103 V2I, JM109/pOXN103H103L and JM109/pOXN103V2I+H103L obtained in (1-1) above were flask-cultured at 30° C. and 37° C. The culture was performed in 1 mM (final concentration) IPTG-added LB Amp medium (100 ml) (LB medium containing 100 mg/L ampicillin) with a rotational speed of 210 rpm. Individual fractions of cell extract were adjusted to give a concentration of OD12.5 and analyzed by SDS-PAGE and the degradation activity of soluble fraction was measured. The results are shown in FIG. 7. When H103L mutation alone was introduced into wild-type pOXN103 (pOXN103 H103L), specific activity per total protein was not greatly changed at 30° C. but increased about 4 times at 37° C. (FIG. 7; 1.15→4.12 U/mg protein). It was confirmed that increase in the ratio of soluble enzyme and enhancement of expression level per se also contributed to this increase in activity.

Further, when the amino acid mutation H103L at position 103 and the amino acid mutation V2I (pOXN103V2I) at position 2 are combined (pOXN103V2I+H103L), specific activity increased about twice at 30° C. (FIG. 7; 4.18→8.17 U/mg protein) and increased about 10 times at 37° C. (FIG. 7; 1.55→14.4 U/mg protein).

(3) Evaluation of Jar Culture of Recombinants into Which Amino Acid Substitutions at Positions 2 and 103 are Introduced E. coli C600 strain transformants prepared with pOXN103V2I and pOXN103V2I+H103L were cultured in 3 L jar fermenters.

The cultivation results are shown in FIG. 8. When C600/pOXN103V2I was cultured at 37° C., almost no activity (specific activity, liquid activity) was expressed, but C600/pOXN103V2I+H103L showed about 10 times activity (specific activity, liquid activity) compared to the former. Here, specific activity (U/mg DC) was calculated by measuring the degradation activity per ml of cell suspension, and dividing this activity value by dry cell mg weight concentration (mg DC/ml) calculated from the cell density OD630 of cell suspension (coefficient was 0.4). Further, liquid activity per culture broth (U/ml) was determined by multiplying specific activity (U/mg DC) by cell density of culture broth (mg DC/ml; calculated from cell density OD630 using coefficient=0.4). C600/pOXN103V2I+H103L achieved the activity (specific activity, liquid activity) which C600/pOXN103V2I achieved only after being cultured 50 hours or more at 25° C., in 20 hours (37° C.) which is less than half of the cultivation time of the former.

Further, it was recognized that the ratio of soluble fraction in C600/pOXN103V2I+H103L was increased more than the results seen in flask levels (FIG. 8; SDS-PAGE).

From the present Example, activity increase in 37° C. culture was confirmed as a result of introduction of the amino acid mutation at position 103 (H103L) into plant codon hydroxynitrile lyase gene, in the same manner as confirmed in E. coli codon gene. When plant codon V2I+H103L transformant was cultured at 37° C. in 3 L jar fermenters, more than 10 times activity was obtained compared to 37° C. culture of control (plant codon V2I). It was confirmed that a combination of amino acid mutations at position 2 and position 103 causes more synergistic effect on activity improvement.

EXAMPLE 13

Influence of the Codon in H103 Residue

Among codons which encode the same amino acid, there are the most frequently used codons in high expression genes and the most frequently used codons in all genes. The term "high expression gene" refers to, for example, a gene with high expression level in a great number of E. coli species. Plasmid pUMESDsy prepared in Example 4 was synthesized using latter codons. Then, respective clones in which the codon corresponding to H103 residue is cat or cac were prepared, and hydroxynitrile lyase activities and expression levels thereof were examined.

(1) Preparation of Substitution Mutants

Random primers in the codon encoding the His at position 103 were designed in pUMESDsy and mutants were prepared. PCR reaction conditions are shown in Table 16 below.

TABLE 16

| Composition of PCR Reaction Solution | |
|---|---|
| 10 × reaction Buffer | 5 (µl) |
| Template DNA (pUMESDsy) | 1 |
| 5'-primer (10 pmol/µl) | 1.25 |
| 3'-primer (10 pmol/µl) | 1.25 |
| dNTP mix | 1 |
| H$_2$O | 39.5 |
| Pfu Turbo DNA polymerase | 1 |
| Total | 50 (µl) |

The sequence of the above primer (5'-primer) is as described below.

(SEQ ID NO: 88)
H103-20aa-F:   ggcgggcgtttttnnsaacagcctgctgcc

The sequence of the above primer (3'-primer) is as described below.

(SEQ ID NO: 90)
H103-20aa-R:   ggcagcaggctgttsnnaaaaacgcccgcc

In both primer sequences, n is a, t, g or c and s is g or c. PCR reaction conditions are as shown in Table 17 below.

TABLE 17

| Error prone PCR Reaction Conditions | |
|---|---|
| 95° C. | 30 sec |
| 95° C. | 30 sec |
| 55° C. | 1 min  } × 16 cycles |
| 68° C. | 4 min |
| 4° C. | forever |

Site-directed mutations were introduced using Quick-Change Site-Directed Mutagenesis Kit (STRATAGENE) under the above-described conditions. One µl of DpnI was added to the PCR reaction solution, which was treated at 37° C. for 1 hour. After DpnI treatment, E. coli JM109 strain was transformed with the treated PCR reaction solution. Plasmids were extracted from colonies, purified and then subjected to DNA sequence analysis using BigDye Terminator v3.1 Cycle Sequencing Kit (ABI). Thus, two mutants in which the H103 codon of pUMESDsy is cat and cac, respectively, were obtained. Three ml of LB+Amp (80 μg/ml) was placed in sterilized test tubes, in which colonies of JM109/pUMESDsy (H103cac) and JM109/pUMESDsy (H103cat) were suspended separately and cultured at 37° C. overnight under shaking (preculture). Subsequently, LB+Amp (80 μg/ml)+ IPTG (0.1 mM) was placed in sterilized test tubes, in which individual precultures were seeded at 1% and cultured at 37° C. overnight under shaking (main culture). After 12 hours, 1.5 ml of the culture was centrifuged (8,000 rpm, 10 min, 4° C., himac CF15D; Hitachi) to harvest cells. The resultant cells were washed with 0.85% NaCl, and suspended in 500 μl of 10 mM KPB (pH 7.0) to perform cell reaction. Then, the activity was measured by HPLC analysis using CHIRALCEL OJ-H column (Daicel Chemical). Further, a part of the resultant cells was sonicated and centrifuged (8,000 rpm, 10 minutes, 4° C., himac CF15D; Hitachi) to obtain the supernatant as the soluble fraction. Further, to the precipitate, 8M Urea (in 10 mM KPB (pH 7.0)) was added in 1/10 amount relative to the amount of the enzyme solution of disrupted cells and suspended. The resultant suspension was centrifuged (7,000 rpm, 10 minutes, 4° C., himac CF15D; Hitachi) to obtain the supernatant as the insoluble fraction. Activity measurement was performed on the soluble fraction. Quantitative determination of protein and SDS-PAGE were performed on both soluble and insoluble fractions.

(2) Influence by Different Codons

The nucleotides of H103 residue of pUMESDsy were converted to two codons (cat and cac) corresponding to His. The resultant JM109/pUMESDsy-H103(cat) and JM109/pUMESDsy-H103(cac) were cultured in LB+Amp (80 μg/ml) at 37° C. Simultaneously with the start of the culture, IPTG was added thereto at a final concentration of 0.1 mM. Cells were cultured at 37° C. for 12 hours to allow expression of large quantities of hydroxynitrile lyases. After 12 hours, cells were harvested in 1.5 ml aliquots, washed with physiological saline, suspended in 500 μl of 10 mM KPB (pH 7.0) and disrupted by sonication. The liquid containing disrupted cells was centrifuged at a low speed. The resultant supernatant was collected as the soluble fraction (soluble) and used in activity measurement and quantitative determination of protein. The precipitate was dissolved in 8 M urea and centrifuged at a low speed. The resultant supernatant was collected as the insoluble fraction (insoluble) and used in quantitative determination of protein. SDS-PAGE was performed using 10 μg of each protein based on the resultant value.

The results are shown in Table 18 and FIG. 9.

TABLE 18

Influence of His Codons on Hydroxynitrile Lyase Activity

|  | His (cat) | His (cac) |
|---|---|---|
| Relative activity (U/ml) | 2.01 | 2.47 |
| Specific activity (U/mg) | 1.51 | 1.64 |

In cell clones where a high frequency codon in *E. coli* high expression genes (cac) and a high frequency codon in all of the genes in *E. coli* (cat) were used for H103, respectively, no remarkable difference was recognized in activity (Table 18) and expression level (FIG. 9). Therefore, it was believed that there is little influence on activity and expression level between the above two codons.

EXAMPLE 14

Purification of H103M Improved Hydroxynitrile Lyase and Confirmation of Properties
(1) Purification of Wild-Type Hydroxynitrile Lyase and H103M Improved Hydroxynitrile Lyase JM109/pUMESD obtained in (1) in Example 2 and JM109/pUMESD-H103M obtained in (2) in Example 10 were cultured, and wild-type hydroxynitrile lyase and H103M improved hydroxynitrile lyase were purified from the individual cells, respectively.

(1-1) Cultivation and Harvesting

Three ml of LB+Amp (80 μg/ml) was placed in sterilized test tubes. Colonies from JM109/pUMESD and JM109/pUMESD-H103M were suspended therein separately and cultured at 37° C. overnight (preculture).

Each of the resultant precultures was seeded in the following medium at 1%.

| Medium Composition | |
|---|---|
| Peptone | 10 g/L |
| Yeast extract | 5 g/L |
| NaCl | 10 g/L |
| Ampicillin | 80 mg/L |
| IPTG | 0.1 mM (final concentration) |

The liquid volume of the medium was 10 L in total for JM109/pUMESD and 2 L in total for JM109/pUMESD-H103M. Cells were cultured at 37° C. for 12 hours (main culture). Then, the culture broth was centrifuged (6,000 rpm, 10 minutes, 4° C.) to harvest cells. The resultant cells were washed with 0.7% NaCl and recentrifuged for harvesting. This washing operation was repeated twice, and then the cells were suspended in sonication buffer (50 mM sodium phosphate/citrate buffer (pH 5.4), 1 mM EDTA) in an amount 5 times as much as the cell wet weight to thereby obtain a cell suspension.

(1-2) Cell Disrupting

Using a sonicator (Insonator model 201M (9 kHz); Kubota Shoji), the cell suspension was disrupted for 20 minutes. Thereafter, the disrupted liquid was centrifuged (15,000 rpm, 10 minutes, 4° C.) to separate into supernatant and precipitate. The resultant precipitate was suspended in the sonication buffer and sonicated again. Centrifugation was performed again (15,000 rpm, 10 minutes, 4° C.) to obtain the supernatant (cell extract).

(1-3) Thermal Treatment

The cell extract obtained in (1-2) above was transferred into an Erlenmeyer flask and subjected to thermal treatment at 60° C. for 10 minutes in a water bath. After this treatment, the cell extract was cooled rapidly in ice water and centrifuged (12,000 rpm, 10 minutes, 4° C.) to remove denatured protein, to thereby obtain a crude enzyme solution.

(1-4) Ammonium Sulfate Fractionation

The crude enzyme solution obtained in (1-3) above was 45% ammonium sulfate-saturated and agitated for 30 minutes. The precipitate obtained by centrifugation (15,000 rpm, 20 minutes, 4° C.) was collected as 0-45% fraction and dissolved in 10 mM KPB (pH 7.0). Subsequently, the supernatant was 65% ammonium sulfate-saturated and agitated for 30 minutes. The precipitate obtained by centrifugation (15,000 rpm, 20 minutes, 4° C.) was collected as 45-65% fraction and dissolved in 10 mM KPB (pH 7.0). Further, the supernatant was 90% ammonium sulfate-saturated and agitated for 30 minutes. The precipitate obtained by centrifugation (15, 000 rpm, 20 minutes, 4° C.) was collected as 65-90% fraction and dissolved in 10 mM KPB (pH 7.0). The protein solutions of individual fractions were dialyzed with 10 mM KPB (pH 7.0), followed by activity measurement and quantitative determination of protein for each fraction. Activity measurement was performed in the same manner as in (2-3) in Example 8. Quantitative determination of protein was performed with Bio-Rad Protein Assay (Bio-Rad) according to the attached protocol.

(1-5) DEAE-Toyopearl Column Chromatography

DEAE-Toyopearl resin was packed in a column and, after washing, equilibrated with 10 mM KPB (pH 7.0). Then, the enzyme solution after dialysis obtained in (1-4) above was applied to the column. After washing with 10 mM KPB (pH 7.0), protein was eluted with linear concentration gradient of 0-0.5 M NaCl in 10 mM KPB (pH 7.0). Active fractions after elution were collected, dialyzed with 10 mM KPB (pH 7.0) and used in the subsequent step.

(1-6) Butyl-Toyopearl Column Chromatography

The active fractions obtained in (1-5) above were 30% ammonium sulfate-saturated and applied to Butyl-Toyopearl columns pre-equilibrated with 30% ammonium sulfate-saturated 10 mM KPB (pH 7.0). After washing with 30% ammonium sulfate-saturated 10 mM KPB (pH 7.0), protein was eluted with linear concentration gradient of 30-0% ammonium sulfate-saturated 10 mM KPB (pH 7.0). Active fractions after elution were collected, dialyzed with 10 mM KPB (pH 7.0) and used in the subsequent step.

(1-7) Superdex 200 HR 10/30 Column Chromatography

Superdex 200 HR 10/30 column was washed with degassed milliQ water and equilibrated with 0.2 M NaCl in 10 mM KPB (pH 7.0). The enzyme solution after dialysis obtained in (1-6) above was applied to this column. Protein was eluted with 0.2 M NaCl in 10 mM KPB (pH 7.0). Eluted active fractions were collected, dialyzed with 10 mM KPB (pH 7.0) and used in the subsequent step.

(1-8) MonoQ HR 10/30

MonoQ HR 10/30 was washed with degassed milliQ water, equilibrated with 1 M NaCl in 10 mM KPB (pH 7.0), and washed with 10 mM KPB (pH 7.0). Then, the enzyme solution after dialysis obtained in (1-7) above was applied thereto. Protein was eluted with linear concentration gradient of 0-1 M NaCl in 10 mM KPB (pH 7.0). Eluted active fractions were collected and dialyzed with 10 mM KPB (pH 7.0).

(1-9) Results of Purification

The results of purification of H103M improved hydroxynitrile lyase are shown in Table 19. It was possible to purify H103M improved hydroxynitrile lyase to 9-fold or more purity through the above-described steps.

TABLE 19

Purification Steps for H103M Improved Hydroxynitrile Lyase

| | total activity (U) | total protein (mg) | specific activity (U/mg) | Yield (%) | fold purification |
|---|---|---|---|---|---|
| Cell extract | 43577.8 | 1088.1 | 40.1 | 100 | 1 |
| Heat treatment | 28188.8 | 396.2 | 71.2 | 64.7 | 1.78 |
| (NH$_4$)$_2$SO$_4$: 45-65% | 18118.1 | 160.1 | 113.1 | 41.6 | 2.82 |
| DEAE-Toyopearl | 18533.1 | 103.3 | 179.4 | 42.5 | 4.47 |
| Butyl-Toyopearl | 4814.3 | 16.1 | 298.6 | 11.0 | 7.46 |
| Superdex | 6579.2 | 17.3 | 380.3 | 15.1 | 9.49 |

The purified wild-type hydroxynitrile lyase and H103M improved hydroxynitrile lyase were analyzed by SDS-PAGE. Specific activities per protein were determined for both enzymes as described later, and 0.3 U per lane was applied. The results of SDS-PAGE are shown in FIG. 10. It was confirmed that both enzymes are purified to a single band. Since the band of H103M improved hydroxynitrile lyase seemed thinner than the band of wild-type hydroxynitrile lyase, it was suggested that the specific activity per enzyme protein of H103M improved hydroxynitrile lyase is improved compared to that of wild-type hydroxynitrile lyase. Actually, the results of determination of specific activities per enzyme protein of both enzymes confirmed that specific activity of H103M improved hydroxynitrile lyase is enhanced to about 1.5-fold relative to that of wild-type hydroxynitrile lyase, as shown in Table 20.

TABLE 20

Specific Activities per Enzyme Protein of Wild-Type and H103M Improved Hydroxynitrile Lyases

| Wild-type hydroxynitrile lyase | H103M improved hydroxynitrile lyase |
|---|---|
| 98.8 U/mg | 143.4 U/mg |

(2) Effect on Activity of Chelating Agents and Metals Added to Reaction System

Using purified enzymes of wild-type hydroxynitrile lyase and H103M improved hydroxynitrile lyase obtained in (1) in Example 14, effects on synthetic activity of chelating agents and metals added to mandelonitrile synthesis reaction system were examined. Specifically, a chelating agent (EDTA) and various metals (CoCl$_2$, NiSO$_4$, MgCl$_2$, CaCl$_2$, NaCl, KCl and LiCl) were added at a final concentration of 1 mM or 10 mM. Briefly, mandelonitrile synthesis reaction was performed with the reaction composition as shown in Table 21, and the activity was measured in the same manner as described in (2-3) in Example 8.

TABLE 21

| Reaction Composition | | |
|---|---|---|
| | Final Concentration | |
| | 1 mM | 10 mM |
| 500 mM Na-citrate buffer (pH 4.0) | 600 | 600 |
| Enzyme solution | 100 | 100 |
| 1.25M benzaldehyde (dissolved in DMSO) | 40 | 40 |
| 1M KCN | 100 | 100 |
| 100 mM additive solution (EDTA, CoCl$_2$, NiSO$_4$, MgCl$_2$, CaCl$_2$, NaCl, KCl, LiCl) | 10 | 100 |
| DIW | 150 | 60 |
| Total | 1000 µl | 1000 µl |

The results are shown in Table 22. Table 22 shows relative activities taking the activity in a reaction system without any additive as 100%. For each of the additives, the upper row shows the relative activity when the relevant additive was added at 1 mM, and the lower row shows the relative activity when the relevant additive was added at 10 mM. When EDTA and NiSO$_4$ were added at 1 mM, no considerable decrease in activity was observed in both the wild-type hydroxynitrile lyase and H103M improved hydroxynitrile lyase. Difference between these enzymes was also small. On the other hand, when other metals (CoCl$_2$, MgCl$_2$, CaCl$_2$, NaCl, KCl, LiCl) were added, in particular added at 10 mM in the reaction solution, relatively large decrease in activity was observed. Although the activity decrease ratio varied depending on the metal added, it was confirmed that the activity decrease ratio in H103M improved hydroxynitrile lyase was smaller than that in wild-type hydroxynitrile lyase. Thus, it was confirmed that because of H103M mutation, H103M improved hydroxynitrile lyase has become less susceptible to the effect of metals.

TABLE 22

Effect of Metals on Mandelonitrile Synthesis Reaction System

|  | Wild-type hydroxynitrile lyase | H103M improved hydroxynitrile lyase |
|---|---|---|
| EDTA | 93.9 | 92.2 |
|  | 83.4 | 100.4 |
| CoCl$_2$ | 65.4 | 88.0 |
|  | 26.1 | 35.0 |
| NiSO$_4$ | 99.6 | 91.8 |
|  | 68.0 | 85.4 |
| MgCl$_2$ | 72.2 | 79.2 |
|  | 36.5 | 39.8 |
| MnCl$_2$ | 67.6 | 78.6 |
|  | 35.5 | 38.4 |
| CaCl$_2$ | 73.7 | 80.4 |
|  | 37.4 | 43.0 |
| NaCl | 80.7 | 88.7 |
|  | 46.2 | 53.1 |
| KCl | 76.0 | 88.2 |
|  | 47.6 | 50.9 |
| LiCl | 86.9 | 90.5 |
|  | 48.5 | 57.2 |

EXAMPLE 15

Preparation and Evaluation of Improved Hydroxynitrile Lyase with Lysine Residue Single Substitution Mutation (1) Introduction of Site-Directed Single Substitution Mutation into Lysine Residue Using the expression vector pUMESDsy prepared in Example 4 comprising the *E. coli* colon wild-type hydroxynitrile lyase gene as a template, *E. coli* colon improved hydroxynitrile lyase genes encoding an improved hydroxynitrile lyase in which the lysine residue at position 176, 199 or 224 is substituted with another amino acid were prepared by site-directed mutagenesis. The site-directed mutagenesis was performed using QuickChange Site-Directed Mutagenesis Kit (Stratagene) and primers which introduce random mutation into the amino acid at position 176, 199 or 224.

PCR reaction conditions are shown in Table 23.

TABLE 23

Composition of PCR Reaction Solution

| 10 × reaction Buffer | 5 (μl) |
|---|---|
| Template DNA (pUMESDsy) | 1 |
| 5'-primer | 1.25 |
| 3'-primer | 1.25 |
| dNTP mix | 1 |
| H$_2$O | 39.5 |
| Pfu Turbo DNA polymerase | 1 |
| Total | 50 (μl) |

Sequences for the 5'-primer are as described below.
For position 176 mutant:

K176-F:
(SEQ ID NO: 92)
ctggcgaaaatggtgatgcgcnnsggcagcctgtttcagaacgtgc

For position 199 mutant:

K199-F:
(SEQ ID NO: 93)
cgaaaaaggctatggcagcattnnsaaagtgtatatttggaccgatcagg

For position 224 mutant:

K224-F:
(SEQ ID NO: 94)
gcgctggcagattgcgaactatnnnccggataaagtgtatcagg

Sequences for the 3'-primer are as described below.
For position 176 mutant:

K176-R:
(SEQ ID NO: 95)
gcacgttctgaaacaggctgccsnngcgcatcaccattttcgccag

For position 199 mutant:

K199-R:
(SEQ ID NO: 96)
cctgatcggtccaaatatacactttsnnaatgctgccatagccttttt

For position 224 mutant:

K224-R:
(SEQ ID NO: 97)
cctgatacactttatccggnnnatagttcgcaatctgccagcgc

In the above primer sequences, n is a, t, g or c and s is g or c.

PCR reaction conditions are as shown in Table 24 below.

TABLE 24

PCR Reaction Conditions

| 95° C. | 30 sec |
|---|---|
| ↓ | |
| 95° C. | 30 sec ⎫ |
| 55° C. | 1 min ⎬ × 16 cycles |
| 68° C. | 4 min ⎭ |
| ↓ | |
| 4° C. | forever |

One μl of DpnI was added to 50 μl of PCR reaction solution, which was then incubated at 37° C. for 1 hour. By this treatment, the template DNA was digested and only those plasmids into which mutations had been introduced were obtained. Using the DpnI-digested PCR reaction solution, *E. coil* JM109 strain was transformed. Master plates of mutant colonies were prepared and used in the activity increase screening experiment described below.

(2) Screening of Mutants

From the mutants obtained in (1) above, those which show increased activity were screened.

(2-1) Primary Screening

Samples were prepared in 96-well plates. LB medium (containing 80 μg/ml Amp and 0.1 mM IPTG) was dispensed into 0.8 ml 96-well sterilized plates (Abgene) at 150 μl/well. Then, mutant colonies were seeded therein from the master plate. The 96-well plate was subjected to shake culture at 37° C. at 1,200 rpm for 12 hours with BioShaker (M-BR-024, TAITEC). After cultivation, the culture broth was centrifuged (5,000 rpm, 10 min, 4° C., himac CR20, rotor R6S; Hitachi) to harvest the cells. After removal of the supernatant, the plate was placed upside down on newspaper to remove the medium as much as possible. The resultant cells were suspended in 100 μl of 0.85% NaCl using BioShaker. Then, this suspension was transferred into a 96-well U-bottom plate (Corning). Subsequently, the cells were harvested by centrifugation (4,500 rpm, 10 min, 4° C., himac CR20, rotor R6S; Hitachi) and the supernatant was removed. The plate was placed upside down on newspaper to remove moisture content. To the resultant cells, a lysozyme solution [10 mg/ml lysozyme (derived from egg white; Seikagaku Corporation), 100 mM KPB (pH 7.0), 10 mM EDTA] was added and suspended with a TUPLE MIXER (speed 7; IWAKI). The suspension was incubated at 37° C. for 1 hour to perform lysozyme treatment to thereby make E. coli into protoplast. The resultant E. coli was subjected to freeze/thaw treatment at −40° C. and 37° C. To the resultant cells, 100 μl of a hypotonic solution (10 mM KPB (pH 7.0), 5 mM MgCl$_2$) was added for lysis. The resultant solution was centrifuged (4,500 rpm, 10 minutes, 4° C., himac CR20, rotor R6S; Hitachi) to thereby precipitate E. coli genome and cell walls, etc. The resultant supernatant was collected as a crude enzyme solution and used in the subsequent activity measurement.

The activity to degrade mandelonitrile (a substrate for hydroxynitrile lyase) was determined by measuring the amount of benzaldehyde generated. The reaction composition is shown in Table 25 below.

TABLE 25

| Reaction Composition | | |
|---|---|---|
| | | Final Concentration |
| 100 mM Na-citrate buffer (pH 5.4) | 100 (μl) | 50 mM |
| 10 mM racemic mandelonitrile | 80 | 4 mM |
| Enzyme solution (crude enzyme solution) | 10 | |
| DIW | 10 | |
| Total | 100 (μl) | |

For activity measurement, sodium citrate buffer was added to 96-well UV plates (Greiner Bio-One) and its temperature was adjusted to 25° C. Then, the crude enzyme solution was added thereto and suspended by pipetting. Subsequently, racemic mandelonitrile was added thereto, followed by pipetting and shaking. Then, increase in absorbance at 280 nm in wavelength was measured at 25° C. for 10 minutes using a microplate reader (GENios; Tecan Japan). For analysis, LS-PLATE manager 2001 (Win) (Wako Purechemical) was used. Screening was performed using pUMESDsy as a positive control and pUC19 as a negative control. For each of the position 176 mutant, position 199 mutant and position 224 mutant, samples showing higher activity than positive control were selected from 188 samples. As a result, 12 samples of position K176 mutant, 2 samples of position K199 mutant and 11 samples of position K224 mutant were obtained.

(2-2) Secondary Screening

Three ml each of LB+Amp (80 μg/ml) was placed in sterilized test tubes. The 12 samples of position K176 mutant, 2 samples of position K199 mutant and 11 samples of position K224 mutant all of which showed higher activity than positive control in the primary screening; the positive control pUMESDsy and the negative control pUC19 were seeded therein and cultured at 37° C. overnight under shaking (pre-culture). After 12 hours, 1.5 ml of the culture was centrifuged (8,000 rpm, 10 min, 4° C., himac CF15D; Hitachi) to harvest cells. The resultant cells were washed with 0.85% NaCl, suspended in 500 μl of 10 mM KPB (pH 7.0), and disrupted. The resultant disrupted cells were centrifuged (8,000 rpm, 10 min, 4° C., himac CF15D; Hitachi) to obtain the supernatant as a soluble fraction. Using the thus obtained soluble fraction, activity measurement was performed. Briefly, production of (S)-mandelonitrile from benzaldehyde was analyzed by HPLC using a chiral column to thereby determine the synthesis activity. The standard assay solution contains 300 mM citrate buffer (pH 4.0), 50 mM benzaldehyde and 100 mM cyanide solution in its final volume of 0.9 ml. The reaction was immediately started by adding 100 μl of enzyme solution and the reaction solution was incubated at 25° C. for 120 minutes. The reaction was terminated by adding 900 μl of organic solvent (hexane:isopropanol=9:1). Then, the supernatant obtained by centrifugation (15,000×g, 10 minutes) was assayed by HPLC. The amounts of individual components were measured by feeding to CHIRALCEL OJ-H column (Daicel Chemical) at a flow rate of 1.0 ml/minute using hexane:isopropanol=90:10 as a mobile phase and measuring absorbance at 254 nm. From the resultant standard curves, the amounts of individual components were calculated. The amount of enzyme which generates 1 μmol S-mandelonitrile from benzaldehyde per minute under standard assay conditions was defined as 1 unit of enzyme activity. For each of the position 176 mutant, position 199 mutant and position 224 mutant, samples showing higher activity than positive control were confirmed. Using soluble fractions from these high activity samples, quantitative determination of protein and SDS-PAGE (10 μg of each sample protein) were performed.

(2-3) Results of Screening

As a result of activity measurement, samples with remarkably higher activity than the positive control were confirmed in each of the position 176 mutant, position 199 mutant and position 224 mutant. Recombinant vectors were prepared from these samples, and nucleotide sequences thereof were examined in the same manner as described in (4) in Example 1. The results revealed that, in position 176 mutant, the codon aaa encoding lysine in wild-type hydroxynitrile lyase has been changed to ccc that encodes proline (K176P). Likewise, in position 199 mutant, the codon aaa encoding lysine in wild-type hydroxynitrile lyase has been changed to ccc that encodes proline (K199P); and in position 224 mutant, the codon aaa encoding lysine in wild-type hydroxynitrile lyase has been changed to cct that encodes proline (K224P).

The activities per soluble protein of K176P, K199P and K224P single substitution mutants are shown in Table 26. K176P showed 2.9-fold activity compared to positive control pUMESDsy; K199P showed 2.3-fold activity compared to positive control pUMESDsy; and K224P showed 3.3-fold activity compared to positive control pUMESDsy. Further, the results of SDS-PAGE analysis (FIG. 11) confirmed that the amount of hydroxynitrile lyase in soluble fraction is increased in any of the single substitution mutants K176P, K199P and K224P. These results confirmed that it is possible to improve the expression level and activity of hydroxynitrile lyase by substituting a lysine residue with another amino acid, especially proline, in the amino acid sequence of a wild-type hydroxynitrile lyase.

TABLE 26

Activities of Lysine Substitution Mutants

| Sample | Hydroxynitrile lyase activity (U/mg-protein) |
| --- | --- |
| pUMESDsy | 1.5 |
| K176P | 4.4 |
| K199P | 3.4 |
| K224P | 4.9 |
| K176P × K224P | 10.7 |
| K199P × K224P | 8.0 |
| K176P × K199P × K224P | 11.1 |

EXAMPLE 16

Preparation and Evaluation of Improved Hydroxynitrile Lyases with Lysine Residue Multiple Substitutions (1) Preparation of Lysine Residue Multiple Substitution Mutants E. coli codon improved hydroxynitrile lyase genes encoding multiple substitution mutants in which two or three lysine residues are substituted were prepared based on the lysine residue single substitution mutants obtained in Example 15. First, using expression vector pUMESDsy-K224P comprising K224P mutation as a template, a double mutant in which the lysine residues at positions 176 and 224 are substituted with proline residues (K176PxK224P) and a double mutant in which the lysine residues at positions 199 and 224 are substituted with proline residues (K199PxK224P) were prepared by site-directed mutagenesis. Further, using expression vector pUMESDsy-K176PxK224P comprising the resultant double mutation K176PxK224P as a template, a triple mutant in which all the lysine residues at positions 176, 199 and 224 are substituted with proline residues (K176PxK199xK224P) was prepared. As described in (1) in Example 15, site-directed mutagenesis was preformed using QuickChange Site-Directed Mutagenesis Kit (Stratagene).

PCR reaction conditions are shown in Table 27 below.

TABLE 27

Composition of PCR Reaction Solution

| | |
| --- | --- |
| 10 × reaction Buffer | 5 (µl) |
| Template DNA | 1 |
| 5'-primer | 1.25 |
| 3'-primer | 1.25 |
| dNTP mix | 1 |
| H₂O | 39.5 |
| Pfu Turbo DNA polymerase | 1 |
| Total | 50 (µl) |

The template DNA above is pUMESDsy-K224P when preparing K176PxK224P mutant and K199PxK224P mutant; and the template DNA above is pUMESDsy-K176PxK224P when preparing mutation K176PxK199PxK224P.

Sequences for 5'-primer are as described below.
For preparing K176PxK224P mutant:

K176P-F:
(SEQ ID NO: 98)
ctggcgaaaatggtgatgcgcccnggcagcctgtttcagaacgtgc

For preparing K199PxK224P mutant and K176PxK199PxK224P mutant:

K199P-F:
(SEQ ID NO: 99)
cgaaaaaggctatggcagcattccnaaagtgtatatttggaccgatcagg

Sequences for 3'-primer are as described below.
For preparing K176PxK224P mutant:

K176P-R:
(SEQ ID NO: 100)
gcacgttctgaaacaggctgccngggcgcatcaccattttcgccag

For preparing K199PxK224P mutant and K176PxK199PxK224P mutant:

K199P-R:
(SEQ ID NO: 101)
cctgatcggtccaaatatacactttnggaatgctgccatagcctttt

In the above primer sequences, n is a, t, g or c. The codon specifying proline is cct, ccc, cca or ccg. The mutation introduction primers described above are designed so that any of the proline codons always comes at the mutation site of interest (in 5'-primer, ccn; in 3'-primer, ngg).

PCR reaction conditions are the same as described in (1) in Example 15.

One µl of DpnI was added to 50 µl of PCR reaction solution, which was then incubated at 37° C. for 1 hour. By this treatment, the template DNA was digested and only those plasmids into which mutations had been introduced were obtained. With the DpnI-treated PCR reaction solution, E. coli JM109 strain was transformed in the same manner as describe in (4) in Example 1. Recombinant vectors were prepared from the resultant transformants, and analysis of the nucleotide sequences thereof were performed in the same manner as described in (3) in Example 1. As a result, it was confirmed that the double mutant in which the lysine residues at positions 176 and 224 are substituted with proline (K176PxK224P), the double mutant in which the lysine residues at positions 199 and 224 are substituted with proline (K199PxK224P), and the triple mutant in which all the lysine residues at positions 176, 199 and 224 are substituted with proline (K176PxK199xK224P) were prepared correctly.

(2) Activities and Expression Levels of Lysine Residue Multiple Substitution Mutants The resultant lysine residue multiple substitution mutants (K176PxK224P, K199PxK224P and K176PxK199PxK224P) were cultured in the same manner as described in (2-3) in Example 15. After preparation of soluble fractions, activity measurement, quantitative determination of protein and SDS-PAGE (10 µg of each sample protein) were performed. The results of activity measurement are shown in Table 26. K176PxK224P showed 7.1-fold activity compared to positive control pUMESDsy; K199PxK224P showed 5.3-fold activity compared to positive control pUMESDsy; and K176PxK199PxK224P showed 7.4-fold activity compared to positive control pUMESDsy. Further, as a result of SDS-PAGE analysis (FIG. 11), it was confirmed that the amount of hydroxynitrile lyase in soluble fraction is increased more in any of the multiple substitution mutants of K176PxK224P, K199PxK224P and K176PxK199PxK224P than in the above-described single substitution mutants. These results confirmed that substitution of a plurality of lysine residues with other amino acids, especially proline, in the amino acid sequence of a wild-type hydroxynitrile lyase is capable of improving hydroxynitrile lyase expression level per cell and activity remarkably.

EXAMPLE 17

Preparation and Evaluation of Combined Type Improved Hydroxynitrile Lyases in which Histidine Residue at Position 103 and Lysine Residue(s) are Substituted (1) Preparation of Combined Type Mutants in Which Histidine Residue at Position 103 and Lysine Residue(s) are Substituted Combined type mutants were prepared by introducing H103L mutation (histidine residue at position 103 is substituted with leucine) into the lysine residue single substitution or multiple substitution mutants obtained in Examples 15 and 16. As templates, pUMESDsy-K176P, -K199P, -K224P (these are lysine residue single substitution mutants) obtained in Example 15; and -K176PxK224P, -K199PxK224P (these are lysine residue double substitution mutants) and K176PxK199PxK224P (lysine residue triple substitution mutant) obtained in Example 16 were used. In the same manner as described in Example 9, mutants of interest were prepared using Quick Change Site-Directed Mutagenesis Kit (STRATAGENE). As mutation introduction primers, OXYN-30 (SEQ ID NO: 86) and OXYN-31 (SEQ ID NO: 87) used in Example 9 were used.

According to the protocol attached to the Kit, PCR reaction was performed and the reaction solution was treated with DpnI. *E. coli* JM109 strain was transformed, and plasmid DNA was recovered from grown colonies. As a result, hydroxynitrile lyase mutants in which one to three lysine residues are substituted and yet the amino acid at position 103 is substituted with leucine were obtained; K176P+H103L, K199P+H103L, K224P+H103L (these are lysine residue single substitution+H103L mutants), K176PxK224P+H103L, K199PxK224P+H103L (these are lysine residue double substitution+H103L mutants) and K176PxK199PxK224P+H103L.

(2) Evaluation of Combined Type Mutants in Which Histidine Residue at Position 103 and Lysine Residue(s) are Substituted Each transformant obtained in (1) above was cultured in 3 ml of LB medium at 37° C. for 12 hours. Simultaneously with the start of the culture, IPTG was added thereto at a final concentration of 0.1 mM. After 12 hours, cells were harvested, washed with physiological saline and suspended in ⅓ volume of 10 mM KPB (pH 7.0). Activity measurement was performed by cell reaction. From the resultant value, activity per culture broth was calculated. The results are shown in Table 28. A remarkable improvement in activity compared to the wild-type was confirmed in any of the combined type mutants.

TABLE 28

Activities of Combined Type Mutants in which Histidine Residue at Position 103 and Lysine Residue(s) Are Substituted

|  | U/ml culture |
|---|---|
| pUMESDsy | 9.0 |
| pUMESDsy-K176P × H103L | 99.0 |
| pUMESDsy-K199P × H103L | 120.9 |
| pUMESDsy-K224P × H103L | 98.1 |
| pUMESDsy-K176P × K224P × H103L | 109.5 |
| pUMESDsy-K199P × K224P × H103L | 108.0 |
| pUMESDsy-K176P × K199P × K224P × H103L | 96.9 |

EXAMPLE 18

Synthesis of Cyanohydrin and Hydroxycarboxylic Acid with Improved Hydroxynitrile Lyase (1) Synthesis of Cyanohydrin C600/pOXN103V2I jar culture (40 ml) obtained in (3) in Example 12 was centrifuged (3,700×g, 10 minutes, 4° C.). After removal of 35 ml of supernatant, the remaining cells and culture broth were resuspended. The resultant cell suspension was disrupted with a sonicator VP-15S (Taitec, Japan) under the following conditions: output control 4, DUTY CYCLE 40%, PULS, TIMER=B mode 10s, while ice-cooling. Three minutes disrupting was repeated 5 times. The liquid containing disrupted cell suspension was centrifuged again (10,000× g, 5 minutes, 4° C.), and the resultant supernatant was collected as an enzyme solution of improved hydroxynitrile lyase. The degradation activity of this enzyme solution was calculated in the same manner as described in (1-4) in Example 12. The activity of this enzyme solution was 1171 U/ml. The enzyme solution (3.7 g) (corresponding to 6450 U) was mixed with t-butylmethylether (175.1 g). While maintaining the reaction system at 15-18° C. and agitating sufficiently, HCN (47.6 g) and benzaldehyde (124.6 g) were added dropwise continuously over about 4 hours. After completion of the dropping, the reaction system was maintained at 15-18° C. for one hour and agitated sufficiently. After completion of the reaction, the reaction solution was analyzed by HPLC in the same manner as described in (2-3) in Example 8. As a result, the concentration of mandelonitrile was 45% by weight and the optical purity thereof was 98%ee S-enantiomer excess.

(2) Synthesis of Hydroxycarboxylic Acid

While agitating at 30-35° C. for 16 hours, the mandelonitrile solution (131 g) obtained in (1) above was added dropwise to 35% hydrochloric acid (147 g). This reaction solution was a slurry. The reaction solution after 16 hours agitation was analyzed by HPLC. As a result, mandelonitrile was not detected, and mandelamide and mandelic acid were present in a mixed state. To the total volume of the reaction solution after 16 hours agitation, 320 g of water was added and agitated at 75° C. for 2 hours for hydrolysis. This reaction solution was homogeneous. HPLC analysis of this reaction solution revealed that mandelonitrile and mandelamide were not detected, and that the concentration of mandelic acid was 21% and the optical purity thereof was 98% ee S-enantiomer excess.

INDUSTRIAL APPLICABILITY

According to the present invention, improved hydroxynitrile lyases in which amino acids in a wild-type hydroxynitrile lyase are substituted; and genes encoding the same can be obtained. The improved hydroxynitrile lyase gene of the present invention includes not only those genes obtained by introducing mutations into wild-type genes, but also those genes obtained by introducing mutations into host codon-type hydroxynitrile lyase genes which have been mutated according to codon usage of the relevant host.

Further, in a transformant obtained by transducing the gene of the present invention into a host, hydroxynitrile lyase activity per transformant can be improved greatly. Therefore, such a transformant is capable of producing the improved hydroxynitrile lyase in a large quantity and efficiently. Further, with the improved hydroxynitrile lyase of the present invention, it is possible to produce optically active cyanohydrins and optically active hydroxycarboxylic acid efficiently.

Sequence Listing Free Text
SEQ ID NOS: 3-101 Synthetic DNAs

The invention claimed is:

1. An isolated or purified modified hydroxynitrile lyase that is at least 90% homologous to the wild-type hydroxynitrile lyase of *Manihot escuela* of SEQ ID NO: 1 or at least 90% homologous to the wild-type hydroxynitrile lyase of *Hevea brasiliensis* of SEQ ID NO: 102, and that has a substitution of the amino acid residue corresponding to the amino acid residue valine (Val) at position 2 of SEQ ID NO: 1 or corresponding to the amino acid residue alanine (Ala) at position 2 of SEQ ID NO: 102 with a different amino acid residue.

2. The modified hydroxynitrile lyase of claim 1 that is at least 90% homologous to the wild-type hydroxynitrile lyase of *Manihot escuela* of SEQ ID NO: 1 and that has a substitution of the amino acid residue corresponding to the amino acid residue valine (Val) at position 2 of SEQ ID NO: 1 with a different amino acid residue.

3. The modified hydroxynitrile lyase of claim 1, wherein the valine residue corresponding to position 2 in the amino acid sequence of SEQ ID NO: 1 is substituted with an amino acid selected from the group consisting of lysine, asparagine, isoleucine, arginine and glutamine.

4. The modified hydroxynitrile lyase of claim 1, wherein the valine residue corresponding to position 2 in the amino acid sequence of SEQ ID NO: 1 is substituted with an amino acid selected from the group consisting of proline, threonine, tyrosine, leucine, methionine, serine, glutamic acid, alanine, glycine and aspartic acid.

5. The modified hydroxynitrile lyase of claim 1, wherein at least one lysine residue corresponding to a lysine residue of the amino acid sequence of SEQ ID NO: 1 is substituted with an amino acid residue other than lysine.

6. The modified hydroxynitrile lyase of claim 1, wherein at least one lysine residue corresponding to a lysine residue of the amino acid sequence of SEQ ID NO: 1 is substituted with an amino acid having one or both of properties (a) and (b):
(a) an amino acid containing one or two nitrogen atoms in its molecule selected from the group consisting of ala, asn, asp, cys, gln, glu, gly, iso, leu, met, phe, pro, ser, thr, trp, tyr and val;
(b) a neutral amino acid.

7. The modified hydroxynitrile lyase of claim 1, wherein at least one lysine residue corresponding to a lysine residue of the amino acid sequence of SEQ ID NO:1 is substituted with proline.

8. The modified hydroxynitrile lyase of claim 1 that is at least 90% homologous to the wild-type hydroxynitrile lyase of *Hevea brasiliensis* of SEQ ID NO: 102 and that has a substitution of the amino acid residue corresponding to the amino acid residue alanine (Ala) at position 2 of SEQ ID NO: 102 with a different amino acid residue.

9. The modified hydroxynitrile lyase of claim 1, wherein the valine residue corresponding to position 2 in the amino acid sequence of SEQ ID NO: 102 is substituted with an amino acid selected from the group consisting of lysine, asparagine, isoleucine, arginine and glutamine.

10. The modified hydroxynitrile lyase of claim 1, wherein the alanine residue corresponding to position 2 in the amino acid sequence of SEQ ID NO: 102 is substituted with an amino acid selected from the group consisting of proline, threonine, tyrosine, leucine, methionine, serine, glutamic acid, glycine and aspartic acid.

11. The modified hydroxynitrile lyase of claim 1, wherein at least one lysine residue corresponding to a lysine residue of the amino acid sequence of SEQ ID NO:1 is substituted with an amino acid having one or both of properties (a) and (b): (a) an amino acid containing one or two nitrogen atoms in its molecule selected from the group consisting of ala, asn, asp, cys, gln, glu, gly, iso, leu, met, phe, pro, ser, thr, trp, tyr and val; (b) a neutral amino acid 12. The modified hydroxynitrile lyase of claim 1, wherein at least one lysine residue corresponding to a lysine residue of the amino acid sequence of SEQ ID NO:102 is substituted with proline.

13. The modified hydroxynitrile lyase of claim 1, wherein at least one lysine residue corresponding to a lysine residue of the amino acid sequence of SEQ ID NO: 102 is substituted with an amino acid residue other than lysine.

14. The modified hydroxynitrile lyase of claim 1, wherein the position corresponding to position 103 of SEQ ID NO: 1 or 102 is substituted with a neutral amino acid.

15. The modified hydroxynitrile lyase of claim 1, wherein the position corresponding to position 103 of SEQ ID NO: 1 or 102 is substituted with an amino acid selected from the group consisting of ala, asn, asp, cys, gln, glu, gly, ile, leu, lys, met, phe, pro, ser, thr, trp, tyr and val.

16. The hydroxynitrile lyase of claim 1, wherein at least one lysine residue present in a region corresponding to positions 175 to 224 of the amino acid sequence of SEQ ID NO: 1 or SEQ ID NO: 102 is substituted with a different amino acid than those in SEQ ID NO: 1 or SEQ ID NO: 102.

17. The hydroxynitrile lyase of claim 1, wherein at least one lysine residue present in a region corresponding to positions 175 to 224 of the amino acid sequence of SEQ ID NO: 1 or SEQ ID NO: 102 is substituted with an amino acid having one or both of properties (a) and (b):
(a) an amino acid containing one or two nitrogen atoms in its molecule selected from the group consisting of ala, asn, asp, cys, gln, glu, gly, iso, leu, met, phe, pro, ser, thr, trp, tyr and val;
(b) a neutral amino acid.

18. The hydroxynitrile lyase of claim 1, wherein at least one lysine residue present in a region corresponding to positions 175 to 224 of the amino acid sequence of SEQ ID NO: 1 or SEQ ID NO: 102 is substituted with proline.

19. The hydroxynitrile lyase of claim 1, wherein at least one lysine residue selected from the group consisting of the lysine residues corresponding to positions 176, 199, and 224 in the amino acid sequence of SEQ ID NO: 1 is substituted with a different amino acid than that in SEQ ID NO: 1.

20. The hydroxynitrile lyase of claim 1, wherein at least one lysine residue selected from the group consisting of the lysine residues corresponding to positions 175, 198, and 223 in the amino acid sequence of SEQ ID NO: 102 is substituted with a different amino acid than that in SEQ ID NO: 102.

21. The modified hydroxynitrile lyase of claim 1 that has a higher specific activity than the wild-type hydroxynitrile lyase of SEQ ID NO: 1 or SEQ ID NO: 102.

22. The modified hydroxynitrile lyase of claim 1 that has a higher specific activity to catalyze a reaction producing a cyanohydrin from either ketone or from aldehyde and a cyanide compound, as well as the ability to catalyze a reverse reaction thereof, than the wild-type hydroxynitrile lyase of SEQ ID NO: 1 or SEQ ID NO: 102.

23. A modified hydroxynitrile lyase of claim 1 that is recombinantly produced by a host cell transformed with a polynucleotide encoding said lyase.

24. A composition comprising the isolated or purified modified hydroxynitrile lyase of claim 1.

25. A method for producing a cyanohydrin, comprising:
treating a ketone compound or an aldehyde compounds, and a cyanide compound with the modified hydroxynitrile lyase of claim 1, and
recovering the cyanohydrin from the treated culture.

26. A method for producing a hydroxycarboxylic acid, comprising hydrolyzing the cyanohydrin obtained by the method of claim 25.

27. An isolated or purified polynucleotide encoding the hydroxynitrile lyase of claim 1.

28. A recombinant vector comprising the polynucleotide of claim 27.

29. A transformant obtained by introducing the recombinant vector of claim 28 into a host.

30. A culture obtained by culturing the transformant of claim 29.

31. A method for producing a hydroxynitrile lyase, comprising recovering the improved hydroxynitrile lyase from the culture of claim 30.

\* \* \* \* \*

```
                         SEQUENCE LISTING

<160> NUMBER OF SEQ ID NOS: 103

<210> SEQ ID NO 1
<211> LENGTH: 258
<212> TYPE: PRT
<213> ORGANISM: Manihot esculenta

<400> SEQUENCE: 1

Met Val Thr Ala His Phe Val Leu Ile His Thr Ile Cys His Gly Ala
1               5                   10                  15

Trp Ile Trp His Lys Leu Lys Pro Ala Leu Glu Arg Ala Gly His Lys
            20                  25                  30

Val Thr Ala Leu Asp Met Ala Ala Ser Gly Ile Asp Pro Arg Gln Ile
        35                  40                  45

Glu Gln Ile Asn Ser Phe Asp Glu Tyr Ser Glu Pro Leu Leu Thr Phe
    50                  55                  60

Leu Glu Lys Leu Pro Gln Gly Glu Lys Val Ile Ile Val Gly Glu Ser
65                  70                  75                  80

Cys Ala Gly Leu Asn Ile Ala Ile Ala Ala Asp Arg Tyr Val Asp Lys
                85                  90                  95

Ile Ala Ala Gly Val Phe His Asn Ser Leu Leu Pro Asp Thr Val His
            100                 105                 110

Ser Pro Ser Tyr Thr Val Glu Lys Leu Leu Glu Ser Phe Pro Asp Trp
        115                 120                 125

Arg Asp Thr Glu Tyr Phe Thr Phe Thr Asn Ile Thr Gly Glu Thr Ile
130                 135                 140

Thr Thr Met Lys Leu Gly Phe Val Leu Leu Arg Glu Asn Leu Phe Thr
145                 150                 155                 160

Lys Cys Thr Asp Gly Glu Tyr Glu Leu Ala Lys Met Val Met Arg Lys
                165                 170                 175

Gly Ser Leu Phe Gln Asn Val Leu Ala Gln Arg Pro Lys Phe Thr Glu
            180                 185                 190

Lys Gly Tyr Gly Ser Ile Lys Lys Val Tyr Ile Trp Thr Asp Gln Asp
        195                 200                 205

Lys Ile Phe Leu Pro Asp Phe Gln Arg Trp Gln Ile Ala Asn Tyr Lys
    210                 215                 220

Pro Asp Lys Val Tyr Gln Val Gln Gly Gly Asp His Lys Leu Gln Leu
225                 230                 235                 240

Thr Lys Thr Glu Glu Val Ala His Ile Leu Gln Glu Val Ala Asp Ala
                245                 250                 255

Tyr Ala

<210> SEQ ID NO 2
<211> LENGTH: 777
<212> TYPE: DNA
<213> ORGANISM: Manihot esculenta

<400> SEQUENCE: 2
atggtaactg cacattttgt tctgattcat accatttgcc atggtgcatg gatttggcat     60
aagctcaaac cagcccttga gagagctggc cacaaagtca ctgcactgga catggcagcc    120
agcggcattg acccaaggca aattgagcag attaattcat ttgatgaata ctctgaaccc    180
ttattgactt tcttggagaa actccctcaa ggggaaaagg tcatcattgt tggtgagagc    240
```

```
tgtgcagggc tgaatattgc tattgctgct gatagatacg ttgacaaaat tgcagctggt    300
gttttccaca attccttatt gccagacacc gttcatagcc catcttacac tgtggaaaag    360
cttttggagt cgtttcctga ctggagagac acagagtatt ttacgttcac taatatcact    420
ggagagacaa ttacaacaat gaagctgggc ttcgtacttc tgagggaaaa tttatttacc    480
aaatgcactg atggggaata tgaactggca aaaatggtaa tgaggaaggg atcactgttt    540
caaaatgttt tggctcagag accgaagttc accgaaaaag gttacggatc aattaagaaa    600
gtttatattt ggaccgatca agacaaaata ttttaccag actttcaacg ctggcaaatt     660
gcaaactaca aaccagacaa ggtttatcag gttcaaggtg gagatcataa gctccagctt    720
acaaaaactg aggaggtagc tcatattctc caagaggtgg ctgatgcata tgcttga       777

<210> SEQ ID NO 3
<211> LENGTH: 777
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
atggtgaccg cgcattttgt gctgattcat accatttgcc atggcgcgtg gatttggcat    60
aaactgaaac cggcgctgga acgcgcgggc cataaagtga ccgcgctgga tatggcggcg   120
agcggcattg atccgcgcca gattgaacag attaacagct ttgatgaata tagcgaaccg   180
ctactgacct ttctggaaaa actgccgcag ggcgaaaaag tgattattgt gggcgaaagc   240
tgcgcgggcc tgaacattgc gattgcggcg atcgctatg tggataaaat tgcggcgggc   300 gttttttcata acagcctgct gccggatacc gtgcatagcc cgagctatac cgtggaaaaa   360
ctgctggaaa gctttccgga ttggcgcgat accgaatatt ttacctttac caacattacc    420
ggcgaaacca ttaccaccat gaaactgggc tttgtgctgc tgcgcgaaaa cctgtttacc    480
aaatgcaccg atggcgaata tgaactggcg aaaatggtga tgcgcaaagg cagcctgttt    540
cagaacgtgc tggcgcagcg cccgaaattt accgaaaaag gctatggcag cattaaaaaa    600
gtgtatattt ggaccgatca ggataaaatt ttctgccgg attttcagcg ctggcagatt     660
gcgaactata aaccggataa agtgtatcag gtgcagggcg gcgatcataa actgcagctg    720
accaaaaccg aagaagtggc gcatattctg caggaagtgg cggatgcgta tgcgtga      777

<210> SEQ ID NO 4
<211> LENGTH: 72
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cgggatcccc aaaaagagtt agatatcatt tccaaaatgg taactgcaca ttttgttctg    60
attcatacca tt                                                        72

<210> SEQ ID NO 5
<211> LENGTH: 70
<212> TYPE: DNA
<213> ORGANISM: Artificial Sequence
<220> FEATURE:
<223> OTHER INFORMATION: Description of Artificial Sequence: Synthetic
      primer
```

-continued

```
<400> SEQUENCE: 5
ttgttctgat tcataccatt tgccatggtg catggatttg cataagctc aaaccagccc        60 ttgagagagc                                                              70

<210> SEQ ID NO 6
<211> LENGTH: 70
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
aaaccagccc ttgagagagc tggccacaaa gtcactgcac tggacatggc agccagcggc       60
attgacccaa                                                              70

<210> SEQ ID NO 7
<211> LENGTH: 70
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
agccagcggc attgacccaa ggcaaattga gcagattaat tcatttgatg aatactctga       60
acccttattg                                                              70

<210> SEQ ID NO 8
<211> LENGTH: 70
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tattgccaga caccgttcat agcccatctt acactgtgga aaagcttttg gagtcgtttc       60
ctgactggag                                                              70

<210> SEQ ID NO 9
<211> LENGTH: 70
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gagtcgtttc ctgactggag agacacagag tattttacgt tcactaatat cactggagag       60
acaattacaa                                                              70

<210> SEQ ID NO 10
<211> LENGTH: 70
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cactggagag acaattacaa caatgaagct gggcttcgta cttctgaggg aaaatttatt       60
taccaaatgc                                                              70
```

<210> SEQ ID NO 11
<211> LENGTH: 70
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
atcaagacaa aatatttta ccagactttc aacgctggca aattgcaaac tacaaaccag      60
acaaggttta                                                            70

<210> SEQ ID NO 12
<211> LENGTH: 70
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tacaaaccag acaaggttta tcaggttcaa ggtggagatc ataagctcca gcttacaaaa      60
actgaggagg                                                            70

<210> SEQ ID NO 13
<211> LENGTH: 70
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gcttacaaaa actgaggagg tagctcatat tctccaagag gtggctgatg catatgcttg      60
aagcttttag                                                            70

<210> SEQ ID NO 14
<211> LENGTH: 79
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gcggtaccct taataggata tttatttatt taatttaaag attacataat agggataaca      60
ttcccttaaa tacacacat                                                  79

<210> SEQ ID NO 15
<211> LENGTH: 80
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
attcccttaa atacacacat ctcagcaaat gaagagacac caacgtggaa ctctcccata      60
tttaaagaaa aaaaaactca                                                 80

<210> SEQ ID NO 16
<211> LENGTH: 70
<212> TYPE: DNA

-continued

<213> ORGANISM: Artificial Sequence
<220> FEATURE:
<223> OTHER INFORMATION: Description of Artificial Sequence: Synthetic
      primer

<400> SEQUENCE: 16
tttaaagaaa aaaaaactca aactttattt tagtgcaatt taattctcac atgaaaatgt     60
gagattattt                                                            70

<210> SEQ ID NO 17
<211> LENGTH: 70
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
atgaaaatgt gagattattt ataactgcac ccaggttaac ttaataggag ctaaaagctt     60
caagcatatg                                                            70

<210> SEQ ID NO 18
<211> LENGTH: 70
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
taaaaatatt ttgtcttgat cggtccaaat ataaactttc ttaattgatc cgtaaccttt     60
ttcggtgaac                                                            70

<210> SEQ ID NO 19
<211> LENGTH: 70
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
cgtaaccttt ttcggtgaac ttcggtctct gagccaaaac attttgaaac agtgatccct     60
tcctcattac                                                            70

<210> SEQ ID NO 20
<211> LENGTH: 70
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
agtgatccct tcctcattac cattttttgcc agttcatatt ccccatcagt gcatttggta    60
aataaatttt                                                            70

<210> SEQ ID NO 21
<211> LENGTH: 70
<212> TYPE: DNA
<213> ORGANISM: Artificial Sequence
<220> FEATURE:
<223> OTHER INFORMATION: Description of Artificial Sequence: Synthetic
      primer -continued

```
<400> SEQUENCE: 21
atgaacggtg tctggcaata aggaattgtg gaaaacacca gctgcaattt tgtcaacgta      60
tctatcagca                                                            70

<210> SEQ ID NO 22
<211> LENGTH: 70
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
tgtcaacgta tctatcagca gcaatagcaa tattcagccc tgcacagctc tcaccaacaa      60
tgatgacctt                                                            70

<210> SEQ ID NO 23
<211> LENGTH: 70
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
tcaccaacaa tgatgacctt ttccccttga gggagtttct ccaagaaagt caataagggt      60
tcagagtatt                                                            70

<210> SEQ ID NO 24
<211> LENGTH: 62
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ccccaaactg cagtaaggag gaatagaaaa tggtaactgc acattttgtt ctgattcata      60
cc                                                                    62

<210> SEQ ID NO 25
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
tagtgcaatt ggatcctcac atgaaaatgt gag                                  33

<210> SEQ ID NO 26
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ccaccatggt aactgcacat tttgttctg                                       29

<210> SEQ ID NO 27
<211> LENGTH: 33
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ggcctgcagg ttaacttaat aggagctaaa agc                                33

<210> SEQ ID NO 28
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
aaaagagtta gatatcattt ccaaaatggt gaccgcgcat tttgtgctg               49

<210> SEQ ID NO 29
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
tccacgcgcc atggcaaatg gtatgaatca gcacaaaatg cgcggtcacc              50

<210> SEQ ID NO 30
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
ttgccatggc gcgtggattt ggcataaact gaaaccggcg ctggaacgcg              50

<210> SEQ ID NO 31
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
ccatatccag cgcggtcact ttatggcccg cgcgttccag cgccggtttc              50

<210> SEQ ID NO 32
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
agtgaccgcg ctggatatgg cggcgagcgg cattgatccg cgccagattg              50

<210> SEQ ID NO 33
<211> LENGTH: 50
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 33
cgctatattc atcaaagctg ttaatctgtt caatctggcg cggatcaatg         50

<210> SEQ ID NO 34
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
cagctttgat gaatatagcg aaccgctact gacctttctg gaaaaactgc         50

<210> SEQ ID NO 35
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
cgcccacaat aatcactttt tcgccctgcg gcagtttttc cagaaaggtc         50

<210> SEQ ID NO 36
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
aaaagtgatt attgtgggcg aaagctgcgc gggcctgaac attgcgattg         50

<210> SEQ ID NO 37
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
ccgcaatttt atccacatag cgatccgccg caatcgcaat gttcaggccc         50

<210> SEQ ID NO 38
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
ctatgtggat aaaattgcgg cgggcgtttt tcataacagc ctgctgccgg         50

<210> SEQ ID NO 39
<211> LENGTH: 49
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 39
ccacggtata gctcgggcta tgcacggtat ccggcagcag gctgttatg                49

<210> SEQ ID NO 40
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
tagcccgagc tataccgtgg aaaaactgct ggaaagcttt ccggattggc               50

<210> SEQ ID NO 41
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
tgttggtaaa ggtaaaatat tcggtatcgc gccaatccgg aaagctttcc              50

<210> SEQ ID NO 42
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
atattttacc tttaccaaca ttaccggcga aaccattacc accatgaaac              50

<210> SEQ ID NO 43
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
acaggttttc gcgcagcagc acaaagccca gtttcatggt ggtaatgg                48

<210> SEQ ID NO 44
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
ctgctgcgcg aaaacctgtt taccaaatgc accgatggcg aatatgaac                49

<210> SEQ ID NO 45
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide -continued

<400> SEQUENCE: 45
ggctgccttt gcgcatcacc attttcgcca gttcatattc gccatcggtg          50

<210> SEQ ID NO 46
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
ggtgatgcgc aaaggcagcc tgtttcagaa cgtgctggcg cagcgcccg           49

<210> SEQ ID NO 47
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
taatgctgcc atagcctttt tcggtaaatt tcgggcgctg cgccagcacg          50

<210> SEQ ID NO 48
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
aaaaggctat ggcagcatta aaaaagtgta tatttggacc gatcagg             47

<210> SEQ ID NO 49
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
agcgctgaaa atccggcaga aaaattttat cctgatcggt ccaaatatac          50

<210> SEQ ID NO 50
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
gccggatttt cagcgctggc agattgcgaa ctataaaccg gataaagtg           49

<210> SEQ ID NO 51
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51

```
gtttatgatc gccgccctgc acctgataca ctttatccgg tttatagttc          50
```

<210> SEQ ID NO 52
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52

```
gggcggcgat cataaactgc agctgaccaa aaccgaagaa gtggcgc             47
```

<210> SEQ ID NO 53
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53

```
catacgcatc cgccacttcc tgcagaatat gcgccacttc ttcggttttg          50
```

<210> SEQ ID NO 54
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54

```
agtggcggat gcgtatgcgt gaagctttta gctcctatta agttaacctg          50
```

<210> SEQ ID NO 55
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55

```
tgaaaatgtg agattattta taactgcacc caggttaact taataggagc          50
```

<210> SEQ ID NO 56
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56

```
taaataatct cacattttca tgtgagaatt aaattgcact aaaataaag           49
```

<210> SEQ ID NO 57
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57

```
catatttaaa gaaaaaaaaa ctcaaacttt attttagtgc aatttaattc          50
```

```
<210> SEQ ID NO 58
<211> LENGTH: 61
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
tgcaaagcat gctaaggagg aatagaaaat ggtgaccgcg cattttgtgc tgattcatac    60
c                                                                    61

<210> SEQ ID NO 59
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
attttagtgc aattggatcc tcacatgaaa atgtgag                              37

<210> SEQ ID NO 60
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
agaccatggc tactgcacat tttgtt                                          26

<210> SEQ ID NO 61
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
agaccatgga cactgcacat tttgtt                                          26

<210> SEQ ID NO 62
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
agaccatgga aactgcacat tttgtt                                          26

<210> SEQ ID NO 63
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
agaccatggg cactgcacat tttgtt                                          26
```

```
<210> SEQ ID NO 64
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
atttccatca tgatcactgc acattttgtt ctg                              33

<210> SEQ ID NO 65
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
agatcatgat gactgcacat tttgttc                                     27

<210> SEQ ID NO 66
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
agatcatgac cactgcacat tttgtt                                      26

<210> SEQ ID NO 67
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
agatcatgaa cactgcacat tttgttc                                     27

<210> SEQ ID NO 68
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
agatcatgaa aactgcacat tttgttc                                     27

<210> SEQ ID NO 69
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
agatcatgag cactgcacat tttgtt                                      26

<210> SEQ ID NO 70
```

-continued

```
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
agaacatgtt cactgcacat tttgttc                                              27

<210> SEQ ID NO 71
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
agaacatgta cactgcacat tttgttc                                              27

<210> SEQ ID NO 72
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
agaacatgtg cactgcacat tttgttc                                              27

<210> SEQ ID NO 73
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
agaacatgtg gactgcacat tttgttc                                              27

<210> SEQ ID NO 74
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
aaacagacca tgcgtactgc acattttg                                             28

<210> SEQ ID NO 75
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
caaaatgtgc agtacgcatg gtctgttt                                             28

<210> SEQ ID NO 76
<211> LENGTH: 28
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 76
aaacagacca tgcagactgc acattttg                                            28

<210> SEQ ID NO 77
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
caaaatgtgc agtctgcatg gtctgttt                                            28

<210> SEQ ID NO 78
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
aaacagacca tgcacactgc acattttg                                            28

<210> SEQ ID NO 79
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
caaaatgtgc agtgtgcatg gtctgttt                                            28

<210> SEQ ID NO 80
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
aaacagacca tgctgactgc acattttg                                            28

<210> SEQ ID NO 81
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
caaaatgtgc agtcagcatg gtctgttt                                            28

<210> SEQ ID NO 82
<211> LENGTH: 28
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 82
aaacagacca tgccgactgc acattttg                                          28

<210> SEQ ID NO 83
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
caaaatgtgc agtcggcatg gtctgttt                                          28

<210> SEQ ID NO 84
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
aacagctatg accatg                                                       16

<210> SEQ ID NO 85
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
gtaaaacgac ggccagt                                                      17

<210> SEQ ID NO 86
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
gctggtgttt tcctgaattc cttattgcc                                         29

<210> SEQ ID NO 87
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
ggcaataagg aattcaggaa aacaccagc                                         29

<210> SEQ ID NO 88
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

```
<220> FEATURE:
<221> NAME/KEY: modified_base
<222> LOCATION: (14)..(15)
<223> OTHER INFORMATION: a, c, t, g, unknown or other

<400> SEQUENCE: 88
ggcgggcgtt tttnnsaaca gcctgctgcc                                          30

<210> SEQ ID NO 89
<211> LENGTH: 40
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (16)..(17)
<223> OTHER INFORMATION: a, c, t, g, unknown or other

<400> SEQUENCE: 89
gcagctggtg ttttcnnsaa ttccttattg ccagacaccg                               40

<210> SEQ ID NO 90
<211> LENGTH: 30
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (16)..(17)
<223> OTHER INFORMATION: a, c, t, g, unknown or other

<400> SEQUENCE: 90
ggcagcaggc tgttsnnaaa aacgcccgcc                                          30

<210> SEQ ID NO 91
<211> LENGTH: 40
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (24)..(25)
<223> OTHER INFORMATION: a, c, t, g, unknown or other

<400> SEQUENCE: 91
cggtgtctgg caataaggaa ttsnngaaaa caccagctgc                               40

<210> SEQ ID NO 92
<211> LENGTH: 46
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(23)
<223> OTHER INFORMATION: a, c, t, g, unknown or other

<400> SEQUENCE: 92
ctggcgaaaa tggtgatgcg cnnsggcagc ctgtttcaga acgtgc                        46

<210> SEQ ID NO 93
<211> LENGTH: 50
```

-continued

```
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (23)..(24)
<223> OTHER INFORMATION: a, c, t, g, unknown or other

<400> SEQUENCE: 93
cgaaaaaggc tatggcagca ttnnsaaagt gtatatttgg accgatcagg                50

<210> SEQ ID NO 94
<211> LENGTH: 44
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (23)..(25)
<223> OTHER INFORMATION: a, c, t, g, unknown or other

<400> SEQUENCE: 94
gcgctggcag attgcgaact atnnnccgga taaagtgtat cagg                      44

<210> SEQ ID NO 95
<211> LENGTH: 46
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (24)..(25)
<223> OTHER INFORMATION: a, c, t, g, unknown or other

<400> SEQUENCE: 95
gcacgttctg aaacaggctg ccsnngcgca tcaccatttt cgccag                    46

<210> SEQ ID NO 96
<211> LENGTH: 48
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (27)..(28)
<223> OTHER INFORMATION: a, c, t, g, unknown or other

<400> SEQUENCE: 96
cctgatcggt ccaaatatac actttsnnaa tgctgccata gccttttt                  48

<210> SEQ ID NO 97
<211> LENGTH: 44
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (20)..(22)
<223> OTHER INFORMATION: a, c, t, g, unknown or other

<400> SEQUENCE: 97
```
cctgatacac tttatccggn nnatagttcg caatctgcca gcgc          44

<210> SEQ ID NO 98
<211> LENGTH: 46
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (24)..(24)
<223> OTHER INFORMATION: a, c, t, g, unknown or other

<400> SEQUENCE: 98
ctggcgaaaa tggtgatgcg cccnggcagc ctgtttcaga acgtgc          46

<210> SEQ ID NO 99
<211> LENGTH: 50
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (25)..(25)
<223> OTHER INFORMATION: a, c, t, g, unknown or other

<400> SEQUENCE: 99
cgaaaaaggc tatggcagca ttccnaaagt gtatatttgg accgatcagg          50

<210> SEQ ID NO 100
<211> LENGTH: 46
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (23)..(23)
<223> OTHER INFORMATION: a, c, t, g, unknown or other

<400> SEQUENCE: 100
gcacgttctg aaacaggctg ccngggcgca tcaccatttt cgccag          46

<210> SEQ ID NO 101
<211> LENGTH: 48
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (26)..(26)
<223> OTHER INFORMATION: a, c, t, g, unknown or other

<400> SEQUENCE: 101
cctgatcggt ccaaatatac actttnggaa tgctgccata gccttttt          48

<210> SEQ ID NO 102
<211> LENGTH: 257
<212> TYPE: PRT
<213> ORGANISM: Hevea brasiliensis

<400> SEQUENCE: 102

Met Ala Phe Ala His Phe Val Leu Ile His Thr Ile Cys His Gly Ala
1               5                   10                  15

Trp Ile Trp His Lys Leu Lys Pro Leu Glu Ala Leu Gly His Lys
            20                  25                  30

Val Thr Ala Leu Asp Leu Ala Ala Ser Gly Val Asp Pro Arg Gln Ile
        35                  40                  45

Glu Glu Ile Gly Ser Phe Asp Glu Tyr Ser Glu Pro Leu Leu Thr Phe
    50                  55                  60

Leu Glu Ala Leu Pro Pro Gly Glu Lys Val Ile Leu Val Gly Glu Ser
65                  70                  75                  80

Cys Gly Gly Leu Asn Ile Ala Ile Ala Ala Asp Lys Tyr Cys Glu Lys
                85                  90                  95

Ile Ala Ala Ala Val Phe His Asn Ser Val Leu Pro Asp Thr Glu His
                100                 105                 110

Cys Pro Ser Tyr Val Val Asp Lys Leu Met Glu Val Phe Pro Asp Trp
            115                 120                 125

Lys Asp Thr Thr Tyr Phe Thr Tyr Thr Lys Asp Gly Lys Glu Ile Thr
            130                 135                 140

Gly Leu Lys Leu Gly Phe Thr Leu Leu Arg Glu Asn Leu Tyr Thr Leu
145                 150                 155                 160

Cys Gly Pro Glu Glu Tyr Glu Leu Ala Lys Met Leu Thr Arg Lys Gly
                165                 170                 175

Ser Leu Phe Gln Asn Ile Leu Ala Lys Arg Pro Phe Phe Thr Lys Glu
                180                 185                 190

Gly Tyr Gly Ser Ile Lys Lys Ile Tyr Val Trp Thr Asp Gln Asp Glu
            195                 200                 205

Ile Phe Leu Pro Glu Phe Gln Leu Trp Gln Ile Glu Asn Tyr Lys Pro
            210                 215                 220

Asp Lys Val Tyr Lys Val Glu Gly Gly Asp His Lys Leu Gln Leu Thr
225                 230                 235                 240

Lys Thr Lys Glu Ile Ala Glu Ile Leu Gln Glu Val Ala Asp Thr Tyr
                245                 250                 255

Asn

<210> SEQ ID NO 103
<211> LENGTH: 774
<212> TYPE: DNA
<213> ORGANISM: Hevea brasiliensis

<400> SEQUENCE: 103
atggcattcg ctcattttgt tcttattcat accatatgcc acggtgcatg gatttggcac      60
aagctcaaac ccctccttga ggcacttggc cacaaggtta ctgcactgga ccttgcagca     120
agcggcgttg acccaaggca aattgaggag attggctcat tgatgagta ttctgaaccc      180 ttgttgacgt tcttggaggc actccctcca ggggaaaagg tgattctggt tggcgagagc     240
tgtggaggac tcaatatagc aattgctgct gataaatact gtgaaaagat tgcagctgct     300
gttttccaca attcagtatt gccagacacc gagcactgcc catcttacgt cgtggataag     360
ctcatggagg tgtttcccga ctggaaagac accacgtatt ttacgtacac taaagatggc     420
aaggagataa ctggattgaa actgggcttc acgcttctga gggaaaattt atataccctt     480
tgcggtcctg aggaatatga actggcgaag atgttgacaa ggaagggatc attatttcaa     540

-continued

```
aatattttag ctaagcgacc attcttcact aaggaaggtt acggatcgat taagaaaatt    600
tatgtgtgga ccgaccaaga cgaaatattt ttacctgaat ttcaactctg gcaaatagaa    660
aactataaac cagacaaggt ttataaggtc gaaggtggag atcataaatt gcagcttaca    720
aagactaagg agatcgctga aattctccaa gaggtggctg atacctataa ttga          774
```